(12) United States Patent
Courvoisier et al.

(10) Patent No.: US 8,076,366 B2
(45) Date of Patent: Dec. 13, 2011

(54) FORMS OF BENDAMUSTINE FREE BASE

(75) Inventors: Laurent D. Courvoisier, West Chester, PA (US); Mark Eddleston, Chilwell (GB); R. Curtis Haltiwanger, West Chester, PA (US); Robert E. McKean, West Chester, PA (US)

(73) Assignee: Cephalon, Inc., Frazer, PA (US)

(*) Notice: Subject to any disclaimer, the term of this patent is extended or adjusted under 35 U.S.C. 154(b) by 200 days.

(21) Appl. No.: 12/687,398

(22) Filed: Jan. 14, 2010

(65) Prior Publication Data
US 2010/0210701 A1 Aug. 19, 2010

Related U.S. Application Data

(60) Provisional application No. 61/144,843, filed on Jan. 15, 2009.

(51) Int. Cl.
  *A61K 31/415* (2006.01)
  *C07D 235/00* (2006.01)
(52) U.S. Cl. ..................... 514/394; 548/308.7
(58) Field of Classification Search .................. 514/394; 548/308.7
See application file for complete search history.

(56) References Cited

U.S. PATENT DOCUMENTS

| | | | |
|---|---|---|---|
| 5,204,335 A | 4/1993 | Sauerbier et al. |
| 5,227,373 A | 7/1993 | Alexander et al. |
| 5,750,131 A | 5/1998 | Wichert et al. |
| 5,770,230 A | 6/1998 | Teagarden et al. |
| 5,776,456 A | 7/1998 | Anderson et al. |
| 5,955,504 A | 9/1999 | Wechter et al. |
| 5,972,912 A | 10/1999 | Marek et al. |
| 6,034,256 A | 3/2000 | Carter et al. |
| 6,077,850 A | 6/2000 | Carter et al. |
| 6,090,365 A | 7/2000 | Kaminski et al. |
| 6,271,253 B1 | 8/2001 | Carter et al. |
| 6,380,210 B1 | 4/2002 | Desimone et al. |
| 6,492,390 B2 | 12/2002 | Carter et al. |
| 6,545,034 B1 | 4/2003 | Carson et al. |
| 6,569,402 B1 | 5/2003 | Cheesman et al. |
| 6,573,292 B1 | 6/2003 | Nardella |
| 6,613,927 B1 | 9/2003 | Kwok |
| 2003/0232874 A1 | 12/2003 | Nardella |
| 2004/0053972 A1 | 3/2004 | Narn |
| 2004/0058956 A1 | 3/2004 | Akiyama et al. |
| 2004/0072889 A1 | 4/2004 | Masferrer |
| 2004/0096436 A1 | 5/2004 | Carson et al. |
| 2004/0152672 A1 | 8/2004 | Carson et al. |
| 2004/0247600 A1 | 12/2004 | Leoni |
| 2005/0020615 A1 | 1/2005 | Rubino |
| 2005/0060028 A1 | 3/2005 | Horres et al. |
| 2005/0176678 A1 | 8/2005 | Horres et al. |
| 2006/0051412 A1 | 3/2006 | Petereit et al. |

FOREIGN PATENT DOCUMENTS

| | | |
|---|---|---|
| DE | 80967 A | 4/1895 |
| DE | 159877 A1 | 4/1905 |
| DE | 293808 A5 | 8/1916 |
| DE | 159289 A1 | 3/1983 |
| DE | 10016077 | 12/2001 |
| DE | 10306724 | 9/2003 |
| DE | 10304403 | 8/2004 |
| EP | 0656211 B1 | 6/1999 |
| EP | 1354952 A1 | 10/2003 |
| EP | 1444989 A1 | 8/2004 |
| WO | 96/28148 A2 | 9/1996 |
| WO | 96/28148 A3 | 9/1996 |
| WO | 03/066027 A1 | 8/2003 |
| WO | 03/081238 A2 | 10/2003 |
| WO | 03/081238 A3 | 10/2003 |
| WO | 03/086470 A2 | 10/2003 |
| WO | 03/086470 A3 | 10/2003 |
| WO | 03/094990 A1 | 11/2003 |
| WO | 2006/076620 A2 | 7/2006 |
| WO | 2006/076620 A3 | 7/2006 |

OTHER PUBLICATIONS

Aivado et al., "Bendamustine in the Treatment of Chronic Lymphocytic Leukemia: Results and Future Perspectives", Seminars in Oncology, 2002, 29(4) 19-22.

Author Unknown, "Ribomustin: Bendamustine Product Monograph", Ribosepharm GMBH, Munchen Germany, Jan. 2002, 59 pages.

Author Unknown, "Ribomustin: Bendamustine Product Monograph", Ribosepharm GMBH, Munchen Germany, Mar. 2005, 72 pages.

Barman et al., "Bendamustine" Drugs, 2001, 61(5), 631-638, Auckland, New Zealand.

Bremer, "High Rates of Long-lasting remissions after 5-day bendamustine Chemotherapy Cycles in Pre-Treated low-grade non-hodgkin's-lymphomas", Journal of Cancer Research and Clinical Oncology, 2002 , 128(11), 603-609.

Byrn et al., "Pharmaceutical Solids: A Strategic Approach to Regulatory Considerations," Pharmaceutical Research, 1995, 12(7), 945-954.

Chow et al., "Anti-CD20 Antibody (DEC-C2B8, rituximab) enhances efficiency of cytotoxic drugs on neoplastic lymphocytes in vitro: Role of Cytokines complement and caspases", Hematologica, Jan. 2002, 87(1), 33-43.

Chow et al., "In AML Cell Lines Ara-C combined with Purine Analogues is able to Exert Synergistic as well as Antagnostic Effects on Proliferation Apoptosis and Disruption of Mitochondrial Membrane Potential", Leukemia & Lymphoma, 2003, 44(1), 165-173.

Chow et al., "In Vitro Induction of Apoptosis of Neoplastic Cells in Low-Grade non-Hodgkin's Lymphomas by Combination of established cytotoxic drugs with bendamustine", Hematologica, 2001, 86(5), 485-493.

Chow et al., "Synergistic Effects if Chemotherapeutic Drugs in Lymphoma Cells are associated with down-regulation if inhibitor of apoptosis proteins (IAPs), prostate-apoptosis-response-gene 4(Par-4), death-associated protein (Dazz) and with enforced caspase activation", Biochemical Pharmacology, 2003, 66(5), 711-724.

(Continued)

*Primary Examiner* — Rebecca Anderson
*Assistant Examiner* — Samantha Shterengarts

(57) ABSTRACT

Novel polymorphic forms of bendamustine free base are described, including amorphous bendamustine free base, six anhydrous crystalline forms, four hydrate forms, and five solvate forms, with methods of their preparation and use also being described.

33 Claims, 32 Drawing Sheets

OTHER PUBLICATIONS

Diehl et al., "Bendamustine in the Treatment of Hematologic Malignancies", Semin. Oncol., Suppl. 13, 2002, Saundes, Philadelphia, 29(4), 3 pages.

Fichtner et al., "Antineoplastic Activity and Toxicity of some Alkylating Cytostatics (Cyclophosphamide, CCNU, Cytostasan) Encapsulated in Liposomes in different murine tumor models", Journal of Microencapsulation, 1986, 3(2), 77-87.

Ghandi, "Metabolism and Mechanisms of Action of Bendamustine: Rationales for Combination therapeutics", Seminars in Oncology, Suppl. 13, 2002, 29(4), 4-11.

Gust et al., "Investigation on the Stability of Bendamustin, a Cytostatic Agent of the Nitrogen Mustard Type I. Synthesis, Isolation and Characterization if Reference Substances", Monatshefte fur Chemie, 1997, 128(3), 291-299.

Heider et al., "Efficacy and Toxicity of bendamustine in patients with relapsed low-grade non-Hodgkin's lymphomas", Anti-Cancer Drugs, 2001, 12(9), 725-729.

Kath et al., "Bendamustine Monotherapy in advanced and refractory chronic lymphocytic Leukemia", Journal of Cancer Research and Clinical Oncology, 2001, 127(1), 48-54.

Koenigsman et al., "Fludarabine and Bendamustine in Refractory and Relapsed Indolent Lymphoma—a Multicenter Phase I/II Trial of the East German Society of Hematology and Oncology (OSHO)", Leukemia & Lymphoma, 2004, 45 (9), 1821-1827.

Koester et al., "Carboplatin in Combination with bendamustine in previously untreated patients with extensive-stage small lung cancer (SCLC)", Clinical Drug Investigation, 2004, 24(10), 611-618.

Kollmannsberger et al., "Phase II study of Bendamustine in Patients with relapsed or cisplatin-refractory germ cell Cancer", Anti-Cancer Drugs, 2000, 11(7), 535-539.

Konstantinov et al., "Cytotoxic Efficacy of Bendamustine in Human Leukemia and Breast Cancer cell lines", Journal of Cancer Research and Clinical Oncology, 2002, 128(5), 271-278.

Leoni et al., "Sdx-105 (Trenda), Active in Non-Hodgkin's Lymphoma Cells, Induces the Mitotic Catastrophe Death Pathway", Blood, 2004, 104(11), (Abstract).

Maas, "Stability of Bendamustine Hydrochloride in Infusion Solutions", 1994, 49(10), 9 pages.

Niemeyer et al., "SDX-105 (bendamustine) is a Clinically active Chemotherapeutic agent with a distinct mechanism of action", Proc Annu Meet Am Assoc Cancer Res., 2004, 45(1), 2 pages.

Nowak et al, "Upon Drug-Induced Apoptosis in Lymphoma Cells X-linked Inhibitor of Apoptosis (XIAP) Translocates from the Cytosol to the Nucleus", Leukemia & Lymphoma, 2004, 45(7), 1429-1436.

Ponisch et al., "Bendamustine in the Treatment of Multiple Myeloma: Results and Future Perspectives", Seminars in Oncology, Suppl. 13, 2002, 29(4), 23-26.

Preiss et al., "Pharmacokinetics of bendamustine (Cytostasan) in patients", Pharmazie, 1985, 40(11), 782-784.

Rummel et al., "Bendamustine in the Treatment of Non-Hodgkin's Lymphoma: Results and Future Perspectives", Seminars in Oncology, Suppl. 13, 2002, 29(4), 27-32.

Rummel et al., "In Vitro Studies with Bendamustine: Enhanced Activity in Combination with Rituximab", Seminars in Oncology, Suppl. 13, Aug. 2002, 29(4), 12-14.

Scasnar et al., "Radiochemical Assay of Stability of 14C-Cytostasan Solutions During Preparation and Storage", 1988, 121(2m), 489-497.

Schmidt-Hieber et al., "A Phase II Study of bendamustine Chemotherapy as Second-line treatment in metastatic uveal Melanoma", Melanoma Research, 2004, 14(6), 439-442.

Schoffski, "Repeated Administration of Short Infusions of Bendamustine: A phase I study in Patients with Advanced Progressive Solid Tumors", Journal of Cancer Research and Clinical Oncology, 2000, 126(1), 41-47.

Schrijvers et al., "Phase I study with bendamustine: An update", Seminars in Oncology, Suppl. 13, 2002, 29(4), 15-18.

Strumberg et al., "Bendamustine Hydrochloride Activity against doxorubicin-resistant Human Breast Carcinoma Cell Lines", Anti-Cancer Drugs, 1996, 7(4), 415-421.

Weide et al., "Bendamustine Mitoxantrone and Rituximab (BMR): A New effective regimen for refractory or relapsed indolent lymphomas", Leukemia & Lymphoma, 2002, 43(2), 327-331.

Weide et al., "Bendamustine/ Mitoxantrone/Rituximab (BMR) : A very Effective, well tolerated Outpatient Chemoimmunotherapy for relapsed and refractory CD20-positive Indolent Malignancies Final Results of a Pilot Study", Leukemia & Lymphoma, 2004, 45(12), 2445-2449.

Werner et al., "Hydrolyseprodukte des Cancerostaticums Cytostasan (Bendamustin)", Pharmazie, 1987, 42, 272-273.

Zulkowski et al., "Regression of Brain Metastases from Breast Carcinoma after Chemotherapy with bendamustine", Journal of Cancer Research and Clinical Oncology, 2002, 128(2), 111-113.

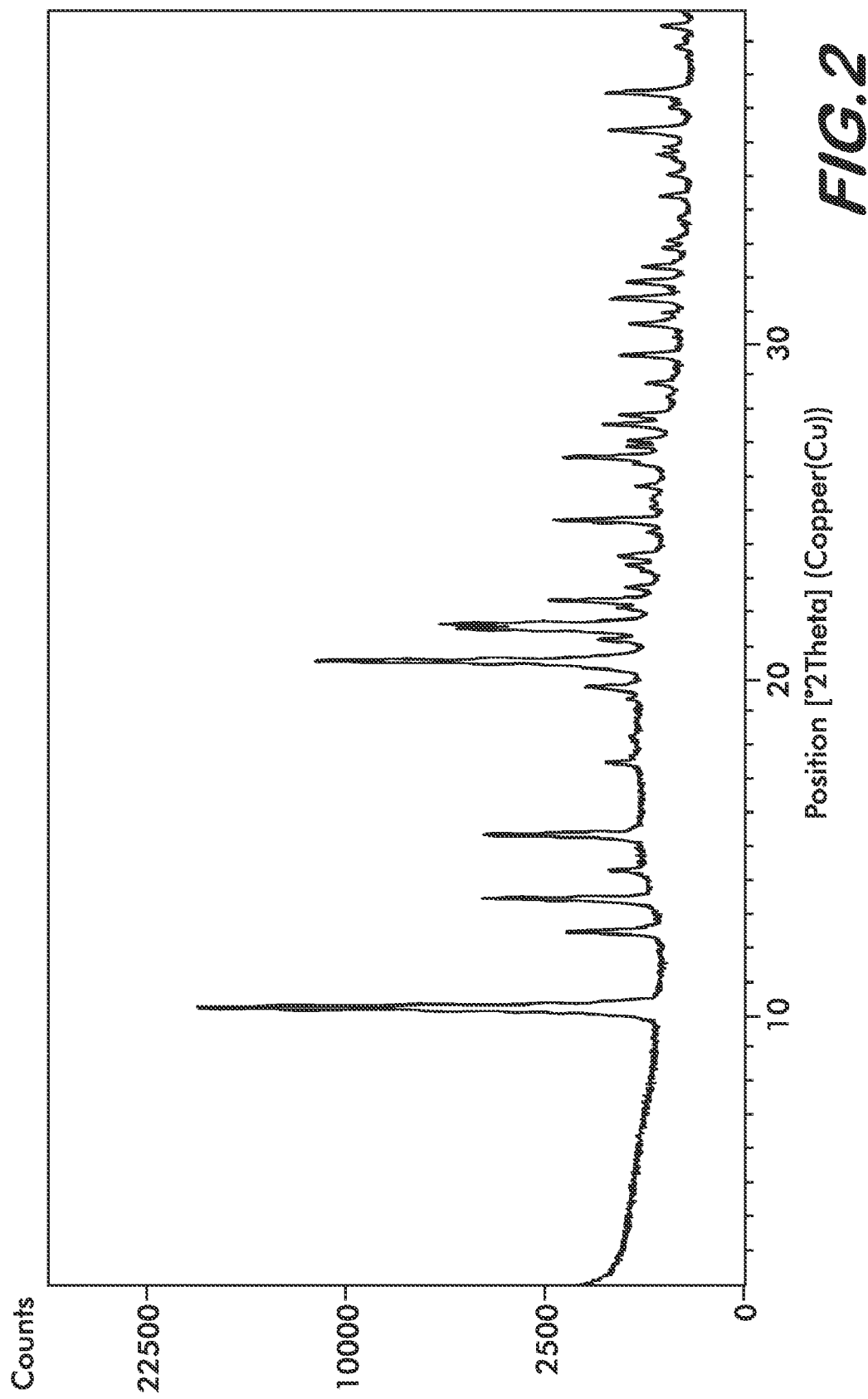

FORMS OF BENDAMUSTINE FREE BASE

FIELD OF THE INVENTION

This invention pertains to bendamustine free base-containing compositions, pharmaceutical compositions comprising bendamustine free base, processes to reproducibly make them, and methods of treating patients using them.

BACKGROUND OF THE INVENTION

Active pharmaceutical ingredients (APIs) can be prepared in a variety of different forms, for example, chemical derivatives, solvates, hydrates, co-crystals, or salts. APIs may also be amorphous, may have different crystalline polymorphs, or may exist in different solvation or hydration states. By varying the form of an API, it is possible to vary the physical properties thereof. For instance, crystalline polymorphs typically have different solubilities such that a more thermodynamically stable polymorph is less soluble than a less thermodynamically stable polymorph. Polymorphs can also differ in properties such as shelf-life, bioavailability, morphology, vapor pressure, density, color, and compressibility. Accordingly, variation of the crystalline state of an API is one of many ways in which to modulate the physical and pharmacological properties thereof.

Bendamustine, 4-{5-[Bis(2-chloroethyl)amino]-1-methyl-2-benzimidazolyl}butyric acid:

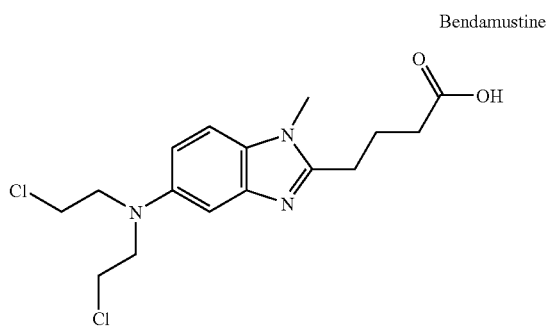

Bendamustine was initially synthesized in 1963 in the German Democratic Republic (GDR) and was available from 1971 to 1992 there, as the hydrochloride salt, under the tradename Cytostasan®. Since that time, it has been marketed in Germany under the tradename Ribomustin®. Ribomustin® is an amorphous, non-crystalline powder. Bendamustine Hydrochloride for injection is available in the United States under the tradename Treanda®.

Bendamustine is an alkylating agent that has been shown to have therapeutic utility in treating diseases such as chronic lymphocytic leukemia, Hodgkin's disease, non-Hodgkin's lymphoma, multiple myeloma, and breast cancer. It is supplied as a lyophilized cake of bendamustine hydrochloride salt Immediately before treatment, the lyophilized cake is dissolved in a pharmaceutically acceptable diluent, preferably Sodium Chloride for Injection.

It is generally desirable that injectable compositions be supplied as the free base form, rather than a salt form, to minimize any side effects that the counterion can produce. Previously described forms of bendamustine free base, however, were unstable and not suitable for commercial preparation, distribution, and administration. As a result, stable forms of bendamustine free base are needed.

SUMMARY OF THE INVENTION

Fifteen novel, crystalline polymorphic forms of bendamustine free base are described herein. Pharmaceutical compositions comprising one or more of the described polymorphic forms of bendamustine free base are also described, as well as pharmaceutical compositions further comprising amorphous bendamustine free base. Methods of using the described forms and compositions for the treatment of leukemia, lymphoma, myeloma, and breast cancer, for example, are also described.

BRIEF DESCRIPTION OF THE DRAWINGS

FIG. 2 is an XRPD spectrum of bendamustine free base Form 2.

DETAILED DESCRIPTION OF ILLUSTRATIVE EMBODIMENTS

Figure 1:
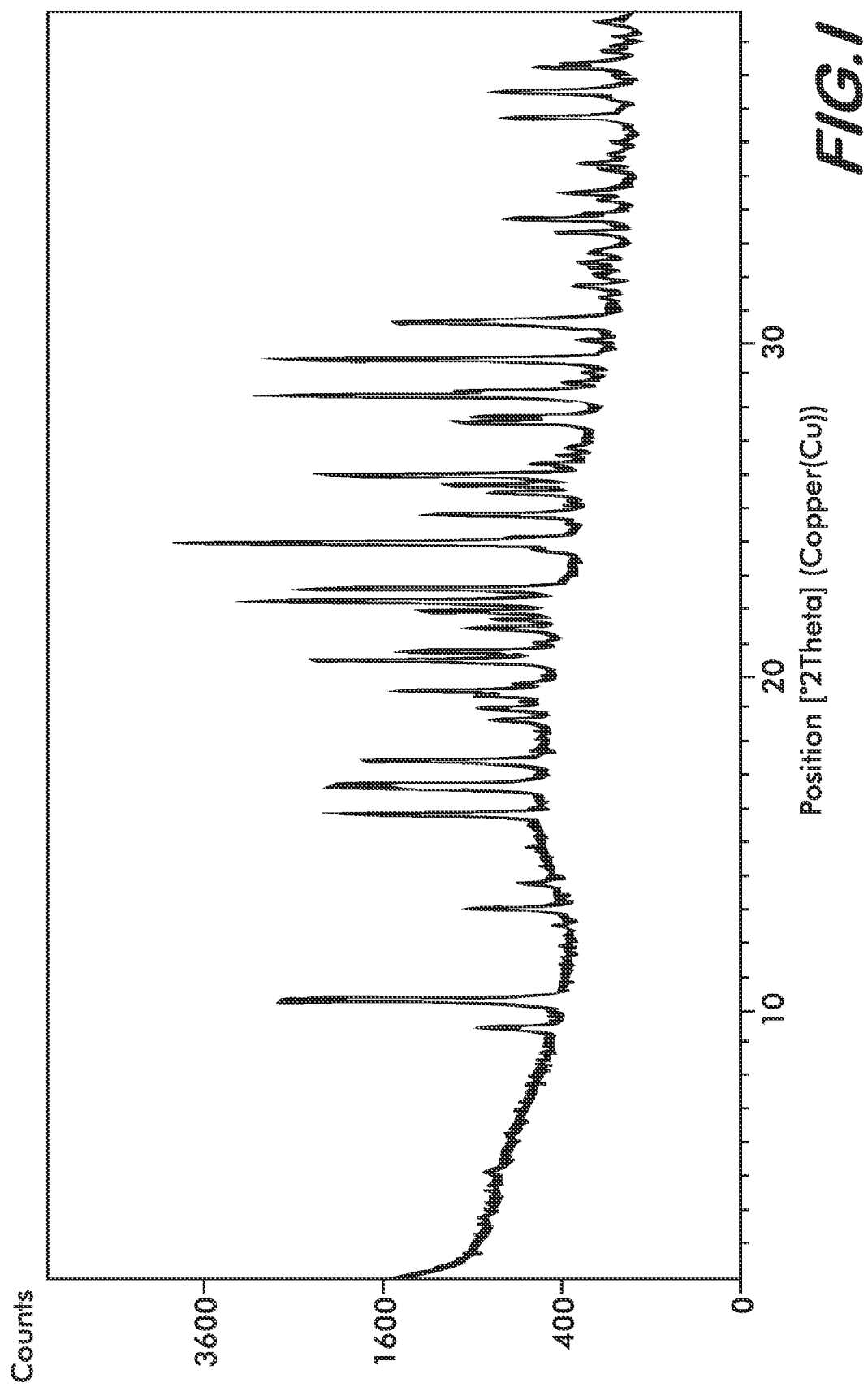
FIG. 1 is an X-Ray Powder Diffractogram (XRPD) spectrum of bendamustine free base Form 1.

Stable forms of bendamustine free base have now been discovered. Six polymorphic forms of anhydrous bendamustine free base are described herein (Form 1, Form 2, Form 4, Form 6, Form 7, Form 10), as well as four hydrate forms (Form 3, Form 5, Form 13, Form 14) and four solvate forms of bendamustine free base (Form 8, Form 9, Form 11, Form 12, Form 15). Amorphous bendamustine free base is also within the scope of the present invention.

In preferred embodiments are crystalline forms of bendamustine free base that are Form 1, Form 2, Form 3, Form 4, Form 5, Form 6, Form 7, Form 8, Form 9, Form 10, Form 11, Form 12, Form 13, Form 14, Form 15, or mixtures thereof. These polymorphs may be identified by X-ray powder diffraction and characterized by one, two, three, four, five or more reflection peaks that are characteristic of each polymorphic form. The 15 crystalline polymorphs (Form 1, Form 2, Form 3, Form 4, Form 5, Form 6, Form 7, Form 8, Form 9, Form 10, Form 11, Form 12, Form 13, Form 14, Form 15) can also be identified by reference to their X-ray powder diffractograms (XRPD), Differential Scanning Calorimetry (DSC) thermograms, Thermogravimetric Analysis (TGA) thermograms, and/or Gravimetric Vapor Sorption (GVS) traces, which are set forth in FIGS. 1-29. Methods of making each polymorph, or a mixture of polymorphs, can be preformed using the techniques described herein.

In another embodiment of the invention are pharmaceutical compositions comprising Form 1, Form 2, Form 3, Form 4, Form 5, Form 6, Form 7, Form 8, Form 9, Form 10, Form 11, Form 12, Form 13, Form 14, Form 15, or mixtures thereof, of bendamustine free base. In other embodiments of the invention are pharmaceutical compositions comprising one or more of Form 1, Form 2, Form 3, Form 4, Form 5, Form 6, Form 7, Form 8, Form 9, Form 10, Form 11, Form 12, Form 13, Form 14, or Form 15 with amorphous (i.e., non-crystalline) bendamustine.

In yet another embodiment of the invention are pharmaceutical compositions comprising Form 1, Form 2, Form 3, Form 4, Form 5, Form 6, Form 7, Form 8, Form 9, Form 10, Form 11, Form 12, Form 13, Form 14, Form 15, or mixtures thereof, of bendamustine free base, and at least one pharmaceutically acceptable excipient or carrier. In other embodiments of the invention are pharmaceutical compositions comprising one or more of Form 1, Form 2, Form 3, Form 4, Form 5, Form 6, Form 7, Form 8, Form 9, Form 10, Form 11, Form 12, Form 13, Form 14, or Form 15 with amorphous (i.e., non-crystalline) bendamustine, and at least one pharmaceutically acceptable excipient or carrier.

Techniques such as thermal analysis (DSC, TGA/MS) and X-ray diffraction are well established for both characterization and quantification of different crystalline forms. It is generally accepted that complementary analytical techniques should be used to properly characterize all different crystalline forms. A series of crystallization experiments were performed in order to explore the effects of solvent, crystallization method and temperature in order to identify and characterize the polymorphs and solvates of bendamustine free base.

Form 1 bendamustine free base can be prepared by slurrying Form 2 bendamustine free base in 2-butanone, acetonitrile, cyclohexane, ethyl acetate, methyl tert-butyl ether, n-butyl acetate, propionitrile, or tetrahydropyran, heating the sample, slow cooling the sample, and isolating the solids. Alternatively, Form 1 bendamustine free base can be prepared by slurrying Form 2 bendamustine free base in 1-butanol, 1,4-dioxane, 1-propanol, acetone, chloroform, cyclohexane, ethanol, methyl isobutyl ketone, methyl tert-butyl ether, n-butyl acetate, propionitrile, tetrahydropyran, or toluene. The sample was slurried for 48 hours with alternating 4 hour periods at 50° C. and 5° C. and the solid isolated. The X-ray diffraction pattern characteristic of the crystalline Form 1 is shown in Table 1 and FIG. 1.

TABLE 1

Most Important Two Theta Positions (2θ), D-spacings (d) and Relative Intensities (I) of XRPD of Form 1

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 9.54 | 9.27 | 12 | 16 | 22.67 | 3.92 | 51 |
| 2 | 10.34 | 8.55 | 62 | 17 | 24.03 | 3.70 | 100 |
| 3 | 10.40 | 8.50 | 45 | 18 | 24.88 | 3.58 | 24 |
| 4 | 13.12 | 6.74 | 12 | 19 | 25.77 | 3.45 | 20 |
| 5 | 15.93 | 5.56 | 43 | 20 | 26.03 | 3.42 | 51 |
| 6 | 16.69 | 5.31 | 45 | 21 | 27.64 | 3.22 | 21 |
| 7 | 16.84 | 5.26 | 36 | 22 | 27.80 | 3.21 | 17 |
| 8 | 17.52 | 5.06 | 33 | 23 | 28.43 | 3.14 | 73 |
| 9 | 19.59 | 4.53 | 30 | 24 | 28.54 | 3.12 | 20 |
| 10 | 20.53 | 4.32 | 49 | 25 | 29.50 | 3.03 | 72 |
| 11 | 20.77 | 4.27 | 29 | 26 | 30.62 | 2.92 | 36 |
| 12 | 20.80 | 4.27 | 25 | 27 | 30.70 | 2.91 | 17 |
| 13 | 21.48 | 4.13 | 15 | 28 | 33.70 | 2.66 | 15 |
| 14 | 21.97 | 4.04 | 25 | 29 | 36.73 | 2.44 | 15 |
| 15 | 22.30 | 3.98 | 71 | 30 | 36.77 | 2.44 | 14 |

Form 2 bendamustine free base can be prepared from bendamustine hydrochloride. Treatment of an aqueous solution of bendamustine hydrochloride with NaOH (1M in water), causes Form 2 bendamustine free base to precipitate and the precipitate can be filtered to isolate Form 2. The X-ray diffraction pattern characteristic of the crystalline Form 2 is shown in Table 2 and FIG. 2.

TABLE 2

Most Important Two Theta Positions (2θ), D-spacings (d) and Relative Intensities (I) of XRPD of Form 2

| No. | Pos. [2θ.] | d-spacing [Å] | Rel. Int. [%] |
|---|---|---|---|
| 1 | 10.28 | 8.60 | 100 |
| 2 | 12.54 | 7.05 | 8 |
| 3 | 13.51 | 6.55 | 21 |
| 4 | 15.40 | 5.75 | 20 |
| 5 | 19.81 | 4.48 | 5 |
| 6 | 20.59 | 4.31 | 60 |
| 7 | 21.55 | 4.12 | 26 |
| 8 | 21.69 | 4.09 | 29 |
| 9 | 22.39 | 3.97 | 11 |
| 10 | 24.78 | 3.59 | 11 |
| 11 | 26.65 | 3.34 | 9 |

TABLE 2-continued

Most Important Two Theta Positions (2θ), D-spacings (d) and Relative Intensities (I) of XRPD of Form 2

| No. | Pos. [2θ.] | d-spacing [Å] | Rel. Int. [%] |
|---|---|---|---|
| 12 | 27.62 | 3.23 | 5 |
| 13 | 31.36 | 2.85 | 5 |
| 14 | 36.38 | 2.47 | 5 |
| 15 | 37.51 | 2.40 | 6 |

Form 3 bendamustine free base can be obtained by the base-mediated hydrolysis of bendamustine ethyl ester. The X-ray diffraction pattern characteristic of the crystalline Form 3 is shown in Table 3 and FIG. 4.

TABLE 3

Most Important Two Theta Positions (2θ), D-spacings (d) and Relative Intensities (I) of XRPD of Form 3

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 4.78 | 18.46 | 5 | 16 | 27.63 | 3.23 | 6 |
| 2 | 9.41 | 9.40 | 100 | 17 | 27.86 | 3.20 | 6 |
| 3 | 9.46 | 9.34 | 88 | 18 | 31.71 | 2.82 | 8 |
| 4 | 14.15 | 6.26 | 30 | | | | |
| 5 | 15.47 | 5.72 | 14 | | | | |
| 6 | 18.78 | 4.72 | 11 | | | | |
| 7 | 19.50 | 4.55 | 14 | | | | |
| 8 | 20.31 | 4.37 | 5 | | | | |
| 9 | 21.24 | 4.18 | 21 | | | | |
| 10 | 22.12 | 4.02 | 15 | | | | |
| 11 | 23.42 | 3.79 | 28 | | | | |
| 12 | 23.65 | 3.76 | 32 | | | | |
| 13 | 24.04 | 3.70 | 10 | | | | |
| 14 | 24.83 | 3.58 | 34 | | | | |
| 15 | 25.79 | 3.45 | 6 | | | | |

Form 4 bendamustine free base can be obtained by exposing Form 3 bendamustine free base to 0% relative humidity. The X-ray diffraction pattern characteristic of the crystalline Form 4 is shown in Table 4 and FIG. 6.

TABLE 4

Most Important Two Theta Positions (2θ), D-spacings (d) and Relative Intensities (I) of XRPD for Form 4

| No. | Pos. [2θ.] | d-spacing [Å] | Rel. Int. [%] |
|---|---|---|---|
| 1 | 9.88 | 8.96 | 100 |
| 2 | 14.88 | 5.95 | 15 |
| 3 | 15.13 | 5.86 | 35 |
| 4 | 18.05 | 4.91 | 6 |
| 5 | 19.44 | 4.57 | 12 |
| 6 | 19.92 | 4.46 | 23 |
| 7 | 20.70 | 4.29 | 7 |
| 8 | 20.91 | 4.25 | 8 |
| 9 | 22.99 | 3.87 | 17 |
| 10 | 24.72 | 3.60 | 35 |
| 11 | 24.98 | 3.56 | 31 |

Form 5 bendamustine free base can be obtained by exposing Form 3 bendamustine free base to about 85% relative humidity for about 1 day. The X-ray diffraction pattern characteristic of the crystalline Form 5 is shown in Table 5 and FIG. 7.

TABLE 5

Most Important Two Theta Positions (2θ), D-spacings (d) and Relative Intensities (I) of XRPD of Form 5

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 8.94 | 9.88 | 100 | 16 | 23.74 | 3.75 | 14 |
| 2 | 12.07 | 7.33 | 5 | 17 | 23.96 | 3.71 | 13 |
| 3 | 13.39 | 6.61 | 71 | 18 | 24.18 | 3.68 | 11 |
| 4 | 14.84 | 5.96 | 8 | 19 | 25.37 | 3.51 | 19 |
| 5 | 16.04 | 5.52 | 58 | 20 | 25.82 | 3.45 | 6 |
| 6 | 16.28 | 5.44 | 8 | 21 | 26.95 | 3.31 | 6 |
| 7 | 17.20 | 5.15 | 5 | 22 | 27.38 | 3.26 | 11 |
| 8 | 17.90 | 4.95 | 44 | 23 | 28.37 | 3.14 | 12 |
| 9 | 18.16 | 4.88 | 13 | 24 | 29.75 | 3.00 | 10 |
| 10 | 19.29 | 4.60 | 29 | 25 | 31.57 | 2.83 | 10 |
| 11 | 20.76 | 4.28 | 12 | 26 | 31.96 | 2.80 | 5 |
| 12 | 21.31 | 4.17 | 49 | 27 | 32.81 | 2.73 | 13 |
| 13 | 21.50 | 4.13 | 16 | | | | |
| 14 | 22.38 | 3.97 | 99 | | | | |
| 15 | 23.41 | 3.80 | 9 | | | | |

Form 6 bendamustine free base can be prepared by slurrying Form 3 bendamustine free base in 1-butanol or 1-propanol, heating the sample, slow cooling the sample, and then isolating the solids. Alternatively, Form 6 bendamustine free base can be prepared by slurrying Form 3 bendamustine free base in 1-butanol, exposing the sample to alternative 4 hour periods at 50° C. and 5° C., and isolating the solids. The X-ray diffraction pattern characteristic of the crystalline Form 6 is shown in Table 6 and FIG. 9.

TABLE 6

Most Important Two Theta Positions (2θ), D-spacings (d) and Relative Intensities (I) of XRPD of Form 6

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 8.67 | 10.19 | 98 | 12 | 26.21 | 3.40 | 42 |
| 2 | 10.29 | 8.59 | 18 | 13 | 27.74 | 3.21 | 44 |
| 3 | 11.48 | 7.70 | 61 | 14 | 28.68 | 3.11 | 41 |
| 4 | 14.23 | 6.22 | 41 | 15 | 29.88 | 2.99 | 16 |
| 5 | 17.23 | 5.14 | 48 | 16 | 31.57 | 2.83 | 18 |
| 6 | 18.15 | 4.88 | 78 | 17 | 34.62 | 2.59 | 40 |
| 7 | 19.40 | 4.57 | 48 | | | | |
| 8 | 20.94 | 4.24 | 60 | | | | |
| 9 | 22.55 | 3.94 | 100 | | | | |
| 10 | 22.95 | 3.87 | 52 | | | | |
| 11 | 25.46 | 3.50 | 98 | | | | |

Form 7 bendamustine free base can be prepared by slurrying Form 3 bendamustine free base in N,N dimethylformamide or isopropyl acetate. The samples were heated, slow cooled, and the solid isolated. Alternatively, Form 7 bendamustine free base can be prepared by slurrying Form 3 bendamustine free base in N,N dimethylformamide, exposing the sample to alternating 4 hour periods at 50° C. and 5° C., and isolating the solids. The X-ray diffraction pattern characteristic of the crystalline Form 7 is shown in Table 7 and FIG. 11.

TABLE 7

Most Important Two Theta Positions (2θ), D-spacings (d) and Relative Intensities (I) of XRPD of Form 7

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 7.06 | 12.51 | 6 | 12 | 22.87 | 3.89 | 13 |
| 2 | 8.51 | 10.39 | 95 | 13 | 23.29 | 3.82 | 36 |
| 3 | 8.56 | 10.32 | 100 | 14 | 24.04 | 3.70 | 24 |
| 4 | 11.42 | 7.74 | 20 | 15 | 25.13 | 3.54 | 7 |
| 5 | 14.23 | 6.22 | 25 | 16 | 27.39 | 3.25 | 12 |
| 6 | 17.10 | 5.18 | 13 | 17 | 28.09 | 3.17 | 17 |
| 7 | 17.62 | 5.03 | 17 | 18 | 28.94 | 3.08 | 18 |
| 8 | 17.97 | 4.93 | 25 | 19 | 32.33 | 2.77 | 14 |
| 9 | 20.53 | 4.32 | 10 | 20 | 34.50 | 2.60 | 16 |
| 10 | 21.25 | 4.18 | 49 | 21 | 36.31 | 2.47 | 20 |
| 11 | 22.08 | 4.02 | 13 | | | | |

Form 8 bendamustine free base can be prepared by slurrying Form 3 bendamustine free base in ethanol, exposing the sample to alternating 4 hour periods at 50° C. and 5° C., and isolating the solids. The X-ray diffraction pattern characteristic of the crystalline Form 8 is shown in Table 8 and FIG. 13.

TABLE 8

Most Important Two Theta Positions (2θ), D-spacings (d) and Relative Intensities (I) of XRPD of Form 8

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 5.25 | 16.82 | 9 | 16 | 23.33 | 3.81 | 5 |
| 2 | 8.60 | 10.27 | 5 | 17 | 23.88 | 3.72 | 6 |
| 3 | 9.34 | 9.46 | 12 | 18 | 24.36 | 3.65 | 8 |
| 4 | 10.45 | 8.46 | 45 | 19 | 24.98 | 3.56 | 95 |
| 5 | 11.17 | 7.91 | 58 | 20 | 25.56 | 3.48 | 7 |
| 6 | 13.97 | 6.34 | 9 | 21 | 26.40 | 3.37 | 67 |
| 7 | 15.32 | 5.78 | 60 | 22 | 27.58 | 3.23 | 16 |
| 8 | 15.72 | 5.63 | 35 | 23 | 30.87 | 2.89 | 20 |
| 9 | 16.25 | 5.45 | 5 | 24 | 35.31 | 2.54 | 12 |
| 10 | 17.16 | 5.16 | 9 | | | | |
| 11 | 20.22 | 4.39 | 9 | | | | |
| 12 | 21.01 | 4.23 | 34 | | | | |
| 13 | 21.30 | 4.17 | 31 | | | | |
| 14 | 21.88 | 4.06 | 10 | | | | |
| 15 | 22.48 | 3.95 | 100 | | | | |

Form 9 bendamustine free base can be prepared by heating Form 2 bendamustine free base in 3-pentanone, slow cooling the sample, and isolating the solids. The X-ray diffraction pattern characteristic of the crystalline Form 9 is shown in Table 9 and FIG. 15.

TABLE 9

Most Important Two Theta Positions (2θ), D-spacings (d) and Relative Intensities (I) of XRPD of Form 9

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 4.44 | 19.88 | 28 | 16 | 21.89 | 4.06 | 14 |
| 2 | 8.88 | 9.95 | 22 | 17 | 22.32 | 3.98 | 100 |
| 3 | 9.13 | 9.68 | 28 | 18 | 22.66 | 3.92 | 25 |
| 4 | 12.67 | 6.98 | 15 | 19 | 22.98 | 3.87 | 29 |
| 5 | 13.34 | 6.63 | 44 | 20 | 23.45 | 3.79 | 27 |
| 6 | 16.56 | 5.35 | 32 | 21 | 23.69 | 3.75 | 18 |
| 7 | 16.73 | 5.30 | 64 | 22 | 24.80 | 3.59 | 24 |
| 8 | 17.50 | 5.06 | 5 | 23 | 25.92 | 3.43 | 9 |
| 9 | 17.82 | 4.97 | 23 | 24 | 26.28 | 3.39 | 17 |
| 10 | 18.31 | 4.84 | 13 | 25 | 26.80 | 3.32 | 11 |
| 11 | 19.15 | 4.63 | 14 | 26 | 29.26 | 3.05 | 5 |
| 12 | 19.33 | 4.59 | 18 | 27 | 30.71 | 2.91 | 8 |
| 13 | 19.54 | 4.54 | 43 | 28 | 31.38 | 2.85 | 13 |
| 14 | 20.36 | 4.36 | 10 | 29 | 31.64 | 2.83 | 9 |
| 15 | 20.90 | 4.25 | 8 | 30 | 36.09 | 2.49 | 10 |

Form 10 bendamustine free base can be prepared by heating Form 2 bendamustine free base in toluene, slow cooling the sample, and isolating the solids. The X-ray diffraction pattern characteristic of the crystalline Form 10 is shown in Table 10 and FIG. 17.

TABLE 10

Most Important Two Theta Positions (2θ), D-spacings (d) and Relative Intensities (I) of XRPD of Form 10

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 9.76 | 9.05 | 11 | 16 | 22.87 | 3.89 | 50 |
| 2 | 10.59 | 8.34 | 14 | 17 | 24.03 | 3.70 | 51 |
| 3 | 16.13 | 5.49 | 35 | 18 | 24.24 | 3.67 | 100 |
| 4 | 16.82 | 5.27 | 65 | 19 | 25.08 | 3.55 | 9 |
| 5 | 16.93 | 5.23 | 85 | 20 | 25.75 | 3.46 | 23 |
| 6 | 17.06 | 5.19 | 44 | 21 | 26.27 | 3.39 | 17 |
| 7 | 17.72 | 5.00 | 13 | 22 | 26.58 | 3.35 | 12 |
| 8 | 18.90 | 4.69 | 15 | 23 | 27.85 | 3.20 | 29 |
| 9 | 19.31 | 4.59 | 13 | 24 | 28.03 | 3.18 | 18 |
| 10 | 19.68 | 4.51 | 51 | 25 | 28.63 | 3.12 | 32 |
| 11 | 19.83 | 4.47 | 41 | 26 | 29.72 | 3.00 | 37 |
| 12 | 20.72 | 4.28 | 26 | 27 | 30.70 | 2.91 | 26 |
| 13 | 21.67 | 4.10 | 17 | 28 | 30.82 | 2.90 | 26 |
| 14 | 22.14 | 4.01 | 35 | 29 | 33.90 | 2.64 | 18 |
| 15 | 22.51 | 3.95 | 22 | 30 | 37.71 | 2.38 | 17 |

Form 11 bendamustine free base can be prepared by slurrying Form 3 bendamustine free base in 1-butanol, 1,4-dioxane, or isopropyl acetate at ambient temperature for about 48 hours and isolating the solids. The X-ray diffraction pattern characteristic of the crystalline Form 11 is shown in Table 11 and FIG. 19.

TABLE 11

Most Important Two Theta Positions (2θ), D-spacings (d) and Relative Intensities (I) of XRPD of Form 11

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 4.64 | 19.02 | 10 | 16 | 22.36 | 3.97 | 100 |
| 2 | 8.90 | 9.93 | 86 | 17 | 23.33 | 3.81 | 73 |
| 3 | 9.28 | 9.52 | 94 | 18 | 24.02 | 3.70 | 7 |
| 4 | 13.36 | 6.62 | 59 | 19 | 24.72 | 3.60 | 20 |
| 5 | 13.94 | 6.35 | 87 | 20 | 25.38 | 3.51 | 24 |
| 6 | 15.11 | 5.86 | 7 | 21 | 25.79 | 3.45 | 10 |
| 7 | 16.01 | 5.53 | 39 | 22 | 26.05 | 3.42 | 10 |
| 8 | 17.15 | 5.17 | 5 | 23 | 26.92 | 3.31 | 7 |
| 9 | 17.86 | 4.96 | 33 | 24 | 27.36 | 3.26 | 8 |
| 10 | 18.22 | 4.86 | 11 | 25 | 28.38 | 3.14 | 14 |
| 11 | 18.59 | 4.77 | 8 | 26 | 29.71 | 3.00 | 9 |
| 12 | 19.30 | 4.59 | 26 | 27 | 31.53 | 2.84 | 11 |

TABLE 11-continued

Most Important Two Theta Positions (2θ), D-spacings
(d) and Relative Intensities (I) of XRPD of Form 11

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 13 | 20.03 | 4.43 | 5 | 28 | 32.77 | 2.73 | 18 |
| 14 | 20.76 | 4.28 | 13 | | | | |
| 15 | 21.29 | 4.17 | 51 | | | | |

Form 12 bendamustine free base can be prepared by slurrying Form 3 bendamustine free base in N,N dimethylformamide at ambient temperature for about 48 hours and isolating the solids. The X-ray diffraction pattern characteristic of the crystalline Form 12 is shown in Table 12 and FIG. 21.

TABLE 12

Most Important Two Theta Positions (2θ), D-spacings
(d) and Relative Intensities (I) of XRPD of Form 12

| No. | Pos. [2θ.] | d-spacing [Å] | Rel. Int. [%] |
|---|---|---|---|
| 1 | 4.71 | 18.76 | 10 |
| 2 | 8.57 | 10.31 | 5 |
| 3 | 9.31 | 9.49 | 99 |
| 4 | 9.35 | 9.45 | 87 |
| 5 | 13.97 | 6.33 | 100 |
| 6 | 14.03 | 6.31 | 82 |
| 7 | 18.68 | 4.75 | 9 |
| 8 | 20.79 | 4.27 | 5 |
| 9 | 21.14 | 4.20 | 9 |
| 10 | 22.20 | 4.00 | 5 |
| 11 | 22.80 | 3.90 | 5 |
| 12 | 23.38 | 3.80 | 80 |
| 13 | 24.75 | 3.59 | 11 |
| 14 | 25.39 | 3.51 | 6 |
| 15 | 26.06 | 3.42 | 7 |

Form 13 can be prepared by heating Form 3 bendamustine free base in methyl tert-butyl ether or 3-pentanone, slow cooling the sample, and isolating the solids. The X-ray diffraction pattern characteristic of the crystalline Form 13 is shown in Table 13 and FIG. 23.

TABLE 13

Most Important Two Theta Positions (2θ), D-spacings
(d) and Relative Intensities (I) of XRPD of Form 13

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 4.99 | 17.68 | 6 | 16 | 25.17 | 3.54 | 12 |
| 2 | 9.84 | 8.98 | 85 | 17 | 26.02 | 3.42 | 11 |
| 3 | 12.51 | 7.07 | 18 | 18 | 26.91 | 3.31 | 20 |
| 4 | 12.85 | 6.89 | 34 | 19 | 27.36 | 3.26 | 5 |
| 5 | 14.76 | 6.00 | 100 | 20 | 28.30 | 3.15 | 13 |
| 6 | 15.38 | 5.76 | 5 | 21 | 28.71 | 3.11 | 6 |
| 7 | 16.89 | 5.25 | 8 | 22 | 29.81 | 2.99 | 11 |
| 8 | 17.29 | 5.12 | 6 | 23 | 30.79 | 2.90 | 18 |
| 9 | 19.67 | 4.51 | 76 | 24 | 37.06 | 2.42 | 5 |
| 10 | 20.32 | 4.37 | 9 | | | | |
| 11 | 21.35 | 4.16 | 22 | | | | |
| 12 | 21.67 | 4.10 | 14 | | | | |
| 13 | 22.21 | 4.00 | 20 | | | | |
| 14 | 23.20 | 3.83 | 19 | | | | |
| 15 | 24.62 | 3.61 | 40 | | | | |

Form 14 bendamustine free base can be prepared by slurrying Form 3 bendamustine free base in acetonitrile at ambient temperature for about 48 hours and isolating the solids. The X-ray diffraction pattern characteristic of the crystalline Form 14 is shown in Table 14 and FIG. 25.

TABLE 14

Most Important Two Theta Positions (2θ), D-spacings
(d) and Relative Intensities (I) of XRPD of Form 14

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 8.74 | 10.11 | 74 | 16 | 27.16 | 3.28 | 18 |
| 2 | 9.14 | 9.67 | 70 | 17 | 28.15 | 3.17 | 7 |
| 3 | 11.89 | 7.44 | 7 | 18 | 29.57 | 3.02 | 11 |
| 4 | 13.20 | 6.70 | 44 | 19 | 31.44 | 2.84 | 18 |
| 5 | 13.68 | 6.47 | 45 | 20 | 32.59 | 2.75 | 19 |
| 6 | 14.69 | 6.02 | 20 | | | | |
| 7 | 15.85 | 5.59 | 50 | | | | |
| 8 | 17.72 | 5.00 | 45 | | | | |
| 9 | 19.19 | 4.62 | 70 | | | | |
| 10 | 21.13 | 4.20 | 100 | | | | |
| 11 | 22.10 | 4.02 | 88 | | | | |
| 12 | 23.12 | 3.84 | 79 | | | | |
| 13 | 23.61 | 3.76 | 36 | | | | |
| 14 | 24.59 | 3.62 | 25 | | | | |
| 15 | 25.28 | 3.52 | 31 | | | | |

Form 15 bendamustine free base can be prepared by recrystallization of Form 1 bendamustine free base in tetrahydrofuran and isolating the solids. The X-ray diffraction pattern characteristic of the crystalline Form 15 is shown in Table 15 and FIG. 27.

TABLE 15

Most Important Two Theta Positions (2θ), D-spacings
(d) and Relative Intensities (I) of XRPD of Form 15

| No. | Pos. [2θ.] | d-spacing [Å] | Rel. Int. [%] | No. | Pos. [2θ] | d-spacing [Å] | Rel. Int. [%] |
|---|---|---|---|---|---|---|---|
| 1 | 4.09 | 21.60 | 59 | 16 | 29.43 | 3.03 | 17 |
| 2 | 8.10 | 10.91 | 63 | | | | |
| 3 | 10.26 | 8.62 | 38 | | | | |
| 4 | 12.15 | 7.28 | 5 | | | | |
| 5 | 16.46 | 5.38 | 6 | | | | |
| 6 | 17.36 | 5.11 | 9 | | | | |
| 7 | 17.96 | 4.94 | 10 | | | | |
| 8 | 19.92 | 4.46 | 28 | | | | |
| 9 | 20.58 | 4.32 | 14 | | | | |
| 10 | 22.19 | 4.01 | 37 | | | | |
| 11 | 23.83 | 3.73 | 27 | | | | |
| 12 | 24.56 | 3.62 | 100 | | | | |
| 13 | 26.01 | 3.43 | 25 | | | | |
| 14 | 26.83 | 3.32 | 16 | | | | |
| 15 | 28.39 | 3.14 | 30 | | | | |

Also within the scope of the invention are pharmaceutical compositions comprising amorphous, non-crystalline bendamustine free base. The bendamustine free base may be provided as compositions consisting primarily of an amorphous form of bendamustine free base or as compositions comprising amorphous bendamustine free base as well as at least one crystalline form, such as crystalline bendamustine free base Form 1, Form 2, Form 3, Form 4, Form 5, Form 6, Form 7, Form 8, Form 9, Form 10, Form 11, Form 12, Form 13, Form 14, Form 15, or mixtures thereof.

In preferred embodiments, pharmaceutical compositions comprising at least one of Form 1, Form 2, Form 3, Form 4, Form 5, Form 6, Form 7, Form 8, Form 9, Form 10, Form 11, Form 12, Form 13, Form 14, or Form 15, and optionally, amorphous bendamustine free base, as well as at least one pharmaceutically acceptable excipient, are provided. Pharmaceutically acceptable excipients are known in the art and include those described in, for example, U.S. application Ser. No. 11/267,010. These pharmaceutical compositions may be prepared as injectables, either as liquid solutions or suspensions, as well as solid forms, for example, capsules, tablets, lozenges, pastilles, powders, suspensions, and the like.

In preferred embodiments, the pharmaceutical compositions are sublimed, preferably freeze-dried or lyophilized, compositions. In other embodiments, methods of preparing such sublimed, preferably freeze-dried or lyophilized, preparations of bendamustine free base that contain Form 1, Form 2, Form 3, Form 4, Form 5, Form 6, Form 7, Form 8, Form 9, Form 10, Form 11, Form 12, Form 13, Form 14, Form 15, or a mixture thereof, are provided Lyophilization involves the addition of water to a compound, followed by freezing of the resultant suspension or solution, and sublimation of the water from the compound. In preferred embodiments, at least one organic solvent is added to the suspension/solution. In other preferred embodiments, the suspension/solution further comprises a lyophilization excipient. The lyophilized preparations of bendamustine free base of the present invention may further comprise amorphous bendamustine free base.

In a typical lyophilization procedure, water, a pharmaceutically acceptable lyophilizing excipient, an organic solvent, and bendamustine free base are combined, preferably under sterile conditions, to form a solution. Preferably, the solution is prepared and sterilized by filtration. This solution is then lyophilized using standard, sterile lyophilization equipment.

While preferred embodiments of the present invention include lyophilization of bendamustine free base, it is envisioned that other sublimation techniques may also be used. For example, one or more of the described forms of bendamustine free base may be dissolved, dispersed or suspended in a solvent, the resulting mixture (be it a solution, dispersion or suspension) frozen, and the solvent removed by sublimation.

A lyophilization excipient can be any pharmaceutically acceptable excipient that, when used during the lyophilization process, results in a lyophilzed product that has improved properties, for example, improved handling properties, solubility properties, and the like. A lyophilization excipient can be, for example, a bulking agent; suitable bulking agents are known in the art. Examples of suitable lyophilization excipients include, for example, sodium phosphate, potassium phosphate, citric acid, tartaric acid, gelatin, glycine, mannitol, lactose, sucrose, maltose, glycerin, dextrose, dextran, trehalose, hetastarch, or mixtures thereof. A lyophilization excipient may also comprise a pharmaceutically acceptable antioxidant, such as, for example, ascorbic acid, acetylcysteine, cysteine, sodium hydrogen sulfite, butyl-hydroxylanisole, butyl-hydroxytoluene, or alpha-tocopherol acetate. A preferred lyophilization excipient is mannitol.

Solvents for use in the present invention include water and organic solvents that form stable solutions with bendamustine free base without appreciably degrading the bendamustine, and which are capable of being removed through lyophilization. Examples of suitable organic solvents include, for example, methanol, ethanol, n-propanol, iso-propanol, n-butanol, tert-butanol, or mixtures thereof. A preferred organic solvent is tert-butanol.

Also within the scope of the invention are methods of treating diseases, such as, for example, chronic lymphocytic leukemia, Hodgkin's disease, non-Hodgkin's lymphoma, multiple myeloma, or breast cancer, with a pharmaceutical composition of the present invention. In certain embodiments, the method comprises administering a therapeutically effective amount of a pharmaceutical composition of the present invention directly to the patient. In other embodiments, the method comprises modifying a pharmaceutical composition of the present invention before administration, such as by dissolving the composition in water or another solvent prior to administration. In these embodiments, the method comprises administering to the patient a therapeutically effective amount of a preparation prepared from a pharmaceutical composition of the present invention. Preferably, the preparation is an injectable preparation. The injectable preparation may be administered subcutaneously, intracutaneously, intravenously, intramuscularly, intra-articularly, intrasynovially, intrasternally, intrathecally, intralesionally, intracranially or via infusion. Other conditions amenable to treatment utilizing the compositions and injectable preparations of the present invention include small cell lung cancer, hyperproliferative disorders, and autoimmune diseases, such as rheumatoid arthritis, multiple sclerosis, and lupus.

The injectable preparations described herein are in the form of a sterile injectable preparation, for example, as a sterile, injectable aqueous or oleaginous suspension formulated according to techniques known in the art. Typically, the pharmaceutical compositions of the present invention, containing at least one of Form 1, Form 2, Form 3, Form 4, Form 5, Form 6, Form 7, Form 8, Form 9, Form 10, Form 11, Form 12, Form 13, Form 14, Form 15, or amorphous bendamustine free base, are formulated as lyophilized powders which may be provided, for example, in vials containing 100 mg of drug per 50 mL vial. The injectable preparation may be prepared by reconstitution of a freeze-dried or lyophilized composition with Sterile Water for Injection and then further dilution with a pharmaceutically acceptable intravenous solution, such as, for example, 0.9% sodium Chloride, 5% dextrose in water (D5W), Lactated Ringers solution, or 0.45% Sodium Chloride/2.5% dextrose.

Preferably, the pharmaceutical compositions of bendamustine free base described herein are reconstituted into an injectable preparation, for example, with sterile water, in less than about 20 minutes. More preferably, reconstitution occurs in less than about 10 minutes, most preferably about 5 minutes.

A typical reconstitution process would include reconstituting, preferably aseptically, 100 mg bendamustine free base with 20 mL Sterile Water for Injection. This yields a clear, colorless to pale yellow solution having a bendamustine concentration of 5 mg/mL. If lyophilized bendamustine free base is being reconstituted, the bendamustine free base should completely dissolve in about 5 minutes. The volume needed for the required dose (based on 5 mg/mL concentration) can be aseptically withdrawn and transferred to a 500 mL infusion bag of 0.9% Sodium Chloride (or other pharmaceutically acceptable intravenous solution) for injection. Preferably, the reconstituted solution is transferred to the infusion bag within 30 minutes of reconstitution. After transfer, the contents of the infusion bag are thoroughly mixed. Administration by intravenous infusion is typically provided over a time period of from about 30 to about 60 minutes.

It is envisioned that the pharmaceutical compositions of the present invention can be administered in combination with one or more anti-neoplastic agents where the anti-neoplastic agent is given prior to, concurrently with, or subsequent to the administration of the composition of the present invention. Pharmaceutically acceptable anti-neoplastic agents are known in the art. Preferred anti-neoplastic agents are those disclosed in co-pending U.S. application Ser. No. 11/330, 868, filed Jan. 12, 2006, the entirety of which is incorporated herein by reference.

Therapeutically effective amounts of bendamustine can be readily determined by an attending diagnostician by use of conventional techniques. The effective dose can vary depending upon a number of factors, including type and extent of progression of the disease or disorder, overall health of a particular patient, biological efficacy of the bendamustine, formulation of the bendamustine, and route of administration of the forms of bendamustine. Bendamustine can also be administered at lower dosage levels with gradual increases until the desired effect is achieved.

Terminology

"Polymorphism," as used herein, is defined as the occurrence of different crystalline arrangements for the same molecules. A "solvate," as used herein, is a crystalline material that contains solvent molecules, for example, water, ethanol, 3-pentanone, ethyl acetate, dichloromethane, diethyl ether, and the like, within the crystal structure. The term "solvent," as used herein, means a substance, typically a liquid, that is capable of completely or partially dissolving another substance, typically a solid. The following solvents were used in the experiments described herein:

| | |
|---|---|
| 1-butanol | Heptane |
| 1,4-dioxane | Isopropyl acetate |
| 1-propanol | Methanol |
| 2-butanone | Methyl isobutyl ketone |
| 3-pentanone | Methyl tert-butyl ether |
| Acetone | N,N-dimethylformamide |
| Acetonitrile | N-butyl acetate |
| Chloroform | Propanonitrile |
| Cyclohexane | Tetrahydrofuran |
| Dichloromethane | Tetrahydropyran |
| Ethanol | Toluene |
| Ethyl acetate | Water |

The term "crystalline," as used herein, means having a regularly repeating arrangement of molecules or external face planes. "Non-crystalline," as used herein, refers to amorphous material having no detectable regularly repeating arrangement of molecules or external face planes.

The term "crystalline composition," as used in herein, refers to a solid chemical compound or mixture of compounds that provides a characteristic pattern of peaks when analyzed by x-ray powder diffraction; this includes, but is not limited to, polymorphs, solvates, hydrates, co-crystals, and desolvated solvates.

The term "isolating" as used herein, means separating a compound from a solvent to provide a solid, semisolid or syrup. This is typically accomplished by means such as centrifugation, filtration with or without vacuum, filtration under positive pressure, distillation, evaporation or a combination thereof. Isolating may or may not be accompanied by purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

The term "pharmaceutically acceptable excipient," as used herein, includes any and all solvents, dispersion media, coatings, antibacterial and antifungal agents, isotonic and absorption delaying agents and the like, acceptable for pharmaceutical use, for example, those that have been accorded Generally Regarded as Safe (GRAS) status by the U.S. Food and Drug Administration. The use of such media and agents for pharmaceutical active substances is well known in the art, such as in Remington: The Science and Practice of Pharmacy, 20th ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

The term "solution," as used herein, refers to a mixture containing at least one solvent and at least one compound that is at least partially dissolved in the solvent.

The term "sublimation," as used herein, refers to the transition from the solid phase to the gas phase with no intermediate liquid stage.

The term "substantially free," as used herein with regard to compositions that contain a particular form of bendamustine while being "substantially free" of other forms of the compound, means that the recited form is associated with less than 10%, preferably less than 5%, in particular less than 2% and most preferably less than 1% of the other recited forms of bendamustine.

The term "therapeutically effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

Experimental Section

Instrumentation

X-Ray Powder Diffraction

PANalytical X Pert Pro

Powder X-Ray Diffraction patterns were recorded on a PANalytical X Pert Pro diffractometer equipped with an X celerator detector using Cu Kα radiation at 40 kV and 40 mA. Kα1 radiation is obtained with a highly oriented crystal (Ge111) incident beam monochromator. A 10 mm beam mask, and fixed (¼°) divergence and anti-scatter (⅛°) slits were inserted on the incident beam side. A fixed 0.10 mm receiving slit was inserted on the diffracted beam side. The X-ray powder pattern scan was collected from ca. 2 to 40° 2θ with a 0.0080° step size and 96.06 sec counting time which resulted in a scan rate of approximately 0.5°/min. The samples were spread on silicon zero background (ZBG) plate for the measurement. The sample was rotated at 4°/min on a PANalytical PW3064 Spinner. Measurement of the Si reference standard before the data collection resulted in values for 2θ and intensity that were well within the tolerances of 28.44<2θ<28.50 and significantly greater than the minimum peak height of 150 cps.

Bruker AXS/Siemens D5000

X-Ray Powder Diffraction patterns were collected on a Siemens D5000 diffractometer using Cu Kα radiation (40 kV, 40 mA), 600 nm goniometer, automatic divergence and receiving slits, a graphite secondary monochromator and a scintillation counter. The instrument is performance checked using a certified corundum standard (NIST 1976).

Ambient Conditions

Samples run under ambient conditions were prepared as flat plate specimens using powder as received. Approximately 35 mg of the sample was gently packed into a cavity cut into polished, zero-background (510) silicon wafer and a MYLAR® cover was placed over the sample. The sample was rotated in its own plane during analysis.

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for autosample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 5 mm. A 0-0 continuous scan mode was employed with a sample-detector distance of 20 cm which gives an effective 2θ range of 3.2°-29.7°. Typically, the sample would be exposed to the X-ray beam for 120 seconds.

Ambient Conditions

Samples run under ambient conditions were prepared as flat plate specimens using powder as received without grinding. Approximately 1-2 mg of the sample was lightly pressed on a glass slide to obtain a flat surface.

Variable Temperature X-Ray Powder Diffraction (VT-XRPD)

Variable temperature studies were performed with an Anton Paar TTK450 temperature chamber under computer control through an Anton Paar TCU100 temperature control unit. Typically, the measurements were done with a nitrogen flow through the camera. Two measurement schemes were used, restricted and continuous. In the restricted mode, measurements were made only after the TK450 chamber reached the requested temperature. In the continuous mode, the sample was heated at 10° C./minute and fast scans were measured as the temperature changed. After the pre-selected temperature was reached, the sample was cooled at 35° C./minute. To monitor for changes during the cooling, fast scans were again measured. At 25° C., a slow scan was measured. The temperatures chosen were based on DSC results. For the diffractometer set-up a 10 mm beam mask, 0.04 radian Soller slits and fixed (¼°) divergence and anti-scatter (⅛°) slits were inserted on the incident beam side. A fixed 0.10 mm receiving slit, 0.04 radian Soller slits and a 0.02 mm Nickel filter were inserted on the diffracted beam side. The slow scans were collected from ca. 3 to 30° 2θ with a 0.0080° step size and 100.97 sec counting time which resulted in a scan rate of approximately 0.5°/min. The fast scans were collected from ca. 3 to 30° 2θ with a 0.0167° step size and 1.905 sec counting time which resulted in a scan rate of approximately 44°/min. With the nitrogen gas supply turned off, the camera returned to ambient conditions. The humidity in the ambient state varies with the humidity in the laboratory, typically 30 to 40%, and with the temperature in the camera. As the temperature is raised, the relative humidity will drop.

Differential Scanning Calorimetry (DSC)

Thermal curves were acquired using a Perkin-Elmer Sapphire DSC unit equipped with an autosampler running Pyris software version 6.0 calibrated with Indium prior to analysis. Solid samples of 1-11 mg were weighed into 20 μL aluminum open samples pans. The DSC cell was then purged with nitrogen and the temperature heated from 0° to 275° C. at 10° C./min.

Thermogravimetric Mass Spectrometry—(TGA/MS)

Thermal curves were acquired using a Perkin-Elmer Pyris 1 TGA unit running Pyris software version 6.0 calibrated with calcium oxalate monohydrate. TGA samples between 1-5 mg were monitored for percent weight loss as heated from 25° to 300° C. at 10° C./min in a furnace purged with Helium at ca. 50 mL/min. To simultaneously follow the evolution of the gaseous decomposition products over the temperature range investigated, the thermobalance was connected to a Thermo-Star Mass Spectrometer (Asslar, Germany). The transfer line to introduce gaseous decomposition products into the mass spectrometer was a deactivated fused silica capillary temperature controlled to 200° C. to avoid possible condensation of the evolved gases. In this way the thermogravimetric (TG) and mass spectrometric ion intensity curves of the selected ionic species could be recorded simultaneously.

Thermogravimetric Analysis—(TGA)

TGA data were collected on a TA Instruments Q500 TGA, equipped with a 16 position autosampler. The instrument was temperature calibrated using certified Alumel. Typically 1-2 mg of each sample was loaded into a pin-holed hermetically sealed aluminium DSC pan on a pre-tared platinum crucible, and was heated at 10° C. min−1 from ambient temperature to 200° C. A nitrogen purge at 60 ml.min−1 was maintained over the sample. The instrument control software was Thermal Advantage v4.6.6 and the data were analyzed using Universal Analysis v4.3A.

$^1$H NMR

1H NMR spectra were collected on a Bruker 400 MHz instrument equipped with an auto-sampler and controlled by a DRX400 console. Automated experiments were acquired using ICON-NMR v4.0.4 (build 1) running with Topspin v 1.3 (patch level 6) using the standard Bruker loaded experiments. For non-routine spectroscopy, data were acquired through the use of Topspin alone. Samples were prepared in $d_6$-DMSO, unless otherwise stated. Off-line analysis was carried out using ACD SpecManager v 9.09 (build 7703).

Polymorph Screening

Crystallizations studies were performed on bendamustine free base to investigate polymorphism in 24 different solvents. Solvents were selected on the basis of acceptability (ICH Class 3 and 2) and to give a range of dielectric constants, dipole moments and functional groups. Maturation, slow cool and slurry crystallization were also employed to obtain different forms of the bendamustine free base. When possible, full characterization was performed on the new forms that were generated during the polymorphism screening on bendamustine free base. This characterization consisted of: X-ray powder diffraction; thermal analysis; GVS; and purity by HPLC.

Crystallization by Maturation Experiments

Approximately 40 mg of bendamustine free base (Form 2 bendamustine free base or Form 3 bendamustine free base) in 800 μL of solvent (25 volumes) was slurried in the 24 diverse solvents. These mixtures were slurried for 48 hours with alternating 4 hour periods at 50° C. and 5° C. (−0.5° C./min). The solid material was isolated by filtration and analyzed by XRPD and thermal analysis. The material was dried at 40° C. during 3 hour. Results are shown in Table 16 and Table 17 below.

TABLE 16

| Maturation with Form 3 | |
| --- | --- |
| Solvent | XRPD Status |
| 1-butanol | Form 6 |
| 1-propanol | Form 13 |
| 3-pentanone | Form 13 |

TABLE 16-continued

Maturation with Form 3

| Solvent | XRPD Status |
|---|---|
| Chloroform | Form 13 |
| Cyclohexane | Form 3 |
| Dichloromethane | Form 3 |
| Ethanol | Form 8 |
| Heptane | Form 3 |
| Methyl tert-butyl ether | Form 13 |
| N,N-dimethylformamide | Form 7 |
| Tetrahydropyran | Form 3 |
| Toluene | Form 3 |
| Water | No crystallization |

TABLE 17

Maturation with Form 2

| Solvent | XRPD Status |
|---|---|
| 1-butanol | Form 1 |
| 1,4-dioxane | Form 1 |
| 1-propanol | Form 1 |
| Acetone | Form 1 |
| Chloroform | Form 1 |
| Cyclohexane | Form 1 |
| Ethanol | Form 1 |
| Heptane | Form 2 |
| Methyl isobutyl ketone | Form 1 |
| Methyl tert-butyl ether | Form 1 |
| N-butyl acetate | Form 1 |
| Propanonitrile | Form 1 |
| Tetrahydropyran | Form 1 |
| Toluene | Form 1 |

Crystallization by Slow Cool

Approximately 40 mg of bendamustine free base (Form 2 or Form 3) in 800 μL of solvent (25 volumes) were slurried in the 24 diverse solvents. The samples were heated from 20° C. to 80° C. at a rate of 4.8° C./min and after 30 minutes cooled at a slow rate (0.25° C./min) to a final temperature of 5° C. and kept at that temperature for 18 h. The solid material from each vial was isolated by filtration and evaluated by XRPD and thermal analysis. The material was dried at 40° C. during 3 hour. Results are shown in Table 18 and Table 19 below.

TABLE 18

Slow Cool with Form 3

| Solvent | XRPD Status |
|---|---|
| 1-butanol | Form 6 |
| 1-propanol | Form 6 |
| Isopropyl acetate | Form 7 |
| N,N-dimethylformamide | Form 7 |
| Toluene | Form 3 |

TABLE 19

Slow Cool with Form 2

| Solvent | XRPD Status |
|---|---|
| 2-butanone | Form 1 |
| 3-pentanone | Form 9 |
| Acetonitrile | Form 1 |
| Cyclohexane | Form 1 |
| Ethyl acetate | Form 1 |
| Methyl tert-butyl ether | Form 1 |

TABLE 19-continued

Slow Cool with Form 2

| Solvent | XRPD Status |
|---|---|
| N-butyl acetate | Form 1 |
| Propanonitrile | Form 1 |
| Tetrahydropyran | Form 1 |
| Toluene | Form 10 |

Crystallization by Slurry Experiments

The slurries (40 mg of bendamustine free base in 400 μL) were shaken at 25° C. during 48 hours. The solid was isolated by filtration and dried at 40° C. during 3 hours. The XRPD results from the isolated solid are recorded in Table 20.

TABLE 20

Slurry Experiments with Form 3

| Solvent | XRPD Status |
|---|---|
| 1-butanol | Form 11 |
| 1,4-dioxane | Form 11 |
| 2-butanone | Form 3 |
| 3-pentanone | Form 3 |
| Acetone | Form 3 |
| Acetonitrile | Form 7 |
| Chloroform | Form 3 |
| Cyclohexane | Form 3 |
| Dichloromethane | Form 3 |
| Ethyl acetate | Form 3 |
| Isopropyl acetate | Form 11 |
| Methyl isobutyl ketone | Form 3 |
| Methyl tert-butyl ether | Form 3 |
| N,N-dimethylformamide | Form 12 |
| N-butyl acetate | Form 3 |
| Propanonitrile | Form 3 |
| Tetrahydropyran | Form 3 |
| Toluene | Form 3 |

Form 1

Preparation

Slow Cool Experiments

Approximately 40 mg of Form 2 bendamustine free base in 800 μL of solvent (20 volumes) were slurried in 2-butanone, acetonitrile, cyclohexane, ethyl acetate, methyl tert-butyl ether, n-butyl acetate, propionitrile and tetrahydrypyran. The samples were heated from 20° C. to 80° C. at a rate of 4.8° C./min and after 30 minutes cooled at a slow rate (0.25° C./min) to a final temperature of 5° C. and kept at that temperature for 18 h. The solid material was isolated by filtration and dried at 40° C. over 3 hours. The material was analyzed by XRPD and thermal analysis.

Crystallization by Maturation Experiments

Approximately 40 mg of Form 2 bendamustine free base in 800 μL of solvent (20 volumes) were slurried in 1-butanol, 1-4 dioxane, 1-propanol, acetone, chloroform, cyclohexane, ethanol, methyl isobutyl ketone, methyl tert-butyl ether, n-butyl acetate, propionitrile, tetrahydropyran and toluene. These mixtures were slurried for 48 hours with alternating 4 hour periods at 50° C. and 5° C. (−0.5° C./min) The solid material was isolated by filtration and dried at 40° C. over 3 hours. The material was analyzed by XRPD and thermal analysis.

The X-ray diffraction pattern characteristic of the crystalline Form 1 is shown in Table 1 (above) and FIG. 1.

Characterization of Form 1 by Thermal Analysis

Figure 1A:
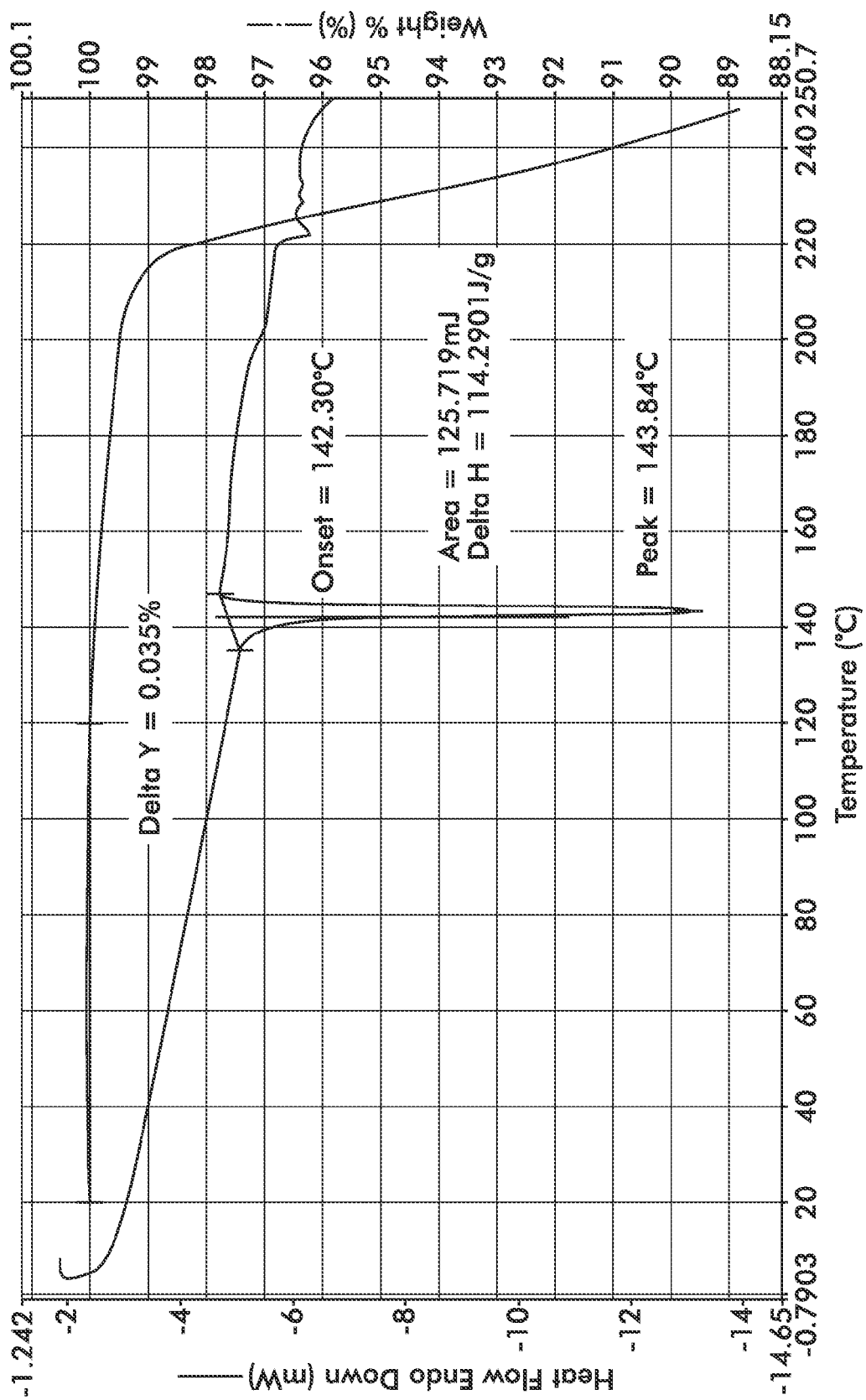
FIG. 1A Differential Scanning Calorimetry/Thermogravimetric Analysis (DSC/TGA) Overlay Data for Form 1.

Form 1 shows a single peak at ca. 142.3° C. with an enthalpy of fusion ($\Delta H_{Fus}$) of 114.3 J/g. No loss of mass is detected by TGA. The existence of a desolvation process was discounted because no loss of weight was detected by TGA (FIG. 1A).

Form 2

Preparation

Slow Cool Experiments 1.08 g of Bendamustine Hydrochloride was dissolved in 100 mL of deionised water. One mole equivalent of NaOH (1 molar in water) was added drop-wise causing precipitation to occur. Solid was then rapidly isolated by filtration and washed on the filter with 2 portions of deionised water and 2 portions of heptane to remove excess water. The solid was dried under vacuum at ambient temperature for 18 hours. 752 mg of solid was obtained and analyzed by XRPD.

The X-ray diffraction pattern characteristic of the crystalline Form 2 is shown in Table 2 (above) and FIG. 2.

Characterization of Form 2 by Thermal Analysis

Figure 3:
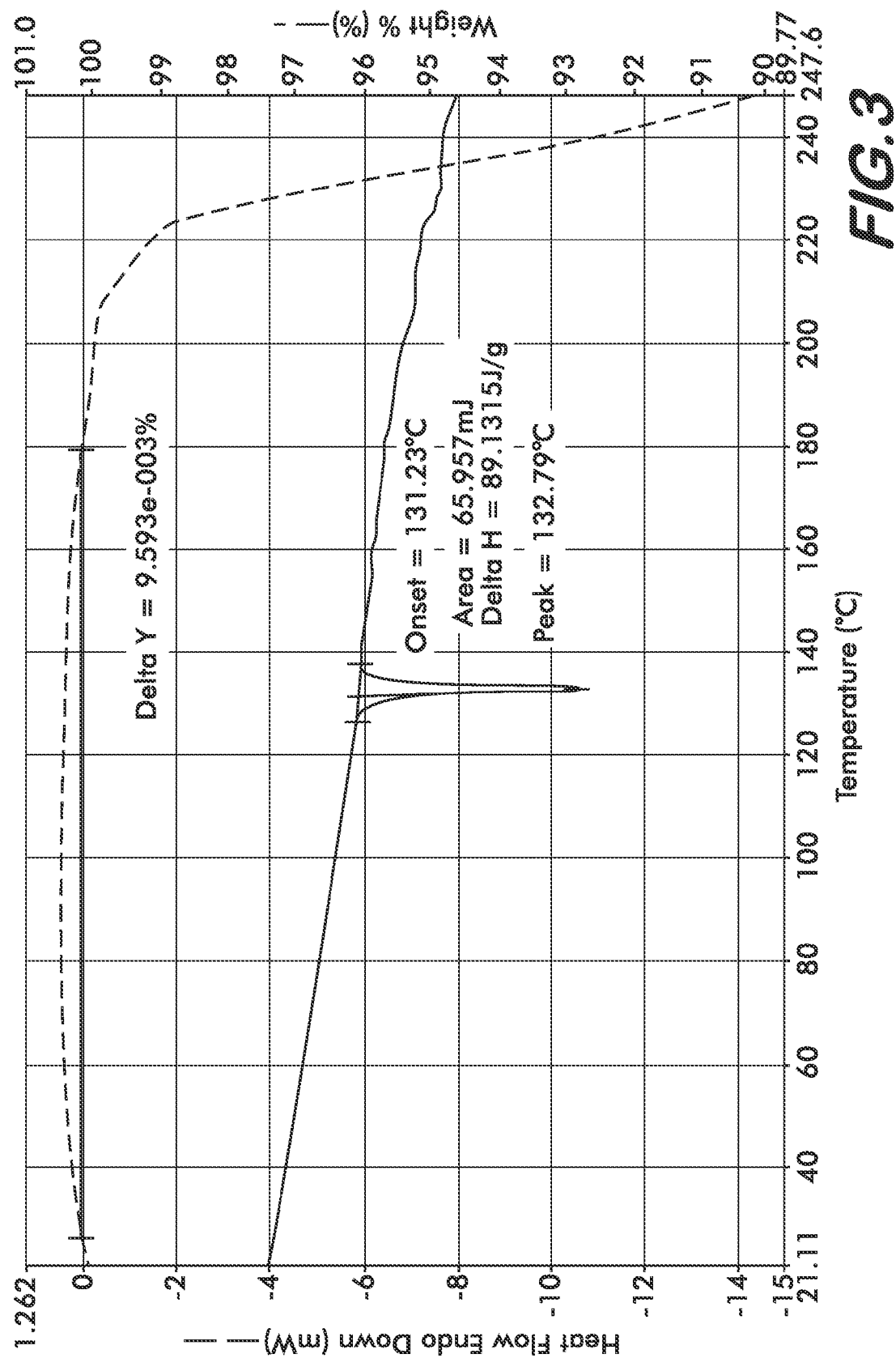
FIG. 3 is an overlay of the DSC/TGA data for bendamustine free base Form 2.

Form 2 bendamustine free base shows a single peak at ca. 132.8° C. with an enthalpy of fusion ($\Delta H_{Fus}$) of 89.1 J/g. No loss of mass is detected by TGA. The existence of a desolvation process was discounted because no loss of weight was detected by TGA (FIG. 3)

Form 3

Preparation

Slow Cool Experiments

Bendamustine free base was prepared by the base-mediated hydrolysis of the ethyl ester of bendamustine. After the hydrolysis was completed, the reaction mixture was neutralized by aqueous hydrochloric acid. Around pH 6-7, the product, precipitating as a solid, was collected by filtration and washed by water. The crude product was triturated by a mixture of acetone (20 ml) and Methyl tert-butyl ether (5 ml). Following filtration, the solid was dried at 60° C.

Figure 4:
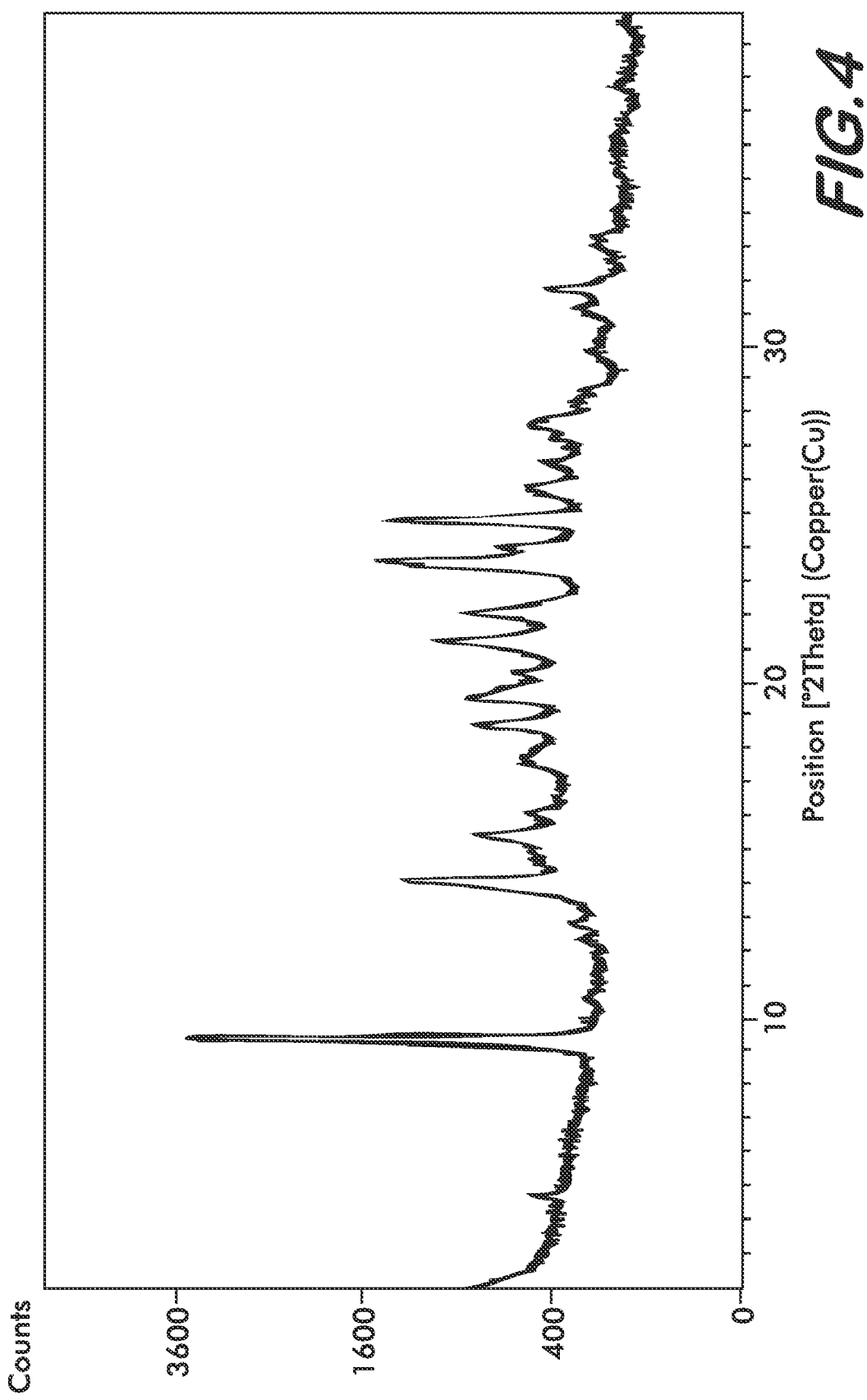
FIG. 4 is an XRPD spectrum of bendamustine free base Form 3.

The X-ray diffraction pattern characteristic of the crystalline Form 3 is shown in Table 3 (above) and FIG. 4.

Characterization of Form 3 by Thermal Analysis

Figure 5:
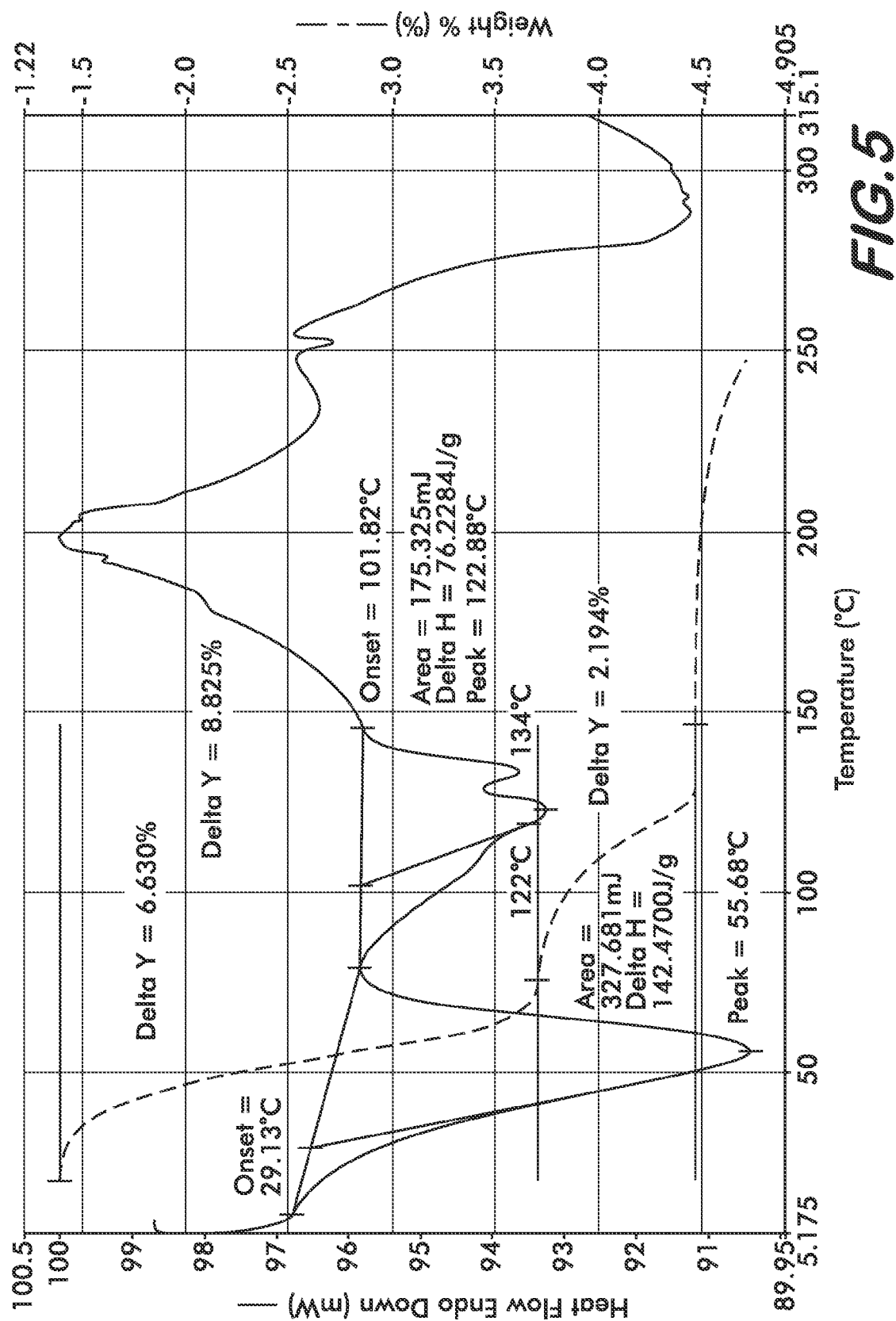
FIG. 5 is an overlay of the DSC/TGA data for bendamustine free base Form 3.
Figure 23:
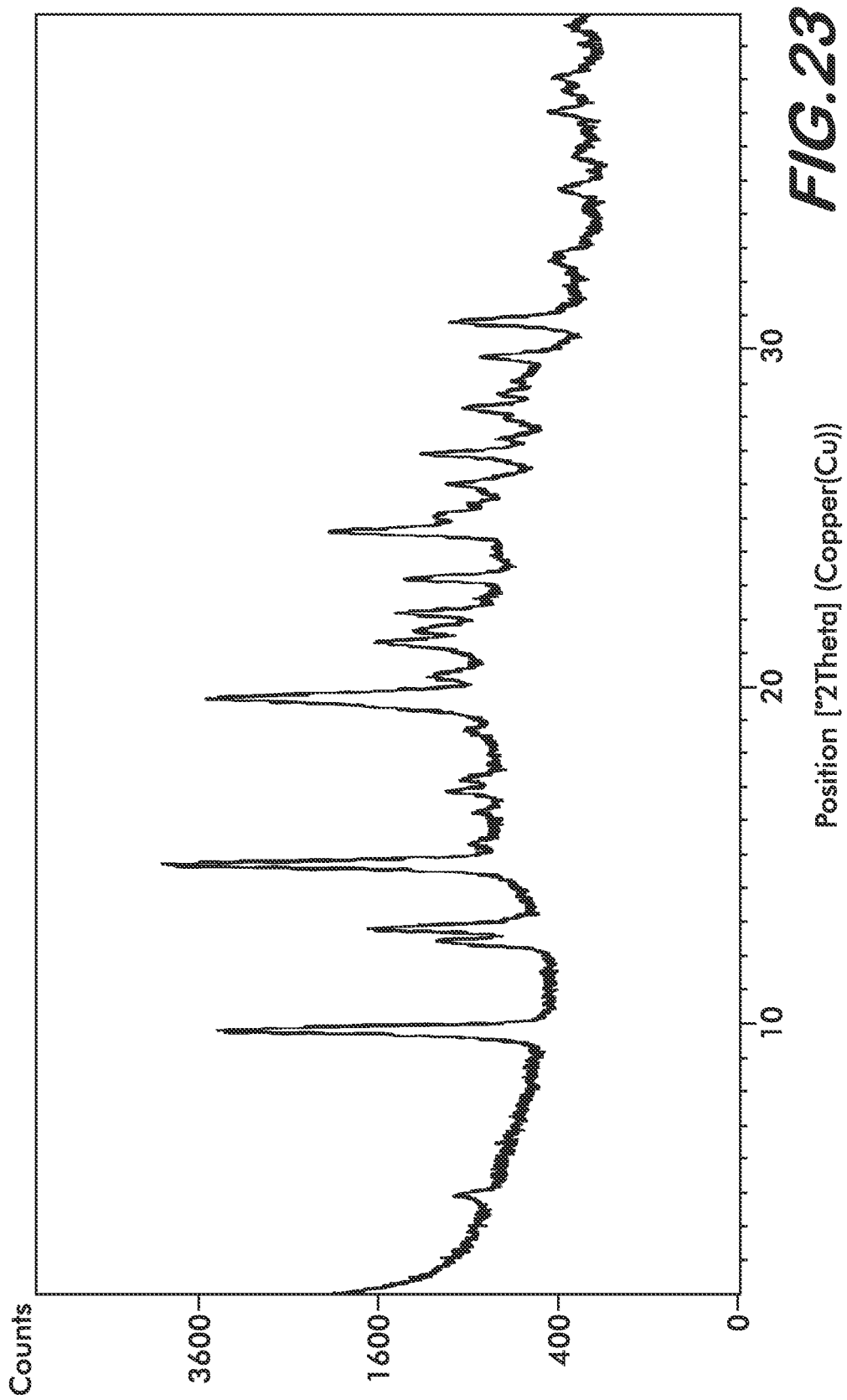
FIG. 23 is an XRPD spectrum of bendamustine free base Form 13.

Form 3 shows a multiple onset at ca. 29.1 and 101.8 with an enthalpy of fusion ($\Delta H_{Fus}$) of 142.5 and 76.2 J/g (FIG. 23). TGA experiment loses an average weight of 8.8% between 20 and 150° C. The theoretical value for incorporation of two moles of water with one mole of bendamustine free base is 9.1% (FIG. 5).

Form 4

Preparation by Solid-Solid Transition

Approximately 100 mg of Form 3 bendamustine free base was exposed to 0% RH at 25° C. during 30 minutes. The X-ray diffraction pattern characteristic of the crystalline Form 4 is shown in Table 4 (above) and FIG. 6.

Form 5

Preparation by Solid-Solid Transition

Approximately 100 mg of Form 3 bendamustine free base was exposed to 85% RH at 25° C. during 1 day. The X-ray diffraction pattern characteristic of the crystalline Form 5 is shown in Table 5 (above) and FIG. 7.

Characterization of Form 5 by Thermal Analysis

Figure 8:
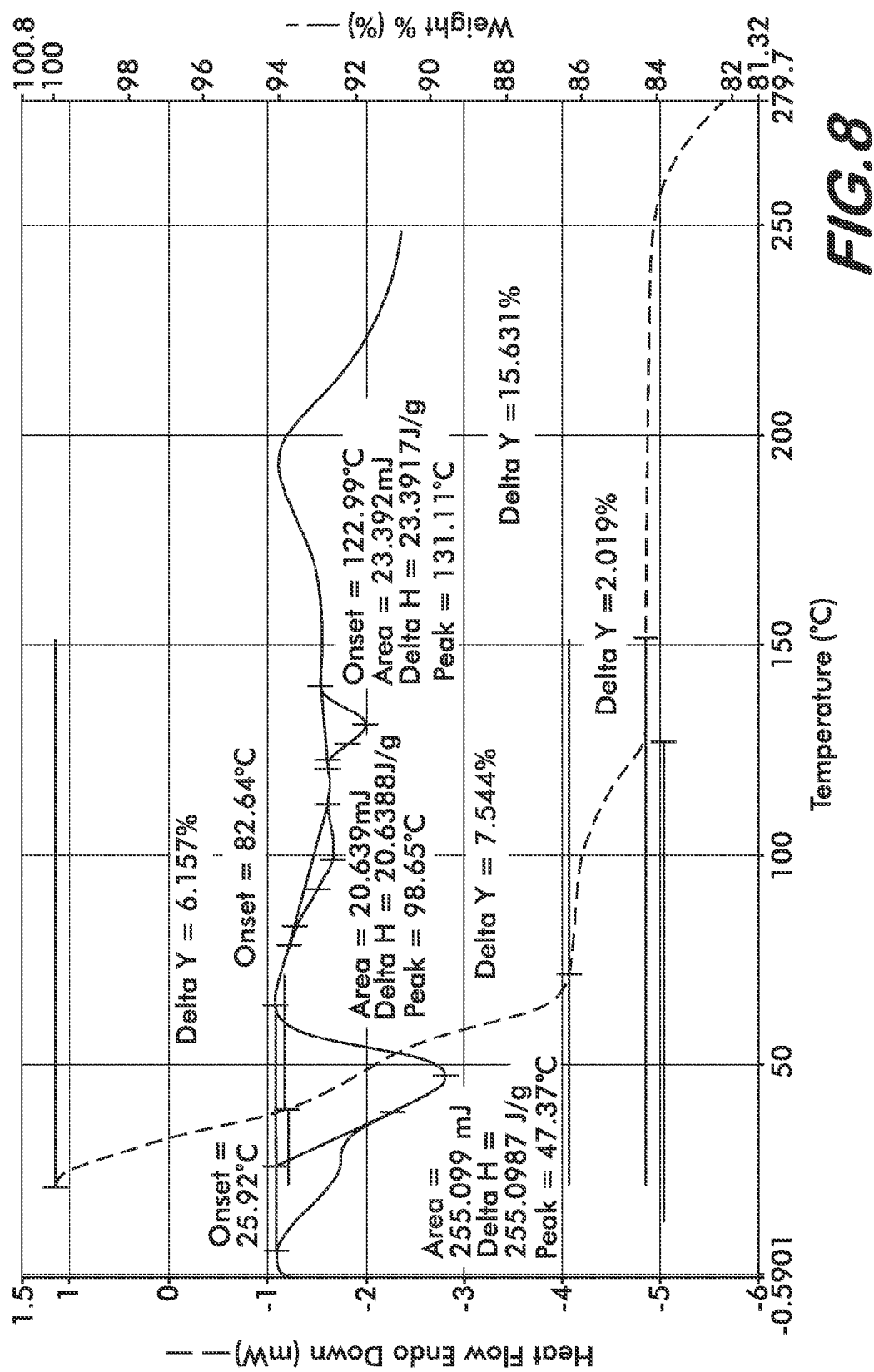
FIG. 8 is an overlay of the DSC/TGA data for bendamustine free base Form 5.

Form 5 shows a multiple onset at ca. 25.9, 82.6 and 123.0 with an enthalpy of fusion ($\Delta H_{Fus}$) of 255.1, 20.6 and 23.4 J/g (FIG. 23). TGA experiment loses an average weight of 15.6% between 20 and 150° C. The theoretical value for incorporation of four moles of water with one mole of bendamustine free base is 16.7% (FIG. 8).

Form 6

Preparation

Slow Cool Experiments

Approximately 40 mg of Form 3 bendamustine free base in 800 µL of solvent (20 volumes) was slurried in the 1-butanol or 1-propanol. The samples were heated from 20° C. to 80° C. at a rate of 4.8° C./min and after 30 minutes cooled at a slow rate (0.25° C./min) to a final temperature of 5° C. and kept at that temperature for 18 h. The solid material was isolated by filtration and dried at 40° C. over 3 hours. The material was analyzed by XRPD and thermal analysis.

Crystallization by Maturation Experiments

Approximately 40 mg of Form 3 bendamustine free base in 800 µL of solvent (20 volumes) were slurried in 1-butanol. The mixtures was slurried for 48 hours with alternating 4 hour periods at 50° C. and 5° C. (−0.5° C./min) The solid material was isolated by filtration and dried at 40° C. over 3 hours. The material was analyzed by XRPD and thermal analysis.

Figure 9:
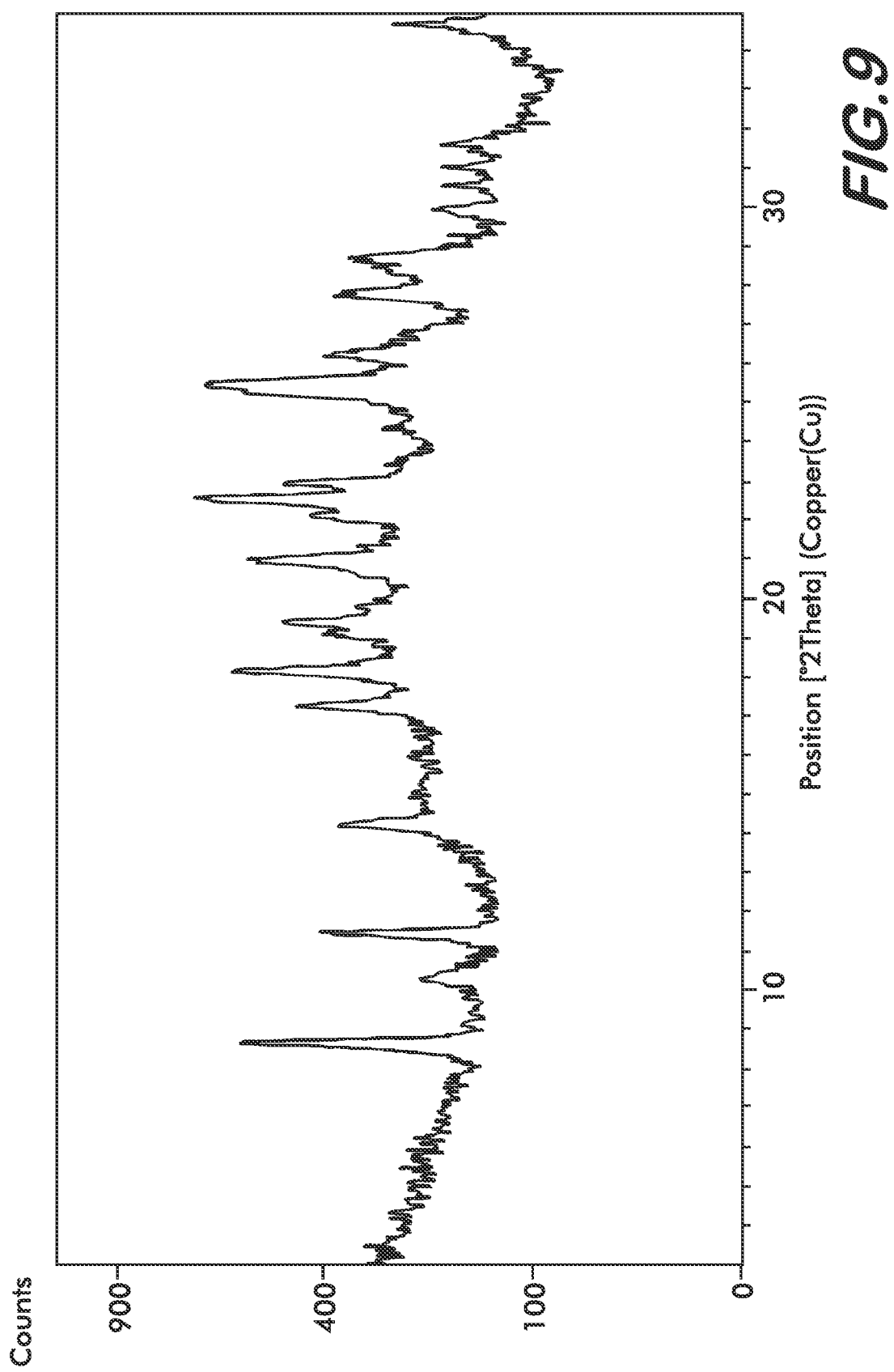
FIG. 9 is an XRPD spectrum of bendamustine free base Form 6.

The X-ray diffraction pattern characteristic of the crystalline Form 6 is shown in Table 6 (above) and FIG. 9.

Characterization of Form 6 by Thermal Analysis

Figure 10:
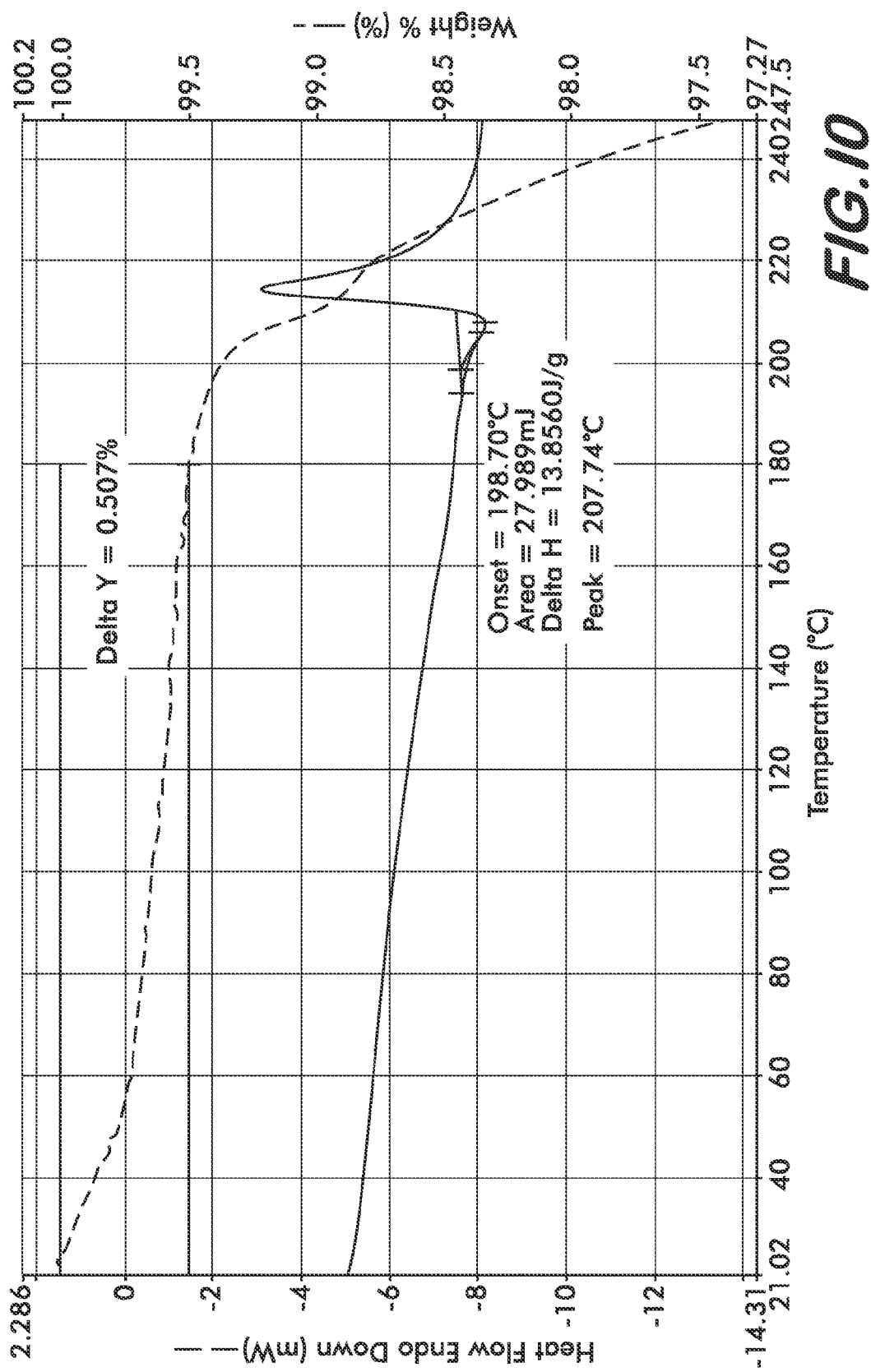
FIG. 10 is an overlay of the DSC/TGA data for bendamustine free base Form 6

Form 6 shows a single onset at ca. 207.8° C. with an enthalpy of fusion ($\Delta H_{Fus}$) of 28.0 J/g. No loss of mass is detected by TGA. The existence of a desolvation process was discounted because no loss of weight was detected by TGA (FIG. 10).

Form 7

Preparation

Slow Cool Experiments

Approximately 40 mg of Form 3 bendamustine free base in 800 µL of solvent (20 volumes) were slurried in N,N dimethylformamide or isopropyl acetate. The samples were heated from 20° C. to 80° C. at a rate of 4.8° C./min and after 30 minutes cooled at a slow rate (0.25° C./min) to a final temperature of 5° C. and kept at that temperature for 18 h. The solid material was isolated by filtration and dried at 40° C. over 3 hours. The material was analyzed by XRPD and thermal analysis.

Crystallization by Maturation Experiments

Approximately 40 mg of Form 3 bendamustine free base in 800 µL of solvent (20 volumes) were slurried in N,N dimethylformamide. These mixtures were slurried for 48 hours with alternating 4 hour periods at 50° C. and 5° C. (−0.5° C./min) The solid material was isolated by filtration and dried at 40° C. over 3 hours. The material was analyzed by XRPD and thermal analysis.

Figure 11:
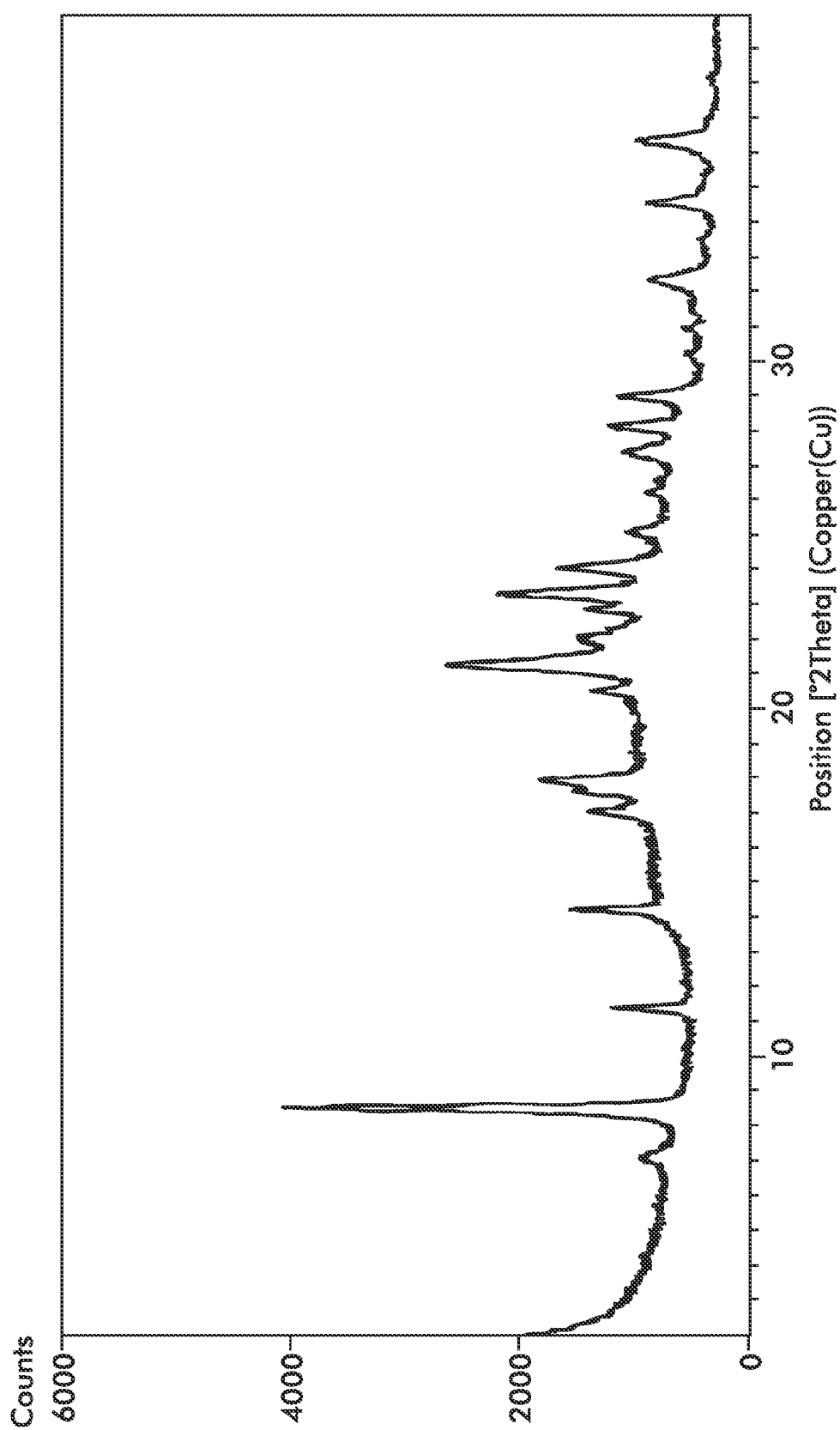
FIG. 11 is an XRPD spectrum of bendamustine free base Form 7.

The X-ray diffraction pattern characteristic of the crystalline Form 7 is shown in Table 7 (above) and FIG. 11.

Characterization of Form 7 by Thermal Analysis

Figure 12:
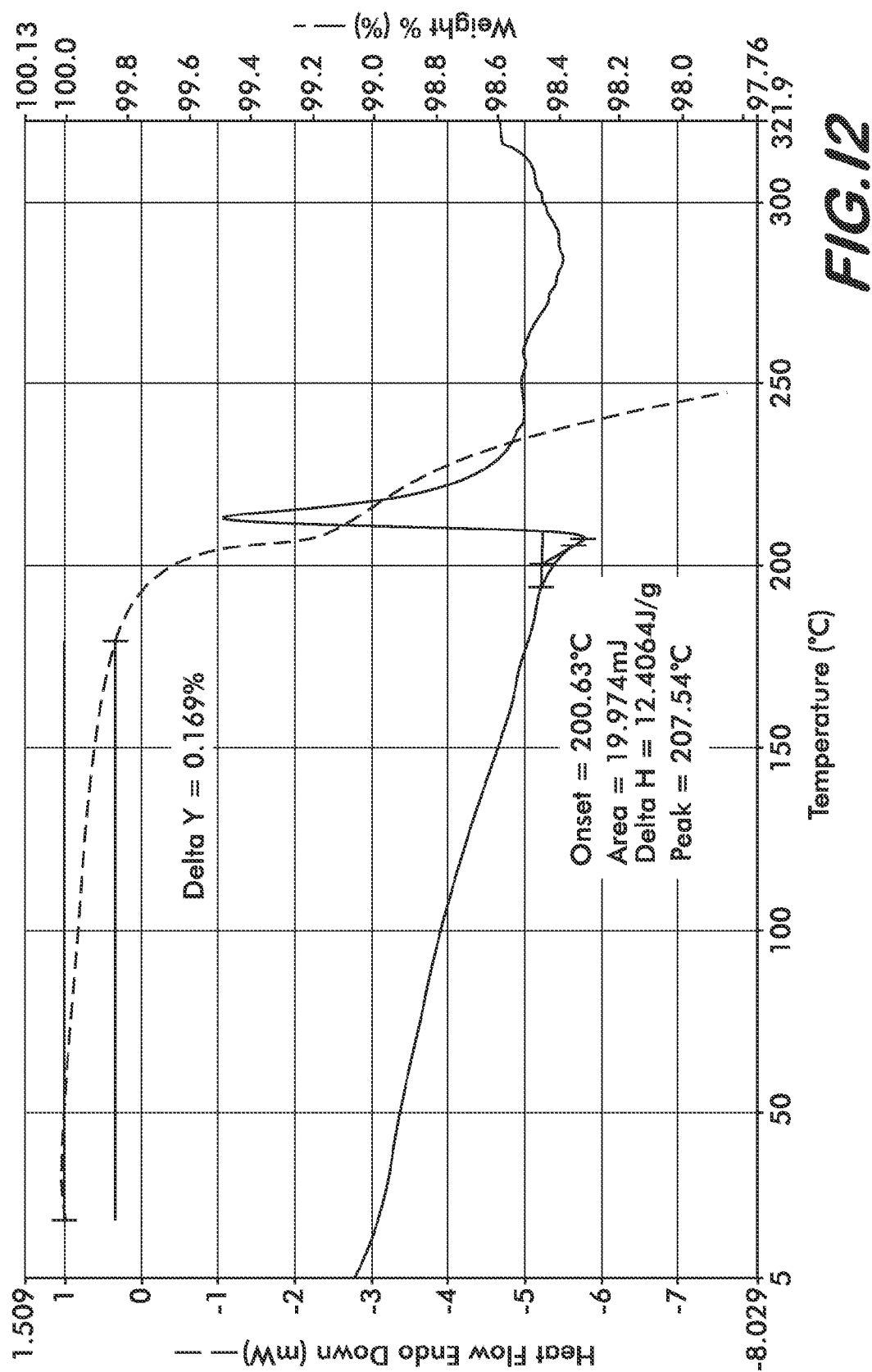
FIG. 12 is an overlay of the DSC/TGA data for bendamustine free base Form 7.

Form 7 shows a single onset at ca. 200.6° C. with an enthalpy of fusion ($\Delta H_{Fus}$) of 12.7 J/g. No loss of mass is detected by TGA. The existence of a desolvation process was discounted because no loss of weight was detected by TGA (FIG. 12).

Form 8

Preparation

Crystallization by Maturation Experiments

Approximately 40 mg of Form 3 bendamustine free base was added in 800 µL of ethanol (20 volumes). The mixture was slurried for 48 hours with alternating 4 hour periods at 50° C. and 5° C. (−0.5° C./min) The solid material was isolated by filtration and dried at 40 C over 3 hours. The material was analyzed by XRPD and thermal analysis.

Figure 13:
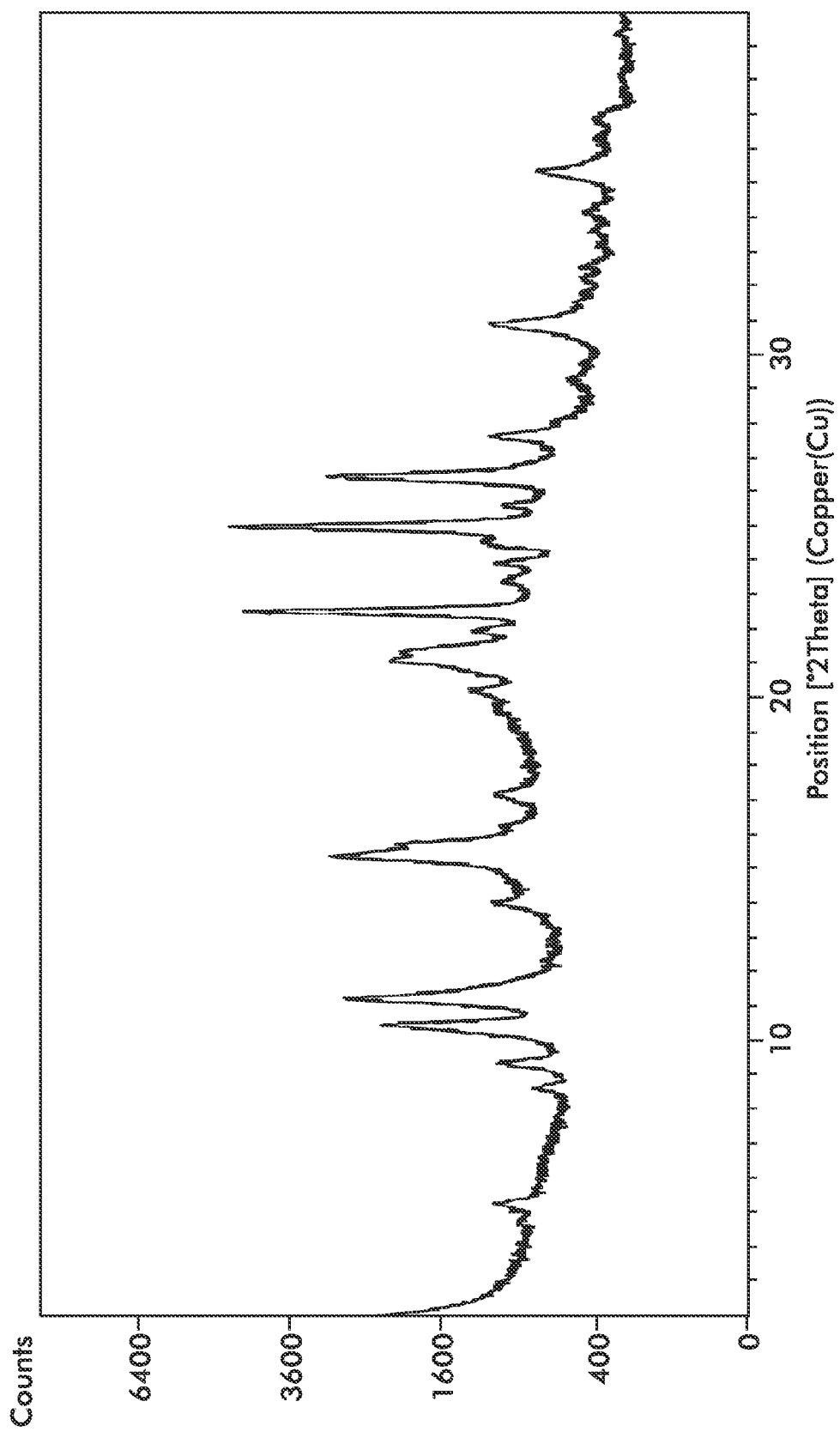
FIG. 13 is an XRPD spectrum of bendamustine free base Form 8.

The X-ray diffraction pattern characteristic of the crystalline Form 8 is shown in Table 8 (above) and FIG. 13.

Characterization of Form 8 by Thermal Analysis

Figure 14:
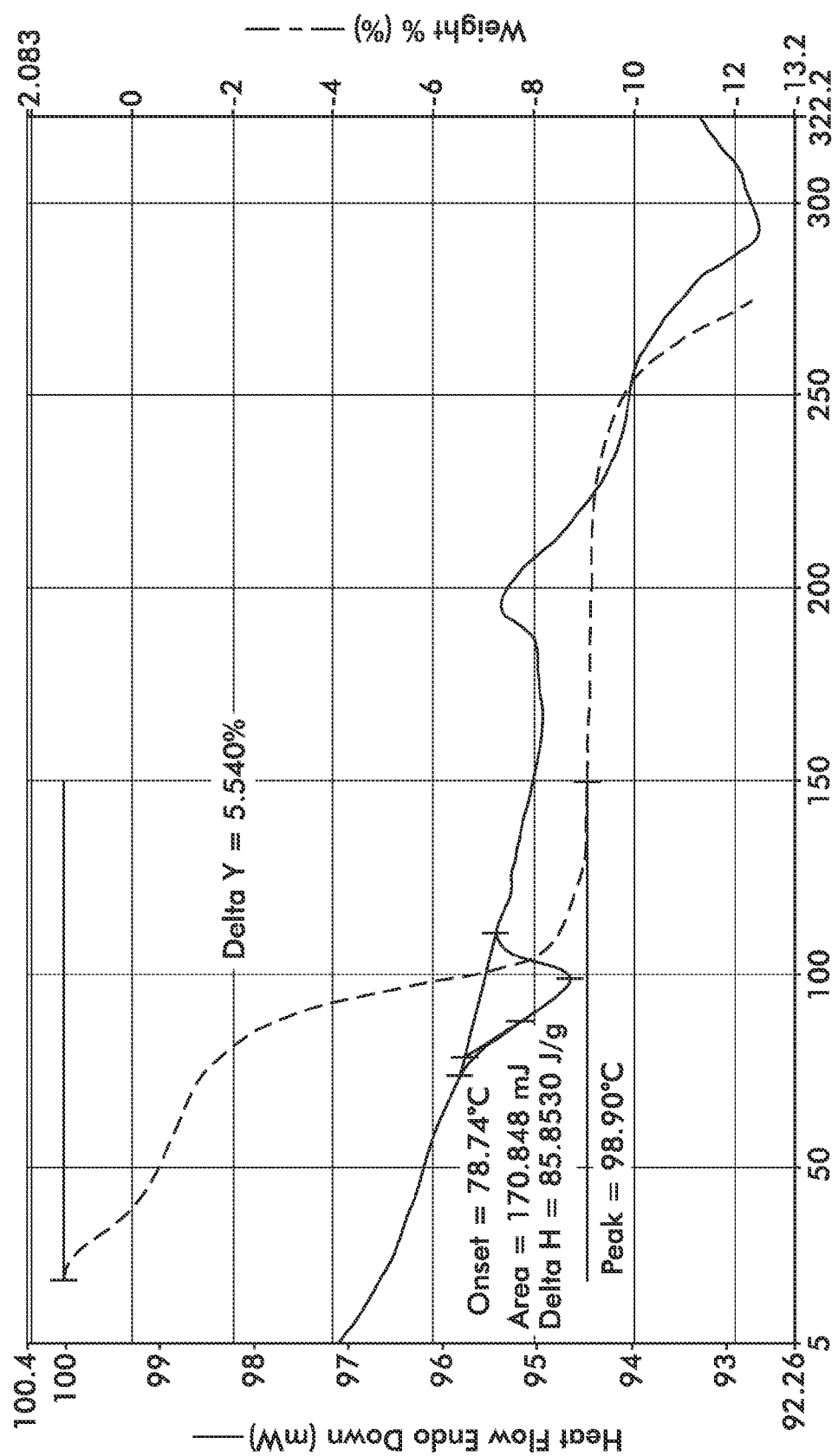
FIG. 14 is an overlay of the DSC/TGA data for bendamustine free base Form 8.

Form 8 shows a single onset at ca. 77.6° C. with an enthalpy of fusion ($\Delta H_{Fus}$) of 94.6 J/g. Form 8 in TGA experiment loses an average weight of 5.5% between 20 and 150° C. The theoretical value for incorporation of one moles of ethanol with two moles of bendamustine free base is 5.4%. (FIG. 14).

Form 9

Preparation

Slow Cool Experiments

Approximately 40 mg of Form 2 bendamustine free base was added in 800 µL of 3-pentanone (20 volumes). The sample were heated from 20° C. to 80° C. at a rate of 4.8° C./min and after 30 minutes cooled at a slow rate (0.25° C./min) to a final temperature of 5° C. and kept at that temperature for 18 The solid material was isolated by filtration and dried at 40 C over 3 hours. The material was analyzed by XRPD and thermal analysis.

Figure 15:
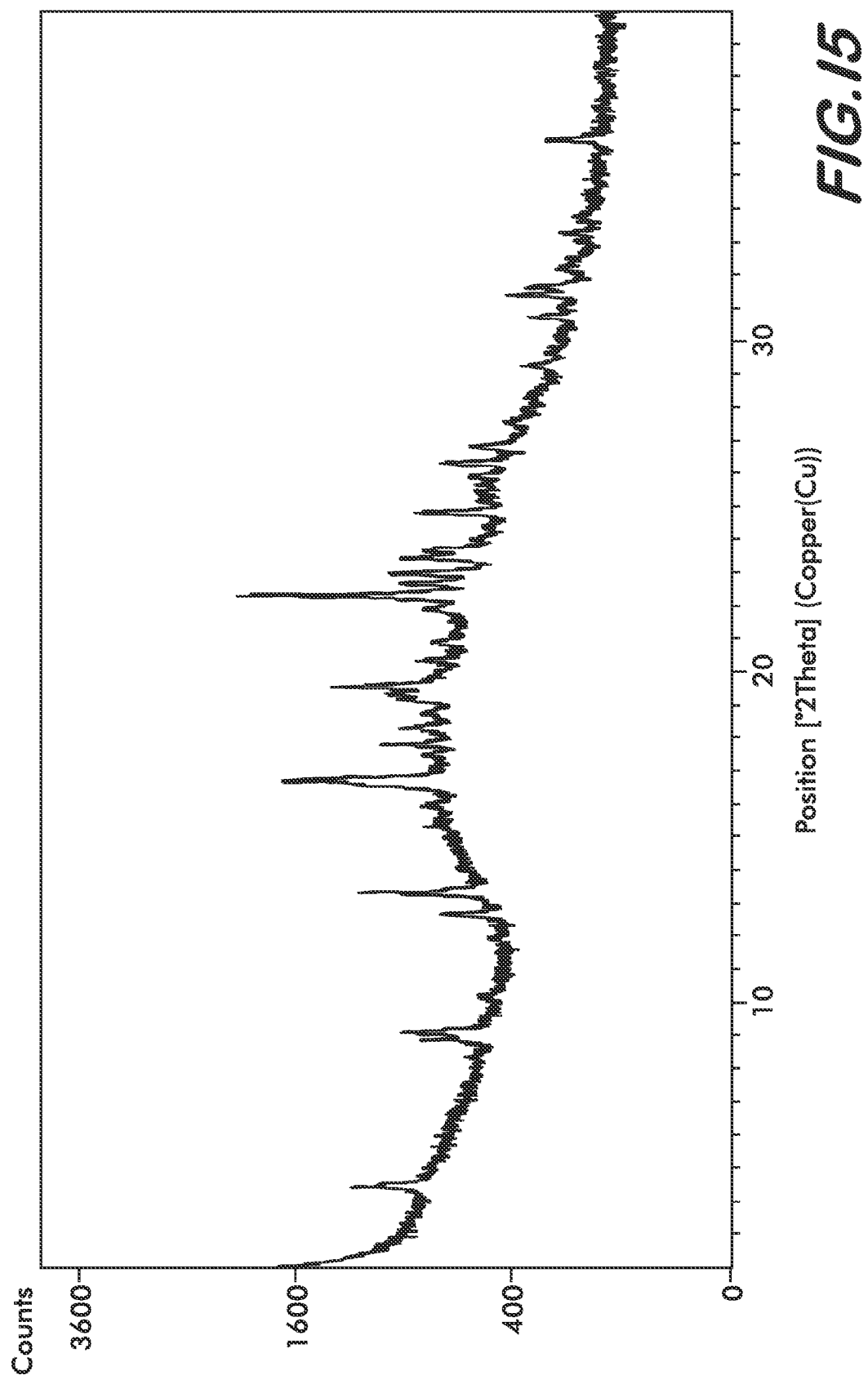
FIG. 15 is an XRPD spectrum of bendamustine free base Form 9.

The X-ray diffraction pattern characteristic of the crystalline Form 9 is shown in Table 9 (above) and FIG. 15.

Characterization of Form 9 by Thermal Analysis

Figure 16:
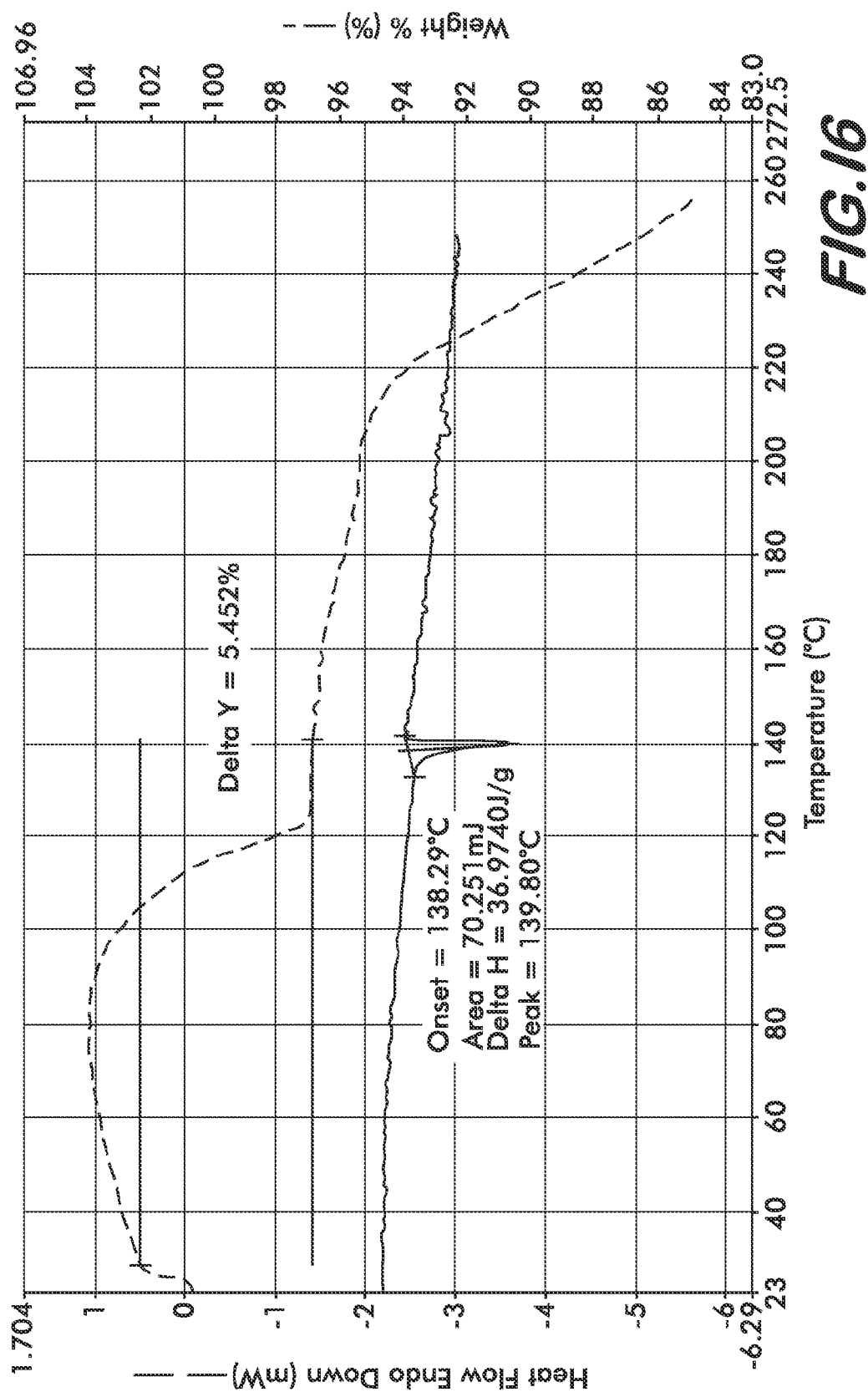
FIG. 16 is an overlay of the DSC/TGA data for bendamustine free base Form 9.

Form 9 shows a single onset at ca. 138.3° C. with an enthalpy of fusion ($\Delta H_{Fus}$) of 37.0 J/g. Form 9 in TGA experiment loses an average weight of 5.5% between 20 and 140° C. The theoretical value for incorporation of one moles of 3-pentanone with four moles of bendamustine free base is 5.7%. (FIG. 16)

Form 10

Preparation

Slow Cool Experiments

Approximately 40 mg of Form 2 bendamustine free base was added in 800 µL of toluene (20 volumes). The sample were heated from 20° C. to 80° C. at a rate of 4.8° C./min and after 30 minutes cooled at a slow rate (0.25° C./min) to a final temperature of 5° C. and kept at that temperature for 18 h. The solid material was isolated by filtration and dried at 40 C over 3 hours. The material was analyzed by XRPD and thermal analysis.

Figure 17:
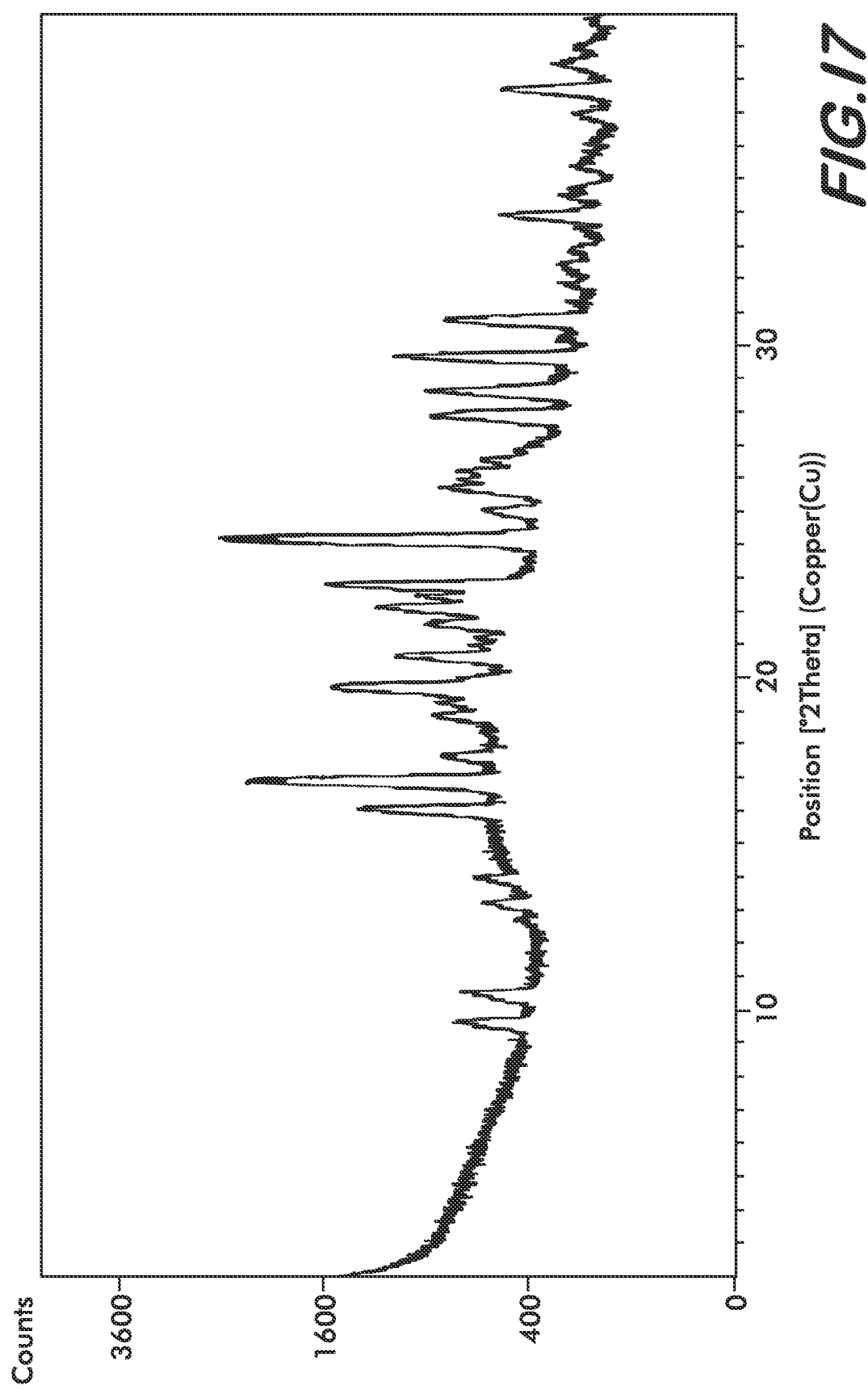
FIG. 17 is an XRPD spectrum of bendamustine free base Form 10.

The X-ray diffraction pattern characteristic of the crystalline Form 10 is shown in Table 10 (above) and FIG. 17.

Characterization of Form 10 by Thermal Analysis

Figure 18:
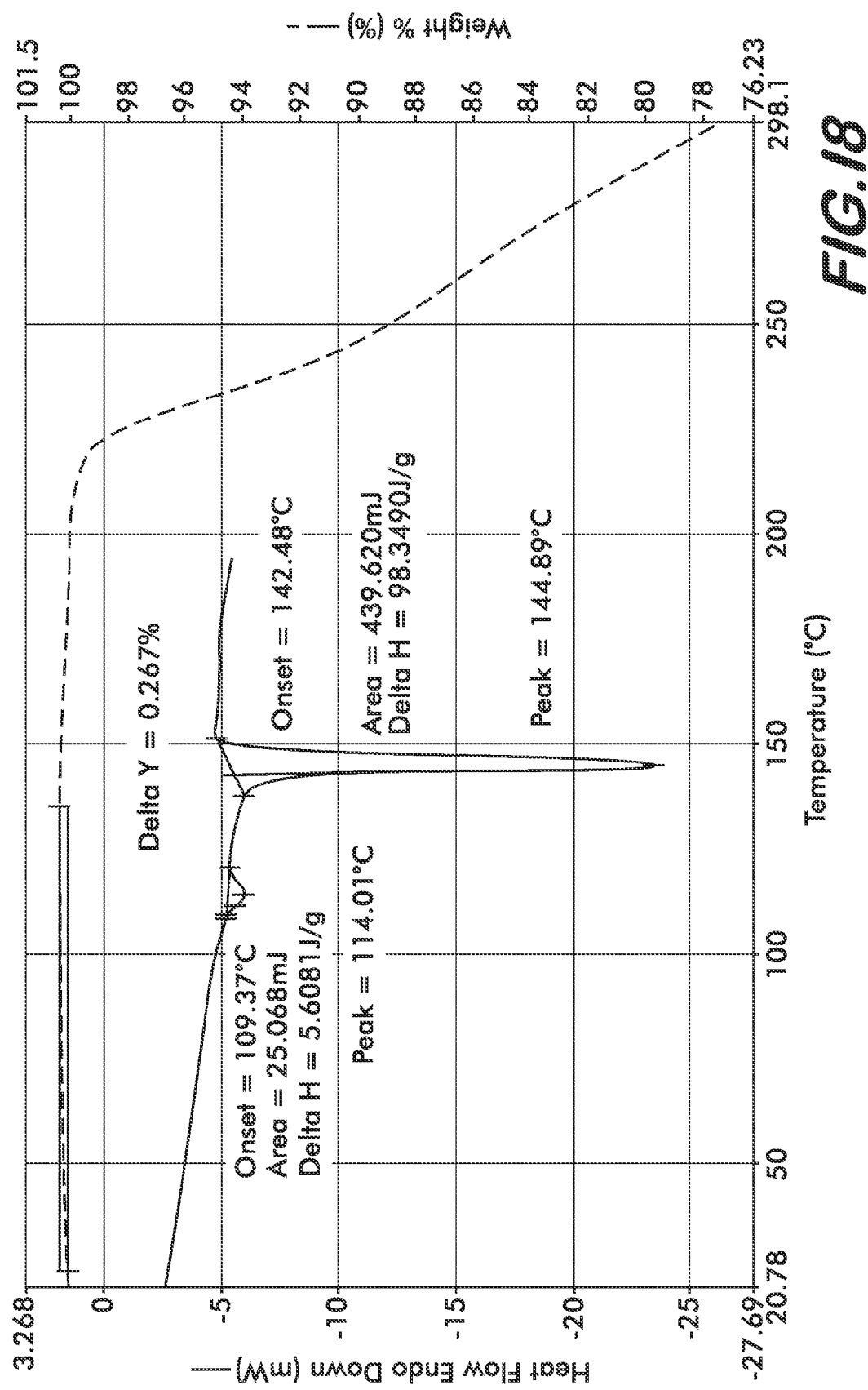
FIG. 18 is an overlay of the DSC/TGA data for bendamustine free base Form 10.

Form $I_0$ shows two onsets at ca. 109.3 and 144.9° C. with an enthalpy of fusion ($\Delta H_{Fus}$) of 5.6 and 98.3 J/g. (FIG. 18). No loss of mass is detected by TGA. The existence of a desolvation process was discounted because no loss of weight was detected by TGA.

Form 11

Preparation

Crystallization by Slurry Experiments

Approximately 40 mg of Form 3 bendamustine free base in 400 µL of 1 butanol or 1-4 dioxane or isopropyl acetate was stirred at 25° C. during 48 h. The solid was isolated by filtration and dried at 40° C. over 3 hours. The material was analyzed by XRPD and thermal analysis.

Figure 19:
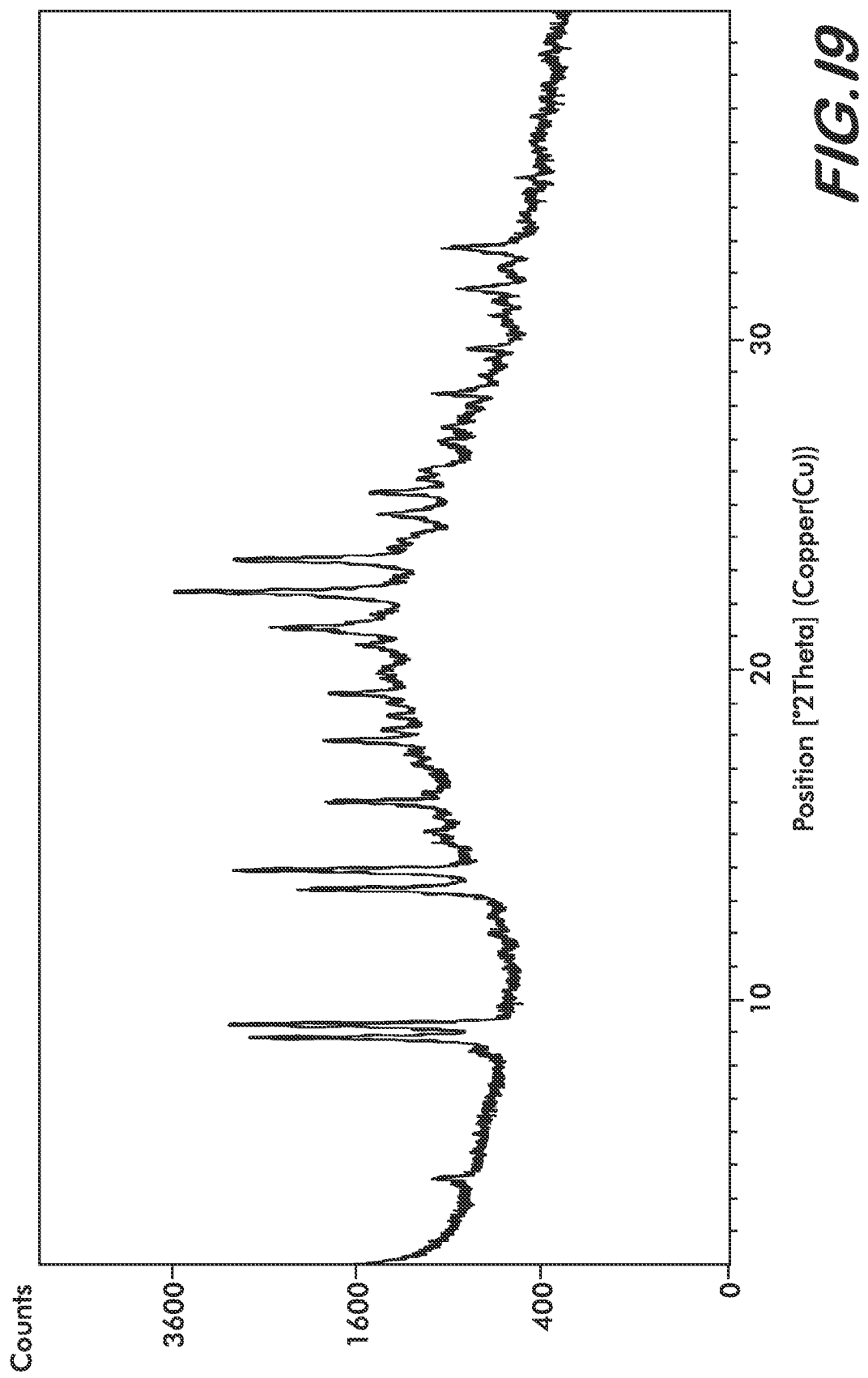
FIG. 19 is an XRPD spectrum of bendamustine free base Form 11.

The X-ray diffraction pattern characteristic of the crystalline Form 11 is shown in Table 11 (above) and FIG. 19.

Characterization of Form 11 by Thermal Analysis

Figure 20:
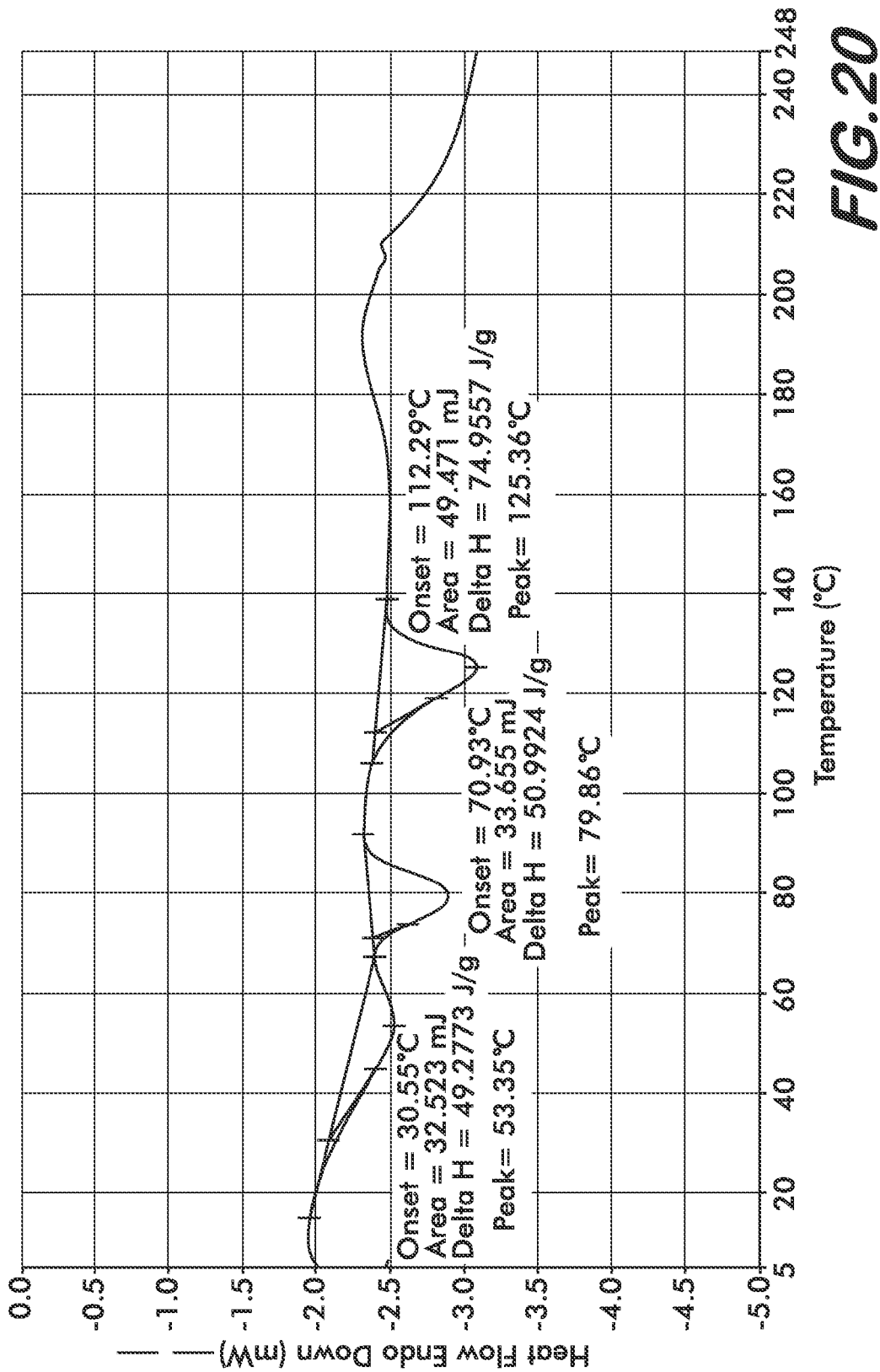
FIG. 20 is an overlay of the DSC/TGA data for bendamustine free base Form 11.

Form 11 shows a multiple onset at ca. 30.5, 70.9 and 112.3° C. with an enthalpy of fusion ($\Delta H_{Fus}$) of 49.3, 51.0 and 74.9 J/g. (FIG. 20)

Form 12

Preparation

Crystallization by Slurry Experiments

Approximately 40 mg of Form 3 bendamustine free base was added in 400 µL of N,N-dimethylformamide. The slurry was stirred at 25° C. during 48 hours The solid was isolated by filtration and dried at 40° C. during 3 hours. The material was analyzed by XRPD and thermal analysis.

Figure 21:
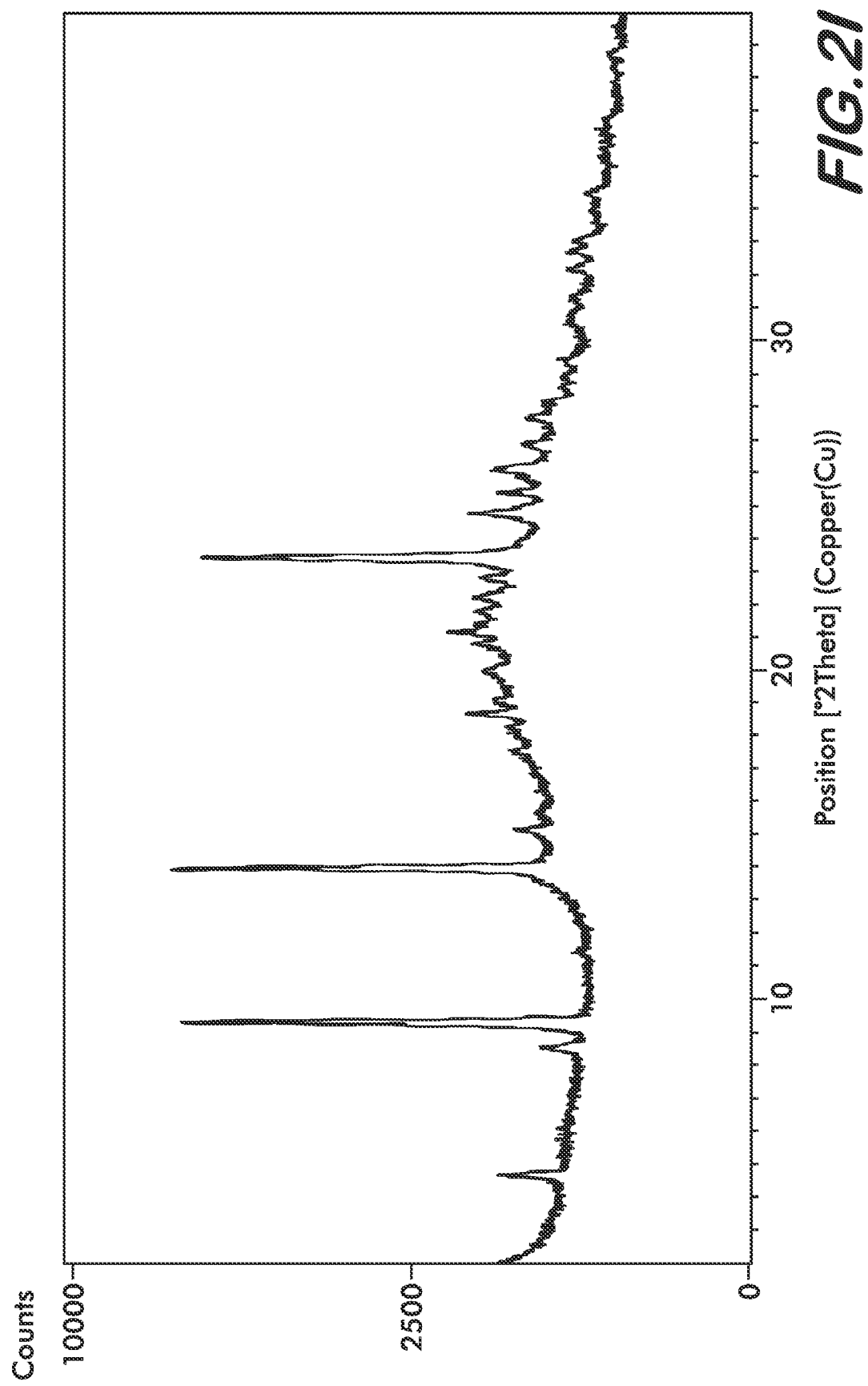
FIG. 21 is an XRPD spectrum of bendamustine free base Form 12.

The X-ray diffraction pattern characteristic of the crystalline Form 12 is shown in Table 12 (above) and FIG. 21.

Characterization of Form 12 by Thermal Analysis

Figure 22:
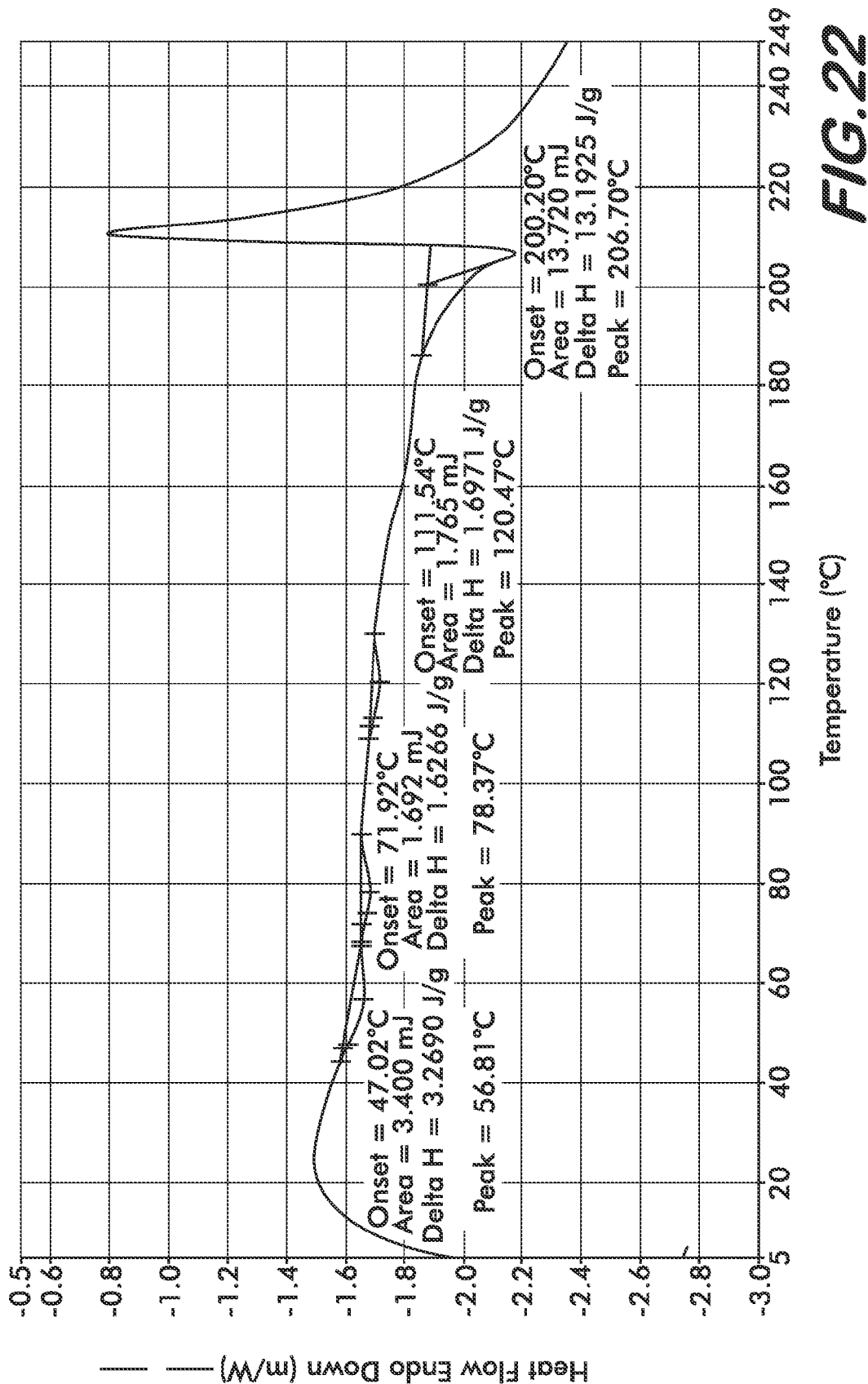
FIG. 22 is an overlay of the DSC/TGA data for bendamustine free base Form 12.

Form 12 shows a multiple onset at ca. 56.8, 72.0, 111.5 and 206.7 with an enthalpy of fusion ($\Delta H_{Fus}$) of 3.3, 1.6, 1.7 and 13.2 J/g (FIG. 22).

Form 13

Preparation

Slow Cool Experiments

Approximately 40 mg of Form 3 bendamustine free base in 800 µL of solvent (20 volumes) were slurried in the methyl tert-butyl ether, 3-pentanone and 1-propanol. The samples were heated from 20° C. to 80° C. at a rate of 4.8° C./min and after 30 minutes cooled at a slow rate (0.25° C./min) to a final temperature of 5° C. and kept at that temperature for 18 h The solid material was isolated by filtration and dried at 40 C over 3 hours. The material was analyzed by XRPD and thermal analysis.

The X-ray diffraction pattern characteristic of the crystalline Form 13 is shown in Table 13 (above) and FIG. 23.

Characterization of Form 13 by Thermal Analysis

Figure 24:
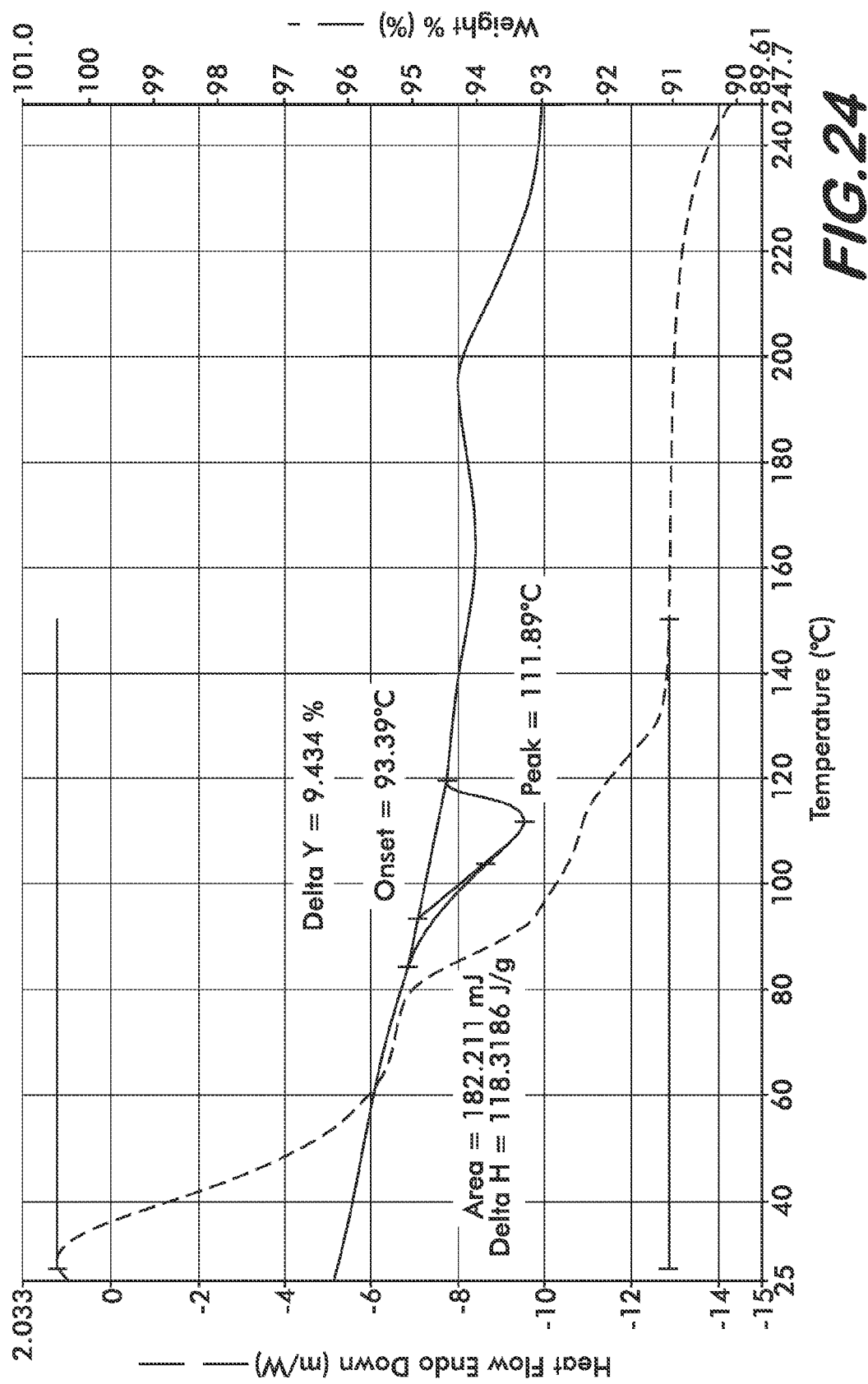
FIG. 24 is an overlay of the DSC/TGA data for bendamustine free base Form 13.

Form 13 shows a single onset at ca. 93.4° C. with an enthalpy of fusion ($\Delta H_{Fus}$) of 118.2 J/g. TGA experiment loses an average weight of 9.4% between 20 and 150° C. The theoretical value for incorporation of two moles of water with one mole of bendamustine free base is 9.1% (FIG. 24).

Form 14

Preparation

Crystallization by Slurry Experiment

Approximately 40 mg of Form 3 bendamustine free base in 400 µL of acetonitrile was shaken at 25° C. during 48 hours. The solid was isolated by filtration and dried at 40° C. over 3 hours. The material was analyzed by XRPD and thermal analysis.

Figure 25:
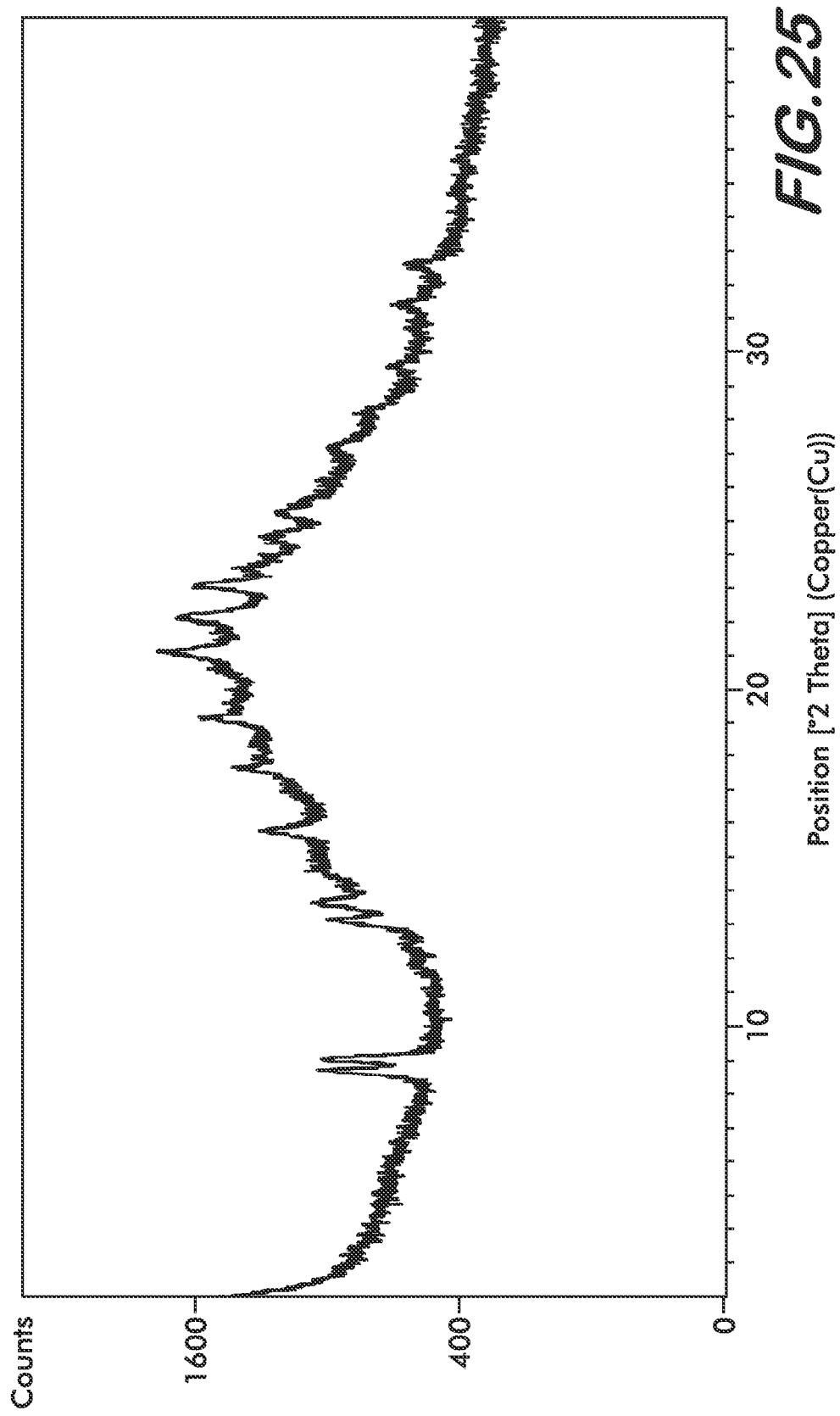
FIG. 25 is an XRPD spectrum of bendamustine free base Form 14.

The X-ray diffraction pattern characteristic of the crystalline Form 14 is shown in Table 14 (above) and FIG. 25.

Characterization of Form 14 by Thermal Analysis

Figure 26:
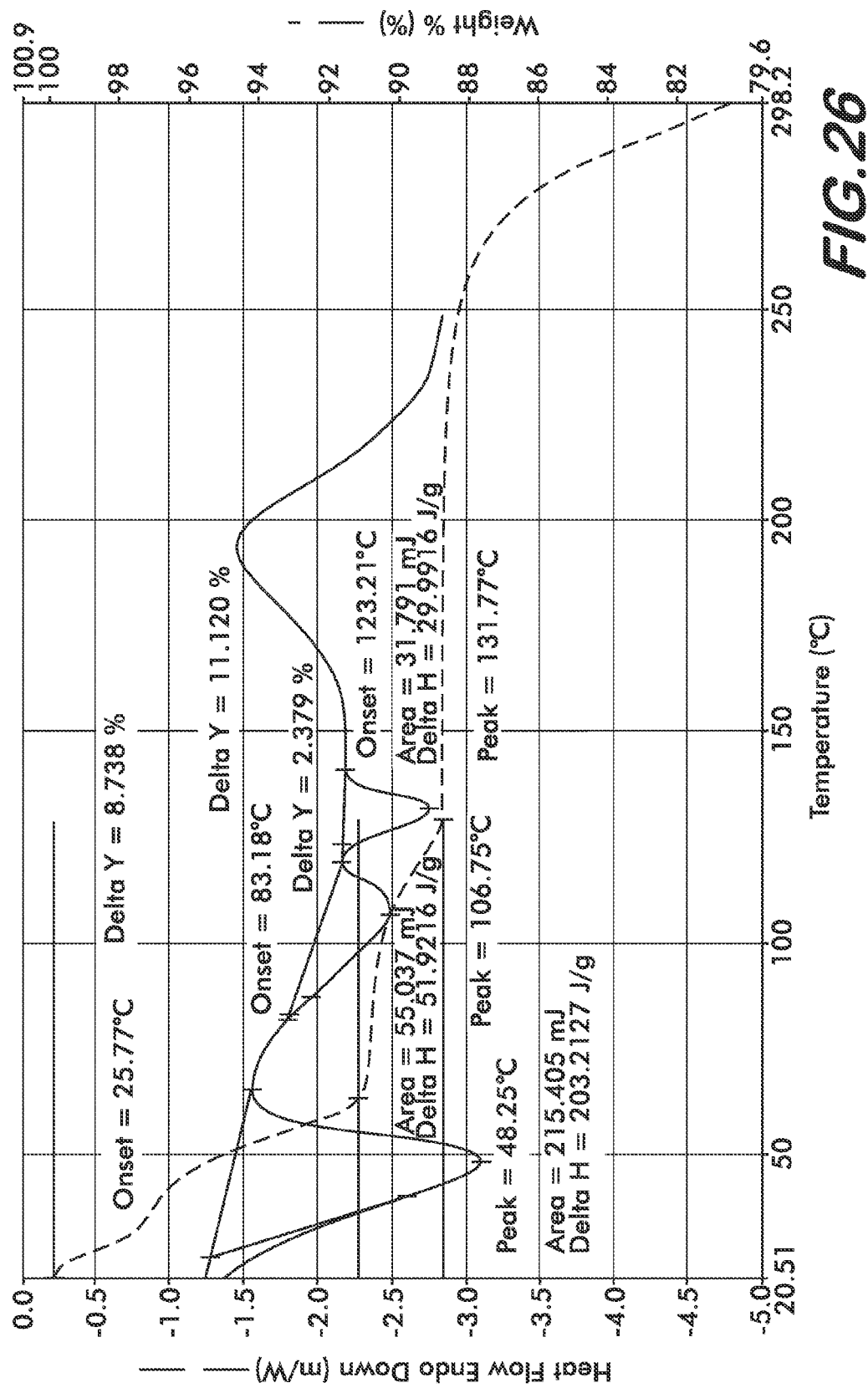
FIG. 26 is an overlay of the DSC/TGA data for bendamustine free base Form 14.

Form 14 shows a multiple onset at ca. 25.8, 83.2 and 123.2 with an enthalpy of fusion ($\Delta H_{Fus}$) of 215.4, 51.9 and 30.0 J/g. TGA experiment loses an average weight of 11.1% between 20 and 150° C. The theoretical value for incorporation of five moles of water with two moles of bendamustine free base is 11.2% (FIG. 26).

Form 15

Preparation

Crystallization by Slurry Experiments

Approximately 25 mg of Form 1 bendamustine free base in 1.25 mL of tetrahydrofuran was dissolved at 50° C. On cooling to ambient temperature, precipitation occurred. The solid was isolated and rapidly analyzed by XRPD.

Figure 27:
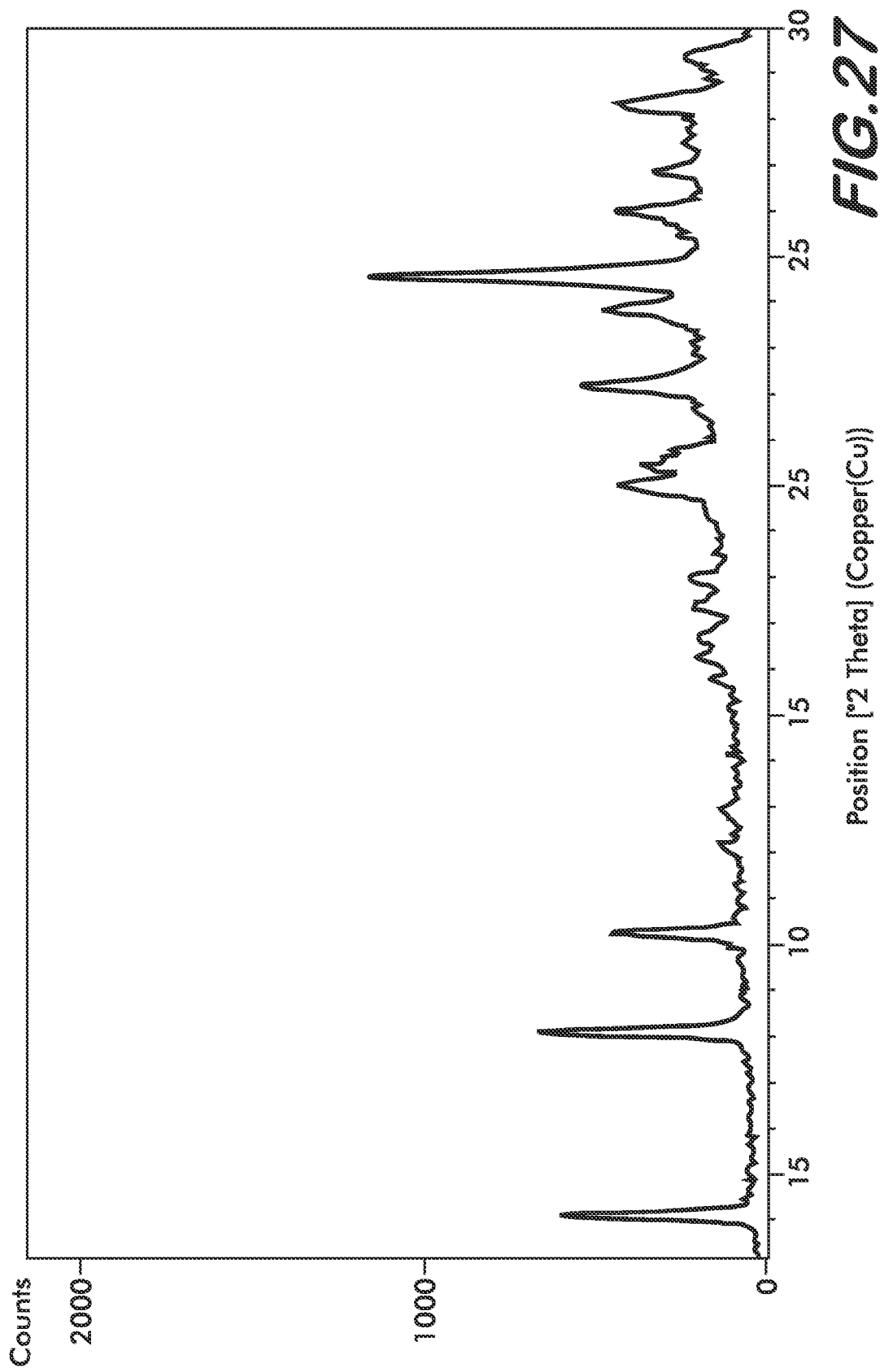
FIG. 27 is an XRPD spectrum of bendamustine free base Form 15.

The X-ray diffraction pattern characteristic of the crystalline Form 15 is shown in Table 15 (above) and FIG. 27.

Characterization of Form 15 by Thermogravimetry Analysis

Figure 28:
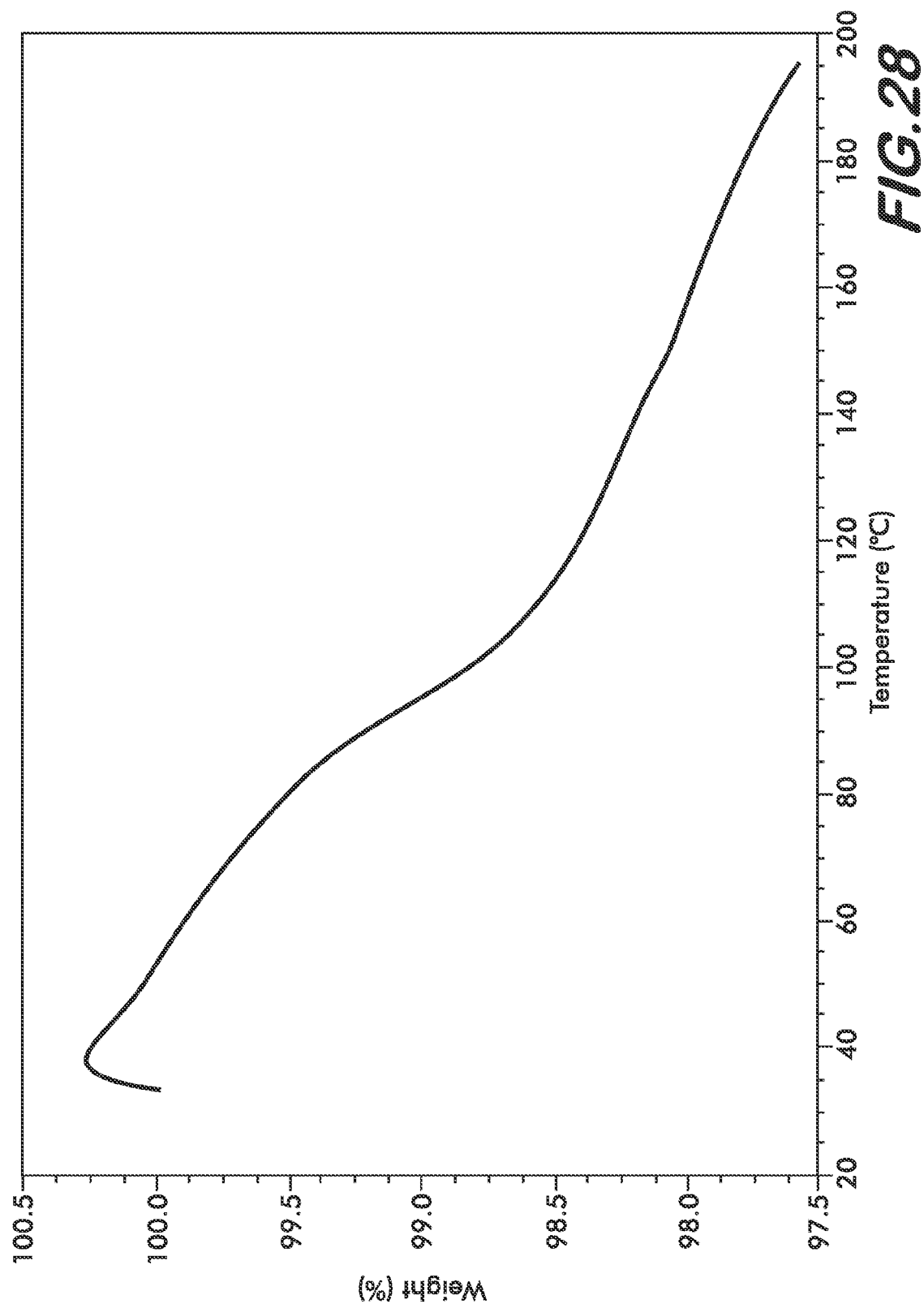
FIG. 28 is TGA data for bendamustine free base Form 15, with a sample size of 1.4590 mg, running from ambient to 200° C. at 10° C. per minute.

Thermogravimetric analysis is consistent with the THF solvate of Bendamustine Free Base (FIG. 28).

Characterization of Form 15 by $^1$NMR

Figure 29:
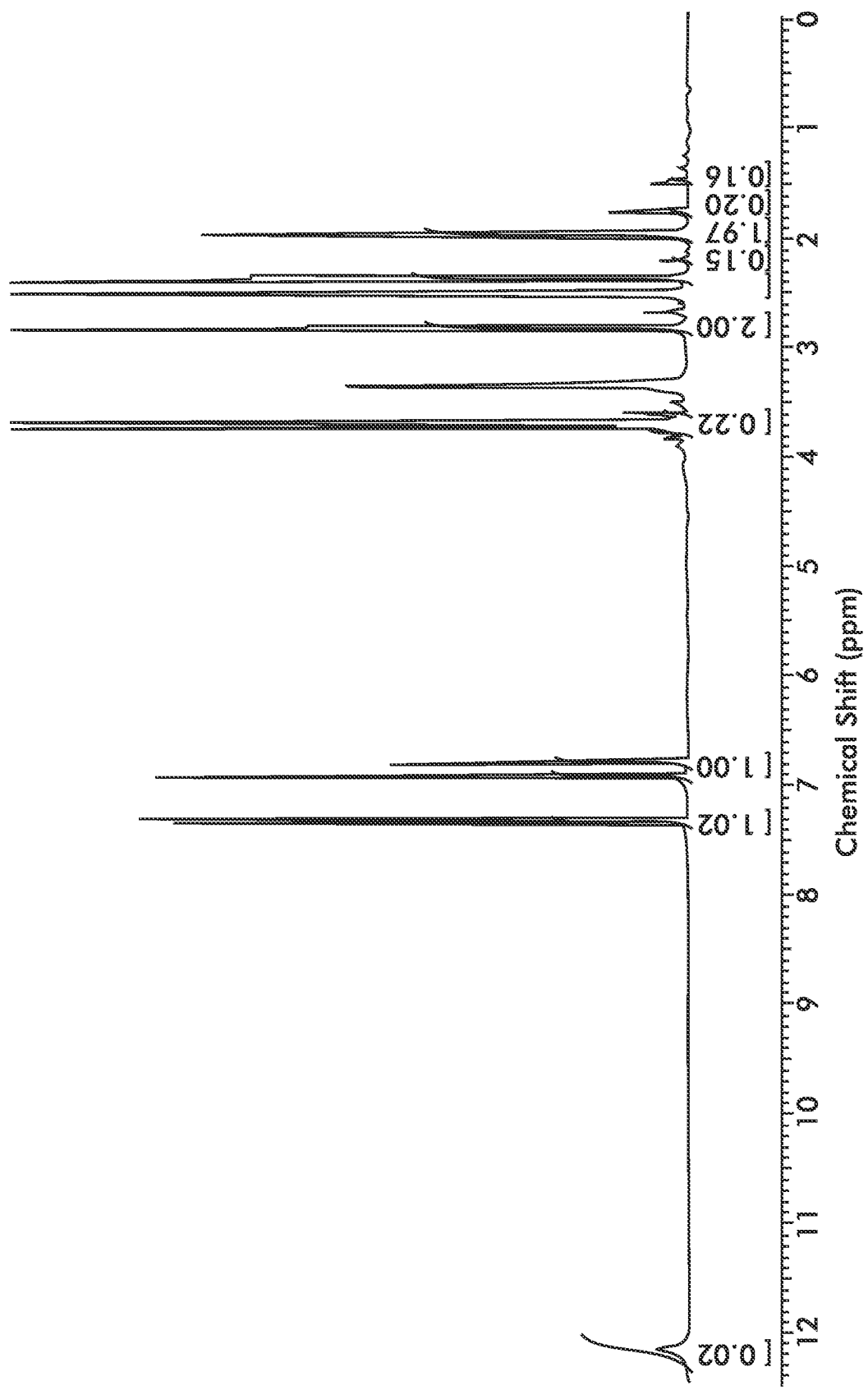
FIG. 29 is a $^1$H NMR of bendamustine free base Form 15.

The $^1$H NMR spectrum confirmed that THF (0.05 equivalents) is present (FIG. 29).

Amorphous Bendamustine Free Base

Preparation

Figure 30:
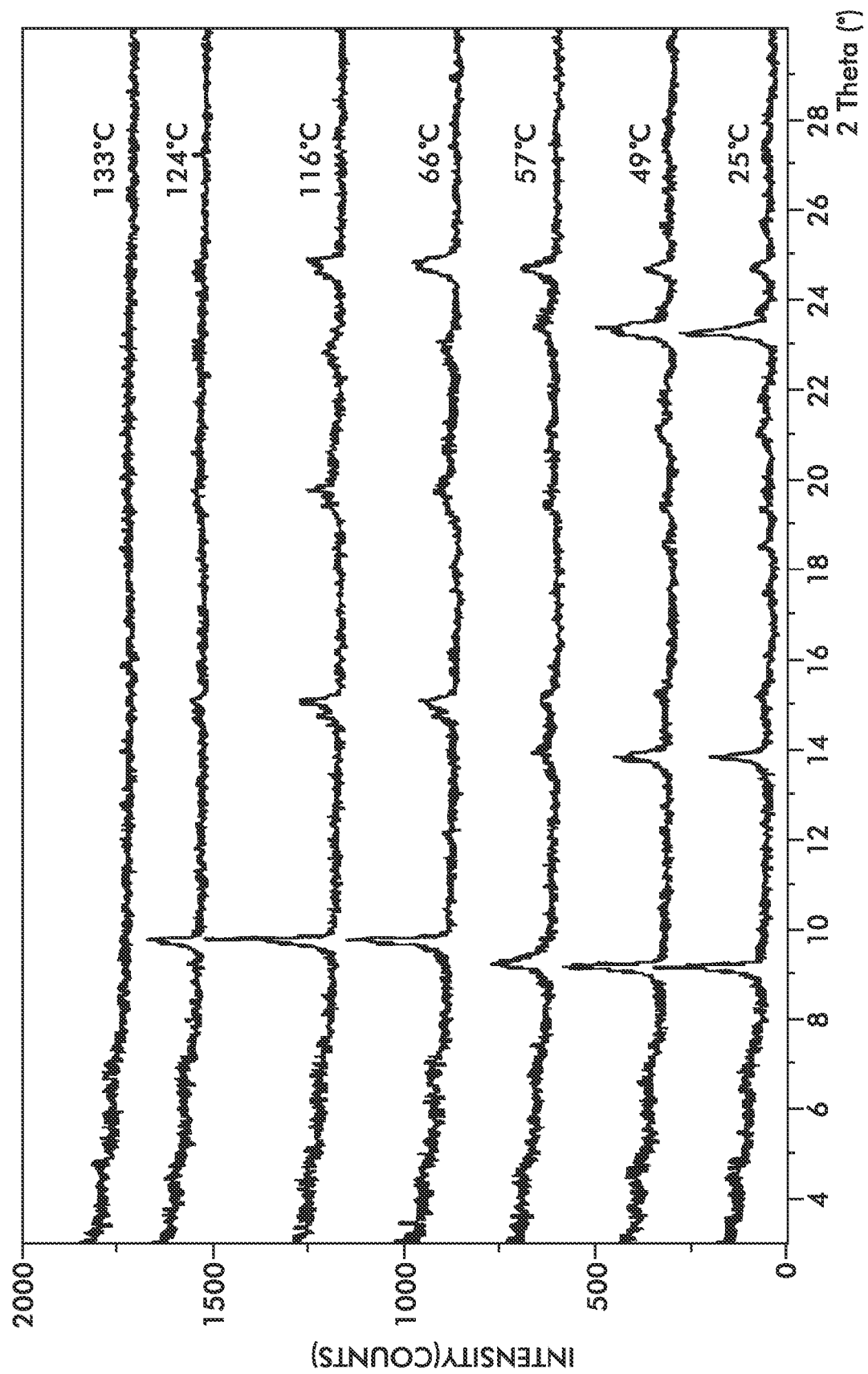
FIG. 30 is a Variable Temperature XRPD for Form 3.
Figure 31:
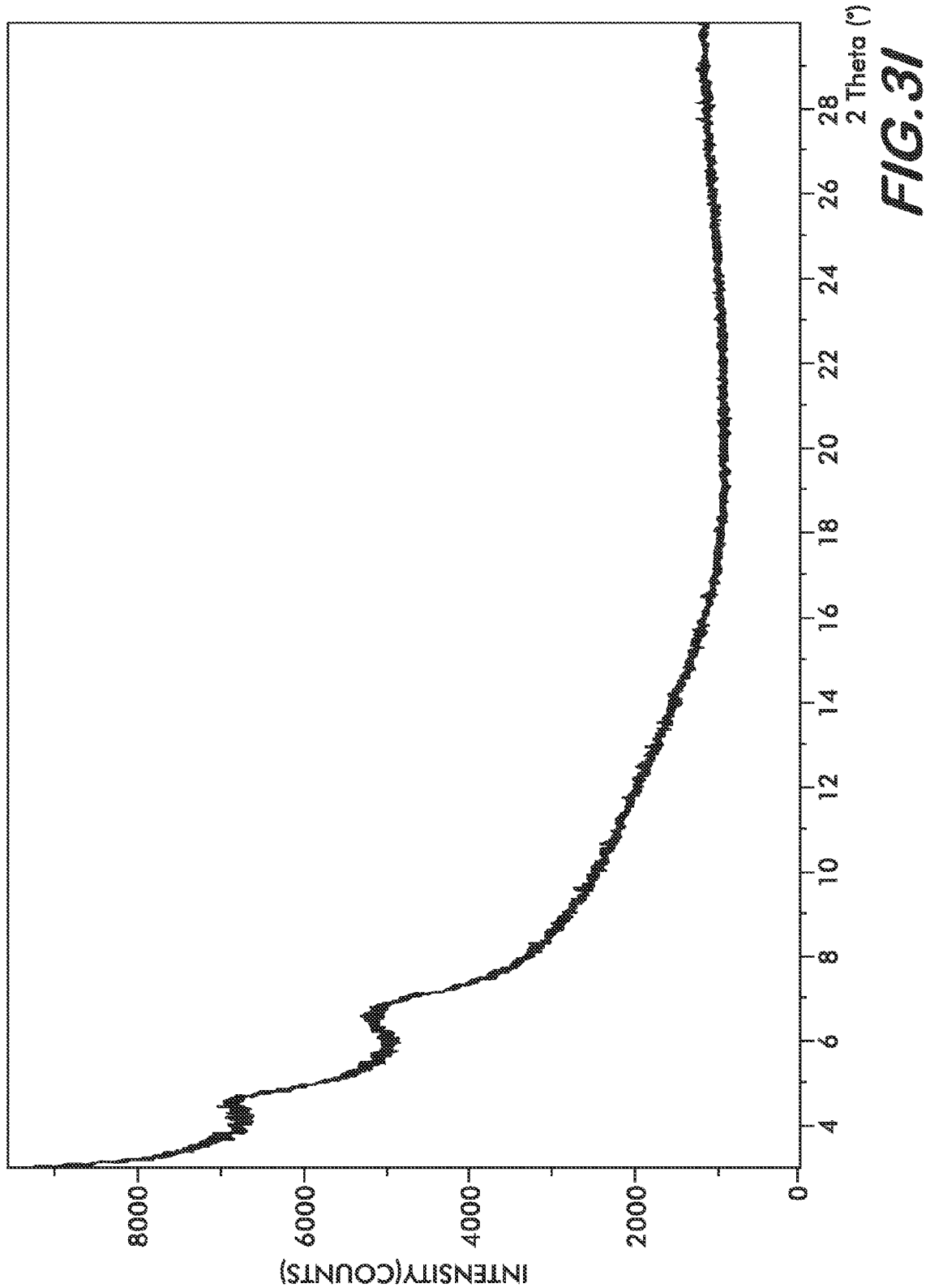
FIG. 31 is an XPPD spectrum of amorphous bendamustine free base.

During the characterization of Form 3 by VT-XRPD, amorphous bendamustine free base was formed. No significant, solid-solid transformations take place in the temperature range of 25° C. to 50° C. for Form 3. Dehydration of the hydrate to Form 4 takes place in the temperature range 50° C. to 66° C. The crystallinity disappears in the temperature range 124° C. to 133° C. FIG. 30. After 133° C., the sample converts to amorphous material. FIG. 31.

A first embodiment of the present invention provides a pharmaceutical composition comprising bendamustine free base selected from the group consisting of amorphous bendamustine free base, bendamustine free base Form 1, bendamustine free base Form 2, bendamustine free base Form 3, bendamustine free base Form 4, bendamustine free base Form 5, bendamustine free base Form 6, bendamustine free base Form 7, bendamustine free base Form 8, bendamustine free base Form 9, bendamustine free base Form 10, bendamustine free base Form 11, bendamustine free base Form 12, bendamustine free base Form 13, bendamustine free base Form 14, bendamustine free base Form 15, or a mixture thereof.

A second embodiment provides the pharmaceutical composition of the first embodiment wherein the bendamustine free base is amorphous bendamustine free base.

A third embodiment provides the pharmaceutical composition of the first embodiment wherein the bendamustine free base is bendamustine free base Form 1.

A fourth embodiment provides a pharmaceutical composition of the first embodiment wherein the bendamustine free base is bendamustine free base Form 2.

A fifth embodiment provides the pharmaceutical composition of the first embodiment wherein the bendamustine free base is bendamustine free base Form 3.

A sixth embodiment provides the pharmaceutical composition of the first embodiment wherein the bendamustine free base is bendamustine free base Form 4.

A seventh embodiment provides the pharmaceutical composition of the first embodiment wherein the bendamustine free base is bendamustine free base Form 5.

An eighth embodiment provides the pharmaceutical composition of the first embodiment wherein the bendamustine free base is bendamustine free base Form 6.

A ninth embodiment provides the pharmaceutical composition of the first embodiment wherein the bendamustine free base is bendamustine free base Form 7.

A tenth embodiment provides the pharmaceutical composition of the first embodiment wherein the bendamustine free base is bendamustine free base Form 8.

An eleventh embodiment provides the pharmaceutical composition of the first embodiment wherein the bendamustine free base is bendamustine free base Form 9.

A twelfth embodiment provides the pharmaceutical composition of the first embodiment wherein the bendamustine free base is bendamustine free base Form 10.

A thirteenth embodiment provides the pharmaceutical composition of the first embodiment wherein the bendamustine free base is bendamustine free base Form 11.

A fourteenth embodiment provides the pharmaceutical composition of the first embodiment wherein the bendamustine free base is bendamustine free base Form 12.

A fifteenth embodiment provides the pharmaceutical composition of the first embodiment wherein the bendamustine free base is bendamustine free base Form 13.

A sixteenth embodiment provides the pharmaceutical composition of the first embodiment wherein the bendamustine free base is bendamustine free base Form 14.

A seventeenth embodiment provides the pharmaceutical composition of the first embodiment wherein the bendamustine free base is bendamustine free base Form 15.

An eighteenth embodiment of the present invention provides a crystalline form of bendamustine free base said bendamustine free base selected from the group consisting of bendamustine free base Form 1, bendamustine free base Form 2, bendamustine free base Form 3, bendamustine free base Form 4, bendamustine free base Form 5, bendamustine free base Form 6, bendamustine free base Form 7, bendamustine free base Form 8, bendamustine free base Form 9, bendamustine free base Form 10, bendamustine free base Form 11, bendamustine free base Form 12, bendamustine free base Form 13, bendamustine free base Form 14, bendamustine free base Form 15, or a mixture thereof.

A nineteenth embodiment provides the crystalline form of the eighteenth embodiment, wherein the bendamustine free base is bendamustine free base Form 1.

A twentieth embodiment provides the crystalline form of the eighteenth embodiment, wherein the bendamustine free base is bendamustine free base Form 2.

A twenty-first embodiment provides the crystalline form of the eighteenth embodiment, wherein the bendamustine free base is bendamustine free base Form 3.

A twenty-second embodiment provides the crystalline form of the eighteenth embodiment, wherein the bendamustine free base is bendamustine free base Form 4.

A twenty-third embodiment provides the crystalline form of the eighteenth embodiment, wherein the bendamustine free base is bendamustine free base Form 5.

A twenty-fourth embodiment provides the crystalline form of the eighteenth embodiment, wherein the bendamustine free base is bendamustine free base Form 6.

A twenty-fifth embodiment provides the crystalline form of the eighteenth embodiment, wherein the bendamustine free base is bendamustine free base Form 7.

A twenty-sixth embodiment provides the crystalline form of the eighteenth embodiment, wherein the bendamustine free base is bendamustine free base Form 8.

A twenty-seventh embodiment provides the crystalline form of the eighteenth embodiment, wherein the bendamustine free base is bendamustine free base Form 9.

A twenty-eighth embodiment provides the crystalline form of the eighteenth embodiment, wherein the bendamustine free base is bendamustine free base Form 10.

A twenty-ninth embodiment provides the crystalline form of the eighteenth embodiment, wherein the bendamustine free base is bendamustine free base Form 11.

A thirtieth embodiment provides the crystalline form of the eighteenth embodiment, wherein the bendamustine free base is bendamustine free base Form 12.

A thirty-first embodiment provides the crystalline form of the eighteenth embodiment, wherein the bendamustine free base is bendamustine free base Form 13.

A thirty-second embodiment provides the crystalline form of the eighteenth embodiment, wherein the bendamustine free base is bendamustine free base Form 14.

A thirty-third embodiment provides the crystalline form of the eighteenth embodiment, wherein the bendamustine free base is bendamustine free base Form 15.

A thirty-fourth embodiment provides the crystalline form of any of the eighteenth to thirty-third embodiments, further comprising amorphous bendamustine free base.

A thirty-fifth embodiment of the present invention provides a crystalline form of bendamustine free base that produces an X-ray powder diffraction pattern comprising one or more of the following reflections: 10.34, 22.30, 24.03, 28.43, and 29.50±0.2 degrees 2θ.

A thirty-sixth embodiment provides the crystalline form of bendamustine free base according to the thirty-fifth embodiment, that produces an X-ray powder diffraction pattern further comprising one or more of the following reflections: 16.69, 20.53, and 22.67±0.2 degrees 2θ.

A thirty-seventh embodiment of the present invention provides a crystalline form of bendamustine free base having an X-ray powder diffraction pattern substantially as depicted in FIG. 1.

A thirty-eighth embodiment provides a pharmaceutical composition comprising the crystalline form of bendamustine free base according to any one of the thirty-fifth to thirty-seventh embodiments.

A thirty-ninth embodiment of the present invention provides a crystalline form of bendamustine free base that produces an X-ray powder diffraction pattern comprising one or more of the following reflections: 10.28, 20.59, 21.55, 21.69, and 24.78±0.2 degrees 2θ.

A fortieth embodiment provides the crystalline form of bendamustine free base according to the thirty-ninth embodiment, that produces an X-ray powder diffraction pattern further comprising one or more of the following reflections: 12.54, 13.51, 15.40, and 22.39±0.2 degrees 2θ.

A forty-first embodiment of the present invention provides a crystalline form of bendamustine free base having an X-ray powder diffraction pattern substantially as depicted in FIG. 2.

A forty-second embodiment provides a pharmaceutical composition comprising the crystalline form of bendamustine free base according to any one of the thirty-eight to forty-first embodiments.

A forty-third embodiment of the present invention provides a crystalline form of bendamustine free base that produces an X-ray powder diffraction pattern comprising one or more of the following reflections: 9.41, 9.46, 14.15, 23.42, and 23.65±0.2 degrees 2θ.

A forty-fourth embodiment provides the crystalline form of bendamustine free base according to the forty-third embodiment, that produces an X-ray powder diffraction pattern further comprising one or more of the following reflections: 14.15, 18.78, and 24.83±0.2 degrees 2θ.

A forty-fifth embodiment of the present invention provides a crystalline form of bendamustine free base having an X-ray powder diffraction pattern substantially as depicted in FIG. 4.

A forty-sixth embodiment provides a pharmaceutical composition comprising the crystalline form of bendamustine free base according to any one of the forty-third to forty-fifth embodiments.

A forty-seventh embodiment of the present invention provides a crystalline form of bendamustine free base that produces an X-ray powder diffraction pattern comprising one or more of the following reflections: 9.88, 15.13, 19.92, 22.99, 24.72, and 24.98±0.2 degrees 2θ.

A forty-eighth embodiment provides the crystalline form of bendamustine free base according to the forty-seventh embodiment, that produces an X-ray powder diffraction pattern further comprising one or more of the following reflections: 19.44 and 20.70±0.2 degrees 2θ.

Figure 6:
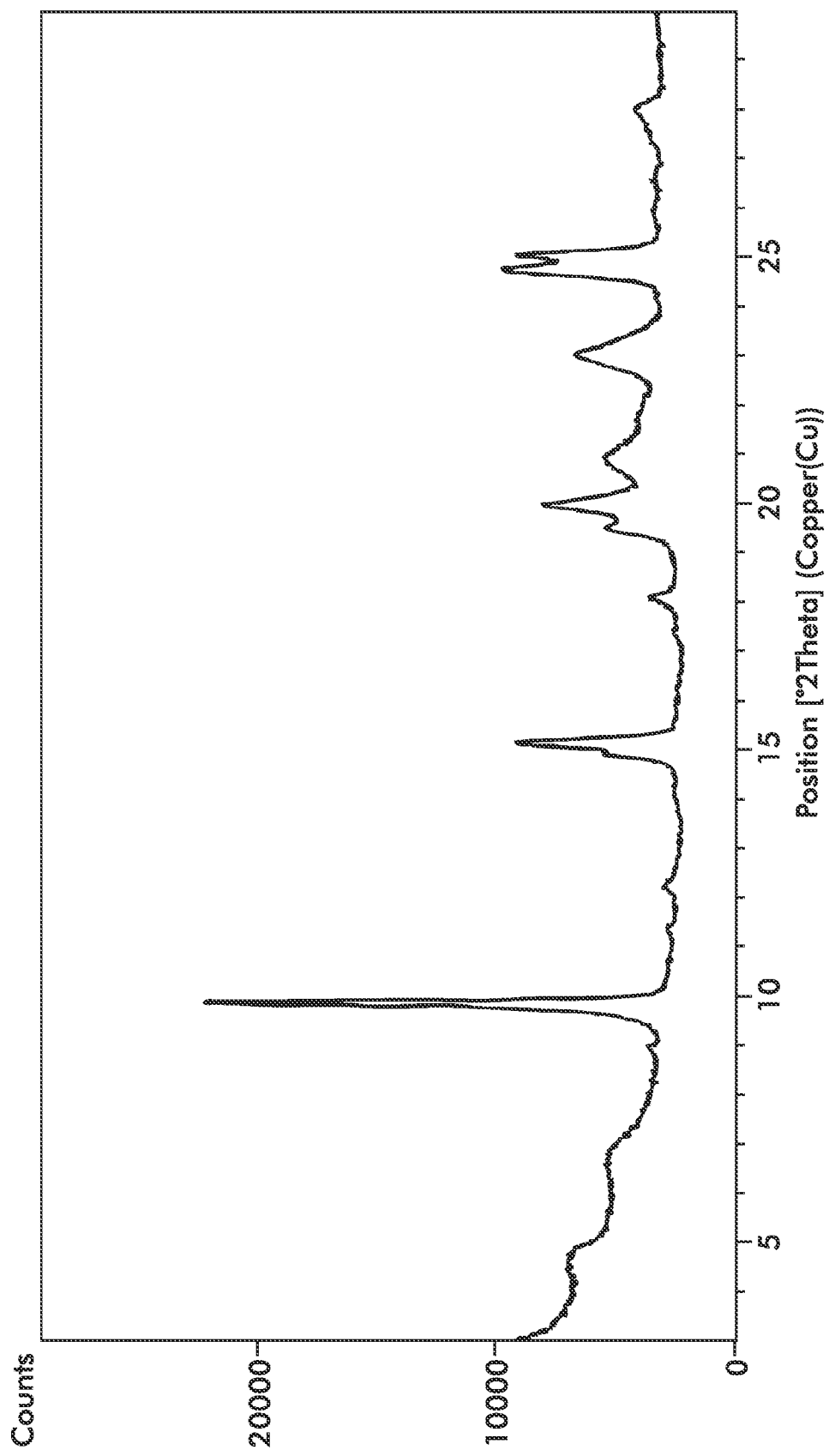
FIG. 6 is an XRPD spectrum of bendamustine free base Form 4.

A forty-ninth embodiment provides a crystalline form of bendamustine free base having an X-ray powder diffraction pattern substantially as depicted in FIG. 6.

A fiftieth embodiment provides a pharmaceutical composition comprising the crystalline form of bendamustine free base according to any one of the forty-seventh to forty-ninth embodiments.

A fifty-first embodiment of the present invention provides a crystalline form of bendamustine free base that produces an X-ray powder diffraction pattern comprising one or more of the following reflections: 8.94, 13.39, 16.04, 21.31, and 22.38±0.2 degrees 2θ.

A fifty-second embodiment provides the crystalline form of bendamustine free base according to the fifty-first embodiment, that produces an X-ray powder diffraction pattern further comprising one or more of the following reflections: 17.90, 19.29, and 25.37±0.2 degrees 2θ.

Figure 7:
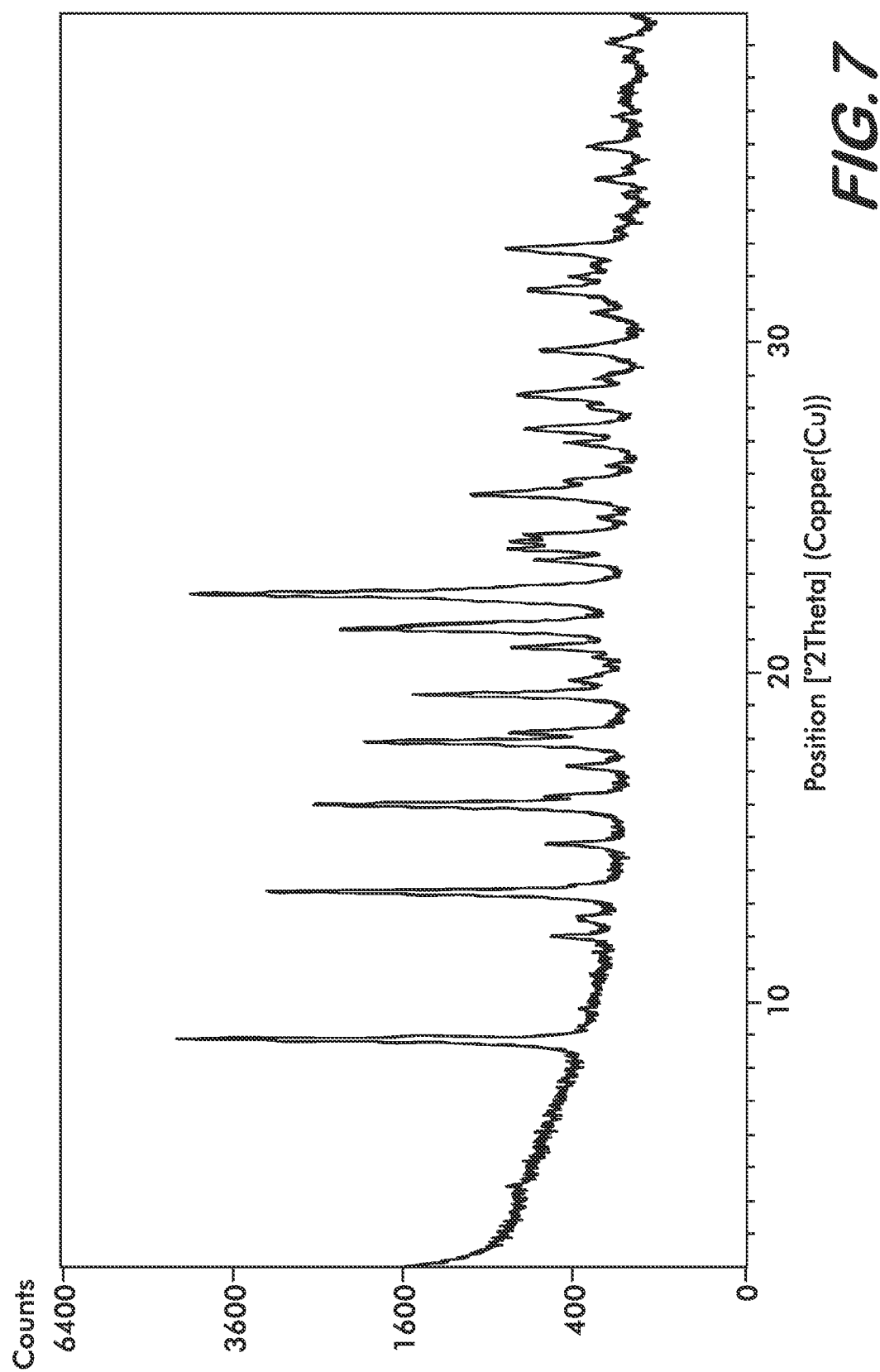
FIG. 7 is an XRPD spectrum of bendamustine free base Form 5.

A fifty-third embodiment provides a crystalline form of bendamustine free base having an X-ray powder diffraction pattern substantially as depicted in FIG. 7.

A fifty-fourth embodiment provides a pharmaceutical composition comprising the crystalline form of bendamustine free base according to any one of the fifty-first to fifty-third embodiments.

A fifty-fifth embodiment of the present invention provides a crystalline form of bendamustine free base that produces an X-ray powder diffraction pattern comprising one or more of the following reflections: 8.67, 18.15, 20.94, 22.55, and 25.46±0.2 degrees 2θ.

A fifty-sixth embodiment provides the crystalline form of bendamustine free base according to fifty-fifth embodiment, that produces an X-ray powder diffraction pattern further comprising one or more of the following reflections: 19.40, 22.95, 26.21, 27.74, and 34.62±0.2 degrees 2θ.

A fifty-seventh embodiment provides a crystalline form of bendamustine free base having an X-ray powder diffraction pattern substantially as depicted in FIG. 9.

A fifty-eighth embodiment provides a pharmaceutical composition comprising the crystalline form of bendamustine free base according to any one of the fifty-fifth to fifth-seventh embodiments.

A fifty-ninth embodiment of the present invention provides a crystalline form of bendamustine free base that produces an X-ray powder diffraction pattern comprising one or more of the following reflections: 8.51, 17.97, 21.25, 28.09, and 36.31±0.2 degrees 2θ.

A sixtieth embodiment provides the crystalline form of bendamustine free base according to the fifty-ninth embodiment, that produces an X-ray powder diffraction pattern further comprising one or more of the following reflections: 11.42, 14.23, 23.29, 24.04, and 28.09±0.2 degrees 2θ.

A sixty-first embodiment provides a crystalline form of bendamustine free base having an X-ray powder diffraction pattern substantially as depicted in FIG. 11.

A sixty-second embodiment provides a pharmaceutical composition comprising the crystalline form of bendamustine free base according to any one of the fifty-ninth to sixty-first embodiments.

A sixty-third embodiment of the present invention provides a crystalline form of bendamustine free base that produces an X-ray powder diffraction pattern comprising one or more of the following reflections: 9.34, 10.45, 11.17, 15.32, 22.48, 24.98, and 26.40±0.2 degrees 2θ.

A sixty-fourth embodiment provides the crystalline form of bendamustine free base according to the sixty-third embodiment, that produces an X-ray powder diffraction pattern further comprising one or more of the following reflections: 15.72, 21.01, 21.30, and 30.87±0.2 degrees 2θ.

A sixty-fifth embodiment provides a crystalline form of bendamustine free base having an X-ray powder diffraction pattern substantially as depicted in FIG. 13.

A sixty-sixth embodiment provides a pharmaceutical composition comprising the crystalline form of bendamustine free base according to any one of the sixty-third to sixty-fifth embodiments.

A sixty-seventh embodiment provides a crystalline form of bendamustine free base that produces an X-ray powder diffraction pattern comprising one or more of the following reflections: 4.44, 13.34, 16.73, 19.54, and 22.32±0.2 degrees 2θ.

A sixty-eighth embodiment provides the crystalline form of bendamustine free base according to the sixty-seventh embodiment, that produces an X-ray powder diffraction pattern further comprising one or more of the following reflections: 22.98, 23.45, and 24.80±0.2 degrees 2θ.

A sixty-ninth embodiment provides a crystalline form of bendamustine free base having an X-ray powder diffraction pattern substantially as depicted in FIG. 15.

A seventieth embodiment provides a pharmaceutical composition comprising the crystalline form of bendamustine free base according to any one of the sixty-seventh to sixty-ninth embodiments.

A seventy-first embodiment of the present invention provides a crystalline form of bendamustine free base that produces an X-ray powder diffraction pattern comprising one or more of the following reflections: 16.82, 16.93, 17.06, 19.68, 19.83, 22.87, 24.24, 28.63, and 29.72±0.2 degrees 2θ.

A seventy-second embodiment provides the crystalline form of bendamustine free base according to the seventy-first embodiment, that produces an X-ray powder diffraction pattern further comprising one or more of the following reflections: 16.13, 25.75, and 37.71±0.2 degrees 2θ.

A seventy-third embodiment provides a crystalline form of bendamustine free base having an X-ray powder diffraction pattern substantially as depicted in FIG. 17.

A seventy-fourth embodiment provides a pharmaceutical composition comprising the crystalline form of bendamustine free base according to any one of the seventy-first to seventy-third embodiments.

A seventy-fifth embodiment of the present invention provides a crystalline form of bendamustine free base that produces an X-ray powder diffraction pattern comprising one or more of the following reflections: 8.90, 9.28, 13.94, 22.36, and 23.33±0.2 degrees 2θ.

A seventy-sixth embodiment provides the crystalline form of bendamustine free base according to the seventy-fifth embodiment, that produces an X-ray powder diffraction pattern further comprising one or more of the following reflections: 16.01, 19.30, 21.29, and 25.38±0.2 degrees 2θ.

A seventy-seventh embodiment provides a crystalline form of bendamustine free base having an X-ray powder diffraction pattern substantially as depicted in FIG. 19.

A seventy-eighth embodiment provides a pharmaceutical composition comprising the crystalline form of bendamustine free base according to any one of seventy-fifth to seventy-seventh embodiments.

A seventy-ninth embodiment provides a crystalline form of bendamustine free base that produces an X-ray powder diffraction pattern comprising one or more of the following reflections: 9.31, 9.35, 13.97, 14.03, and 23.38±0.2 degrees 2θ.

An eightieth embodiment provides the crystalline form of bendamustine free base according to the seventy-ninth embodiment, that produces an X-ray powder diffraction pattern further comprising one or more of the following reflections: 4.71, 24.75, and 26.06±0.2 degrees 2θ.

An eighty-first embodiment provides a crystalline form of bendamustine free base having an X-ray powder diffraction pattern substantially as depicted in FIG. 21.

An eighty-second embodiment provides a pharmaceutical composition comprising the crystalline form of bendamustine free base according to any one of the seventy-ninth to eighty-first embodiments.

An eighty-third embodiment of the present invention provides a crystalline form of bendamustine free base that produces an X-ray powder diffraction pattern comprising one or more of the following reflections: 9.84, 14.76, 19.67, and 24.62±0.2 degrees 2θ.

An eighty-fourth embodiment of the present invention provides the crystalline form of bendamustine free base according to the eighty-third embodiment, that produces an X-ray powder diffraction pattern further comprising one or more of the following reflections: 21.35, 22.21, 23.20, and 26.91±0.2 degrees 2θ.

An eighty-fifth embodiment provides a crystalline form of bendamustine free base having an X-ray powder diffraction pattern substantially as depicted in FIG. 23.

An eighty-sixth embodiment provides a pharmaceutical composition comprising the crystalline form of bendamustine free base according to any one of the eighty-third to eighty-fifth embodiments.

An eighty-seventh embodiment of the present invention provides a crystalline form of bendamustine free base that produces an X-ray powder diffraction pattern comprising one or more of the following reflections: 9.14, 17.72, 19.19, 21.13, 22.10, 23.12, and 23.61±0.2 degrees 2θ.

An eighty-eighth embodiment provides the crystalline form of bendamustine free base according to the eighty-seventh embodiment, that produces an X-ray powder diffraction pattern further comprising one or more of the following reflections: 8.74, 15.85, 24.59, 25.28, and 27.16±0.2 degrees 2θ.

An eighty-ninth embodiment provides a crystalline form of bendamustine free base having an X-ray powder diffraction pattern substantially as depicted in FIG. 25.

A ninetieth embodiment provides a pharmaceutical composition comprising the crystalline form of bendamustine free base according to any one of the eighty-seventh to eighty-ninth embodiments.

A ninety-first embodiment of the present invention provides a crystalline form of bendamustine free base that produces an X-ray powder diffraction pattern comprising one or more of the following reflections: 24.56, 19.92, 10.26, 8.10, and 4.09±0.2 degrees 2θ.

A ninety-second embodiment provides the crystalline form of bendamustine free base according to the ninety-first embodiment, that produces an X-ray powder diffraction pattern further comprising one or more of the following reflections: 17.96, 23.83, 26.01, 28.39, and 29.43±0.2 degrees 2θ.

A ninety-third embodiment provides a crystalline form of bendamustine free base having an X-ray powder diffraction pattern substantially as depicted in FIG. 27.

A ninety-fourth embodiment provides a pharmaceutical composition comprising the crystalline form of bendamustine free base according to any one of claims 91 to 93.

A ninety-fifth embodiment provides a method of treating chronic lymphocytic leukemia, Hodgkin's disease, non-Hodgkin's lymphoma, multiple myeloma or breast cancer comprising administering to a patient in need thereof a therapeutically effective amount of a preparation prepared from a composition according to any one the first to ninety-fourth embodiments.

As those skilled in the art will appreciate, numerous modifications and variations of the present invention are possible in view of the above teachings. It is therefore understood that within the scope of the appended claims, the invention can be practiced otherwise than as specifically described herein, and the scope of the invention is intended to encompass all such variations.

What is claimed is:

1. A pharmaceutical composition comprising bendamustine free base selected from the group consisting of bendamustine free base Form 1, bendamustine free base Form 2, bendamustine free base Form 3, bendamustine free base Form 4, bendamustine free base Form 5, bendamustine free base Form 6, bendamustine free base Form 7, bendamustine free base Form 8, bendamustine free base Form 9, bendamustine free base Form 10, bendamustine free base Form 11, bendamustine free base Form 12, bendamustine free base Form 13, bendamustine free base Form 14, bendamustine free base Form 15, or a mixture thereof.

2. A crystalline form of bendamustine free base said bendamustine free base selected from the group consisting of bendamustine free base Form 1, bendamustine free base Form 2, bendamustine free base Form 3, bendamustine free base Form 4, bendamustine free base Form 5, bendamustine free base Form 6, bendamustine free base Form 7, bendamustine free base Form 8, bendamustine free base Form 9, bendamustine free base Form 10, bendamustine free base Form 11, bendamustine free base Form 12, bendamustine free base Form 13, bendamustine free base Form 14, bendamustine free base Form 15, or a mixture thereof.

3. A crystalline form of bendamustine free base, according to claim 2, that produces an X-ray powder diffraction pattern comprising one or more of the following reflections: 10.34, 22.30, 24.03, 28.43, and 29.50±0.2 degrees 2θ.

4. A pharmaceutical composition comprising the crystalline form of bendamustine free base according to claim 3.

5. A crystalline form of bendamustine free base, according to claim 2, that produces an X-ray powder diffraction pattern comprising one or more of the following reflections: 10.28, 20.59, 21.55, 21.69, and 24.78±0.2 degrees 2θ.

6. A pharmaceutical composition comprising the crystalline form of bendamustine free base according to claim 5.

7. A crystalline form of bendamustine free base, according to claim 2, that produces an X-ray powder diffraction pattern comprising one or more of the following reflections: 9.41, 9.46, 14.15, 23.42, and 23.65±0.2 degrees 2θ.

8. A pharmaceutical composition comprising the crystalline form of bendamustine free base according to claim 7.

9. A crystalline form of bendamustine free base, according to claim 2, that produces an X-ray powder diffraction pattern comprising one or more of the following reflections: 9.88, 15.13, 19.92, 22.99, 24.72, and 24.98±0.2 degrees 2θ.

10. A pharmaceutical composition comprising the crystalline form of bendamustine free base according to claim 9.

11. A crystalline form of bendamustine free base, according to claim 2, that produces an X-ray powder diffraction pattern comprising one or more of the following reflections: 8.94, 13.39, 16.04, 21.31, and 22.38±0.2 degrees 2θ.

12. A pharmaceutical composition comprising the crystalline form of bendamustine free base according to claim 11.

13. A crystalline form of bendamustine free base, according to claim 2, that produces an X-ray powder diffraction pattern comprising one or more of the following reflections: 8.67, 18.15, 20.94, 22.55, and 25.46±0.2 degrees 2θ.

14. A pharmaceutical composition comprising the crystalline form of bendamustine free base according to claim 13.

15. A crystalline form of bendamustine free base, according to claim 2, that produces an X-ray powder diffraction pattern comprising one or more of the following reflections: 8.51, 17.97, 21.25, 28.09, and 36.31±0.2 degrees 2θ.

16. A pharmaceutical composition comprising the crystalline form of bendamustine free base according to claim 15.

17. A crystalline form of bendamustine free base, according to claim 2, that produces an X-ray powder diffraction pattern comprising one or more of the following reflections: 9.34, 10.45, 11.17, 15.32, 22.48, 24.98, and 26.40±0.2 degrees 2θ.

18. A pharmaceutical composition comprising the crystalline form of bendamustine free base according to claim 17.

19. A crystalline form of bendamustine free base, according to claim 2, that produces an X-ray powder diffraction pattern comprising one or more of the following reflections: 4.44, 13.34, 16.73, 19.54, and 22.32±0.2 degrees 2θ.

20. A pharmaceutical composition comprising the crystalline form of bendamustine free base according to claim 19.

21. A crystalline form of bendamustine free base, according to claim 2, that produces an X-ray powder diffraction pattern comprising one or more of the following reflections: 16.82, 16.93, 17.06, 19.68, 19.83, 22.87, 24.24, 28.63, and 29.72±0.2 degrees 2θ.

22. A pharmaceutical composition comprising the crystalline form of bendamustine free base according to claim 21.

23. A crystalline form of bendamustine free base, according to claim 2, that produces an X-ray powder diffraction pattern comprising one or more of the following reflections: 8.90, 9.28, 13.94, 22.36, and 23.33±0.2 degrees 2θ.

24. A pharmaceutical composition comprising the crystalline form of bendamustine free base according to claim 23.

25. A crystalline form of bendamustine free base, according to claim 2, that produces an X-ray powder diffraction pattern comprising one or more of the following reflections: 9.31, 9.35, 13.97, 14.03, and 23.38±0.2 degrees 2θ.

26. A pharmaceutical composition comprising the crystalline form of bendamustine free base according to claim 25.

27. A crystalline form of bendamustine free base, according to claim 2, that produces an X-ray powder diffraction pattern comprising one or more of the following reflections: 9.84, 14.76, 19.67, and 24.62±0.2 degrees 2θ.

28. A pharmaceutical composition comprising the crystalline form of bendamustine free base according to claim 27.

29. A crystalline form of bendamustine free base, according to claim 2, that produces an X-ray powder diffraction pattern comprising one or more of the following reflections: 9.14, 17.72, 19.19, 21.13, 22.10, 23.12, and 23.61±0.2 degrees 2θ.

30. A pharmaceutical composition comprising the crystalline form of bendamustine free base according to claim 29.

31. A crystalline form of bendamustine free base, according to claim 2, that produces an X-ray powder diffraction pattern comprising one or more of the following reflections: 24.56, 19.92, 10.26, 8.10, and 4.09±0.2 degrees 2θ.

32. A pharmaceutical composition comprising the crystalline form of bendamustine free base according to claim 31.

33. A method of treating chronic lymphocytic leukemia, Hodgkin's disease, non-Hodgkin's lymphoma, multiple myeloma or breast cancer comprising administering to a patient in need thereof a therapeutically effective amount of a preparation prepared from a composition according to claim 1.

* * * * *